(12) United States Patent
Altman et al.

(10) Patent No.: US 9,290,490 B2
(45) Date of Patent: Mar. 22, 2016

(54) AMINOPYRIMIDINES AS SYK INHIBITORS

(75) Inventors: Michael D. Altman, Needham, MA (US); Kaleen Konrad Childers, Newton, MA (US); Maria Emilia Di Francesco, Houston, TX (US); John Michael Ellis, Needham, MA (US); Christian Fischer, Natick, MA (US); Jonathan Grimm, Ashburn, VA (US); Andrew M. Haidle, Cambridge, MA (US); Solomon D. Kattar, Arlington, MA (US); Alan B. Northrup, Reading, MA (US); Ryan D. Otte, Natick, MA (US); Alessia Petrocchi, Houston, TX (US); Adam J. Schell, Decatur, GA (US); Hua Zhou, Acton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 65 days.

(21) Appl. No.: 14/116,207

(22) PCT Filed: May 4, 2012

(86) PCT No.: PCT/US2012/036423
§ 371 (c)(1),
(2), (4) Date: Nov. 7, 2013

(87) PCT Pub. No.: WO2012/154519
PCT Pub. Date: Nov. 15, 2012

(65) Prior Publication Data
US 2014/0148474 A1    May 29, 2014

Related U.S. Application Data

(60) Provisional application No. 61/484,418, filed on May 10, 2011.

(51) Int. Cl.
| | |
|---|---|
| *C07D 401/12* | (2006.01) |
| *A61K 31/506* | (2006.01) |
| *C07D 487/04* | (2006.01) |
| *C07D 401/14* | (2006.01) |
| *C07D 417/12* | (2006.01) |
| *C07D 417/14* | (2006.01) |

(52) U.S. Cl.
CPC ............ *C07D 417/12* (2013.01); *C07D 417/14* (2013.01)

(58) Field of Classification Search
None
See application file for complete search history.

(56) References Cited

U.S. PATENT DOCUMENTS

| | | |
|---|---|---|
| 5,710,129 A | 1/1998 | Lynch et al. |
| 5,958,957 A | 9/1999 | Andersen et al. |
| 6,011,037 A | 1/2000 | Bar et al. |
| 6,248,790 B1 | 6/2001 | Uckun et al. |
| 6,432,963 B1 | 8/2002 | Hisamichi et al. |
| 6,589,950 B1 | 7/2003 | Collingwood et al. |
| 6,770,643 B2 | 8/2004 | Cox et al. |
| 6,797,706 B1 | 9/2004 | Hisamichi et al. |
| 6,897,207 B2 | 5/2005 | Cox et al. |
| 6,897,208 B2 | 5/2005 | Edwards et al. |
| 6,911,443 B2 | 6/2005 | Yura et al. |
| 6,979,694 B2 | 12/2005 | Das et al. |
| 7,060,827 B2 | 6/2006 | Singh et al. |
| 7,122,542 B2 | 10/2006 | Singh et al. |
| 7,244,739 B2 | 7/2007 | Cheng et al. |
| 7,259,154 B2 | 8/2007 | Cox et al. |
| 7,276,502 B2 | 10/2007 | Brenchley et al. |
| 7,449,458 B2 | 11/2008 | Bhamidipati et al. |
| 7,485,724 B2 | 2/2009 | Singh et al. |
| 7,538,108 B2 | 5/2009 | Singh et al. |
| 7,557,210 B2 | 7/2009 | Singh et al. |
| 7,605,172 B2 | 10/2009 | Commons |
| 7,803,801 B2 | 9/2010 | Kodama et al. |
| 8,551,984 B2 | 10/2013 | Altman et al. |
| 8,735,417 B2 | 5/2014 | Altman et al. |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0211657 A1 | 9/2006 | Singh et al. |
| 2006/0234483 A1 | 10/2006 | Araki et al. |
| 2006/0247262 A1 | 11/2006 | Baenteli et al. |
| 2007/0004626 A1 | 1/2007 | Masuda et al. |
| 2007/0015758 A1 | 1/2007 | Baruah et al. |
| 2007/0129362 A1 | 6/2007 | Bhamidipati et al. |
| 2007/0197782 A1 | 8/2007 | Clough et al. |

(Continued)

FOREIGN PATENT DOCUMENTS

| | | |
|---|---|---|
| EP | 1392684 | 9/2006 |
| EP | 1854793 A1 | 11/2007 |

(Continued)

OTHER PUBLICATIONS

Deng, G., et al., "Suppression of Skin and Kidney Disease by Inhibition of Spleen Tyrosine Kinase in Lupus-Prone Mice", Arthritis & Rheumatism, Jul. 2010, pp. 2086-2092, vol. 62, No. 7.

Friedberg, J. W., et al., "Inhibition of Syk with fostamatinib disodium has significant clinical activity in non-Hodgkin lymphoma and chronic lymphocytic leukemia", Blood, Apr. 2010, pp. 2578-2585, vol. 115, No. 13.

Krishnan, S., et al., "Differential Expression and Molecular Associations of Syk in Systemic Lupus Erythematosus T Cells", Journal of Immunology, 2008, pp. 8145-8152, vol. 181.

(Continued)

*Primary Examiner* — Samantha Shterengarts
*Assistant Examiner* — Jeanmarie Calvillo
(74) *Attorney, Agent, or Firm* — Eric A. Meade; Catherine D. Fitch

(57) ABSTRACT

The present invention provides novel pyrimidine amines of formula I which are potent inhibitors of spleen tyrosine kinase, and are useful in the treatment and prevention of diseases mediated by said enzyme, such as asthma, COPD, rheumatoid arthritis and cancer.

25 Claims, No Drawings

(56) References Cited

U.S. PATENT DOCUMENTS

| | | | |
|---|---|---|---|
| 2008/0139535 A1 | 6/2008 | Anandan et al. | |
| 2008/0182837 A1 | 7/2008 | Steurer et al. | |
| 2011/0053897 A1* | 3/2011 | Che et al. | 514/156 |
| 2012/0277192 A1 | 11/2012 | Altman et al. | |
| 2013/0090309 A1 | 4/2013 | Romeo et al. | |
| 2013/0116231 A1* | 5/2013 | Wilson et al. | 514/210.18 |
| 2013/0225548 A1 | 8/2013 | Fujihara et al. | |

FOREIGN PATENT DOCUMENTS

| | | | |
|---|---|---|---|
| JP | 2004203748 | 12/2002 | |
| WO | WO9712871 | 4/1997 | |
| WO | WO02096905 | 12/2002 | |
| WO | WO02102313 A2 | 12/2002 | |
| WO | WO03057659 | 7/2003 | |
| WO | WO03078404 | 9/2003 | |
| WO | WO2004005283 | 1/2004 | |
| WO | WO2004080463 | 9/2004 | |
| WO | WO2004087698 A2 | 10/2004 | |
| WO | WO2004087699 | 10/2004 | |
| WO | WO2005013996 | 2/2005 | |
| WO | WO2005026158 | 3/2005 | |
| WO | WO2005028475 | 3/2005 | |
| WO | WO2005033103 | 4/2005 | |
| WO | WO2005056547 | 6/2005 | |
| WO | WO2006004865 | 1/2006 | |
| WO | WO2006028833 | 3/2006 | |
| WO | WO2006050480 | 5/2006 | |
| WO | WO2006068770 | 6/2006 | |
| WO | WO2006078846 | 7/2006 | |
| WO | WO2006093247 | 9/2006 | |
| WO | WO2006129100 | 12/2006 | |
| WO | WO2006133426 | 12/2006 | |
| WO | WO2006135915 | 12/2006 | |
| WO | WO2007009681 | 1/2007 | |
| WO | WO2007009773 | 1/2007 | |
| WO | WO2007028445 | 3/2007 | |
| WO | WO2007042298 | 4/2007 | |
| WO | WO2007042299 | 4/2007 | |
| WO | WO2007070872 | 6/2007 | |
| WO | WO2007085540 | 8/2007 | |
| WO | WO2007107469 | 9/2007 | |
| WO | WO2007117692 A2 | 10/2007 | |
| WO | WO2007120980 | 10/2007 | |
| WO | WO2008024634 A1 | 2/2008 | |
| WO | WO2008073687 | 6/2008 | |
| WO | WO2008137605 A1 | 11/2008 | |
| WO | WO2009012421 A1 | 1/2009 | |
| WO | WO2009031011 | 3/2009 | |
| WO | WO2009032861 A1 | 3/2009 | |
| WO | WO2009084695 | 7/2009 | |
| WO | WO2009097287 | 8/2009 | |
| WO | WO2009102468 | 8/2009 | |
| WO | WO2009103032 | 8/2009 | |
| WO | WO2009131687 | 10/2009 | |
| WO | WO2009136995 | 11/2009 | |
| WO | WO2009145856 A1 | 12/2009 | |
| WO | WO2010027500 | 3/2010 | |
| WO | WO2010058258 | 6/2010 | |
| WO | WO2010068257 | 6/2010 | |
| WO | WO20100688257 | 6/2010 | |
| WO | WO 2011/075515 A1 * | 6/2011 | ........... C07D 417/12 |
| WO | WO2011086085 A1 | 7/2011 | |
| WO | WO2012041476 | 4/2012 | |
| WO | WO2012154518 A1 | 11/2012 | |
| WO | WO2012154519 | 11/2012 | |
| WO | WO2012154520 A1 | 11/2012 | |

OTHER PUBLICATIONS

Matsubara, S., et al., "Inhibition of Spleen Tyrosine Kinase Prevents Mast Cell Activation and Airway Hyperresponsiveness", American Journal of Respiratory Critical Care Med., 2006, pp. 56-63, vol. 173.

Penton, P.C., et al., "Spleen tyrosine kinase inhibition attenuates airway hyperresponsiveness and pollution-induced enchanced airway response in a chronic mouse model of asthma", Journal of Allergy Clin. Immunology, 2013, pp. 512-520, vol. 131.

Altman, U.S. Appl. No. 13/516,455, Notice of Allowance, Jan. 22, 2014.

Charles L. Cywin et al, Discovery and SAR of Novel [1,6]Naphthyridines as potent Inhibitors of Spleen Tyrosine Kinase (SYK), Bioorganic & Medicinal Chemistry Letters, 2003, 1415-1418, 13.

Gura, Trisha, Cancer Models: Systems for Identifying New Drugs Are Often Faulty, Science Magazine, 1997, 1041-1042, 278/5340.

Homer L. Pearce et al, Failure modes in anticancer drug discovery and development, Cancer Drug Design and Discovery, 2008, Edited by Stephen Neidle—pp. 424-435, Chapter 18.

International Preliminary Report on Patentability, Nov. 12, 2013, PCT/US2012/036423.

International Search Report, PCT/US2012/03642, Nov. 15, 2012.

Johnson et al, Relationships between drug activity in NCI preclinical in vitro and in vivo models and early clinical trials, British Journal of Cancer, 2001, 1424-1431, 64(10).

Noriyuki Yamamoto, et al, The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents, The Journal of Pharmacology and Experimental Therapeutics, 2003, 1174-1181, 306(3).

Omer N. Pamuk et al, Spleen tyrosine kinase inhibition in the treatment of autoimmune, allergic and autoinflammatory diseases, Arthritis Research & Therapy, 2010, pp. 1-11, 12:222.

Simone, Joseph V., Introduction, Part XIV, Oncology, Cecil Textbook of Medicine, 1996, 1004-1010, vol. 1—20th Ed.

EP Search Report corresponding to International Application No. PCT/US2012/036423, issued Oct. 2, 2014.

* cited by examiner

AMINOPYRIMIDINES AS SYK INHIBITORS

CROSS REFERENCE TO RELATED APPLICATIONS

This application is a U.S. National Phase application under 35 U.S.C. §371 of PCT Application No. PCT/US2012/036423, filed May 4, 2012, which claims priority under 35 U.S.C. §119(e) from U.S. Provisional Application No. 61/484,418, filed May 10, 2011.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus, pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}R1$ and or $Fc_{epsilon}R1$ receptors, and is positioned early in the signalling cascade. In mast cells, for example, the early sequence of $Fc_{epsilon}R1$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterized by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterized by a block in B cell development (M. Turner et al 1995 Nature 379: 298-302 and Cheng et al 1995, Nature 378: 303-306). These studies, along with studies on mature B cells deficient in Syk (Kurasaki et al2000, Immunol. Rev. 176:19-29), demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

U.S. Pat. No. 7,803,801 discloses Syk inhibitors having the formula:

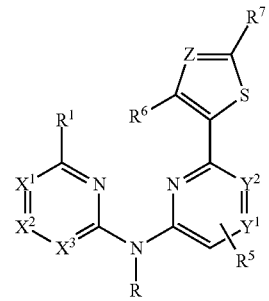

wherein the variables are as defined therein.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of Syk as well as pharmaceutical compositions containing them. As Syk inhibitors compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

The present invention provides compounds of formula I:

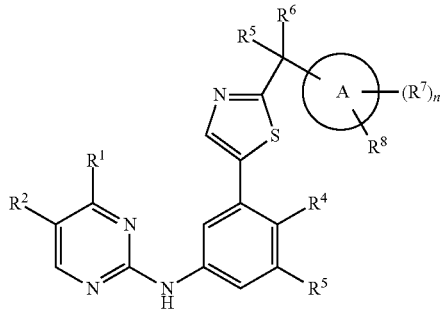

or a pharmaceutically acceptable salt thereof,
wherein
A is a carbocycle, or
the moiety A-$(R^7)_n(R^8)$ represents 1,4-dioxaspiro[4.5]decyl;
n is 0, 1, 2 or 3;
$R^1$ is $C_{1-4}$alkyl, $C_{1-4}$-fluoroalkyl, $C_{3-6}$cycloalkyl or $C_{1-4}$alkoxy;
$R^2$ is H or halogen;
$R^3$ is H, halogen, $C_{1-4}$alkyl, $C_{1-4}$haloalkyl, $C_{3-6}$cycloalkyl or $C_{1-4}$hydroxyalkyl;
$R^4$ is H or halogen;
$R^5$ is H, OH, $C_{1-4}$alkoxy, halogen or $NH_2$;
$R^6$ is H, $C_{1-4}$alkyl, $C_{1-4}$haloalkyl, $C_{3-6}$cycloalkyl or $C_{1-4}$hydroxyalkyl; or
$R^5$ and $R^6$ taken together is oxo;
$R^7$ is selected from OH and $C_{1-4}$alkyl;
$R^8$ is selected from $(CR^aR^b)_nCO_2R^c$, $CONR^dR^e$, tetrazolyl, OH, $CH_2OH$, oxo, CN, $NHCO_2R^f$ and $NHSO_2R^f$; with the proviso that $R^8$ and —$C(R^5)(R^6)$— are not attached to the same ring carbon atom;
$R^a$ and $R^b$ are each independently selected from H and methyl;
$R^c$ is H or $C_{1-4}$alkyl,
$R^d$ and $R^e$ are each independently selected from H and $C_{1-4}$alkyl; and
$R^f$ is $C_{1-4}$alkyl or benzyl.

In one group of formula I are compounds wherein the ring A is a carbocycle. In one subgroup thereof A is selected from $C_{3-6}$cycloalkyl, adamantyl and bicyclo[3.1.0]hexyl. In one embodiment A is selected from cyclopropyl, cyclobutyl, cyclopentyl and cyclohexyl. In a second embodiment A is cyclohexyl.

In another group of formula I are compounds wherein $R^1$ is $C_{1-4}$alkyl or $C_{1-4}$-fluoroalkyl. In one subgroup thereof $R^1$ is $C_{1-3}$alkyl, such as methyl, ethyl, n-propyl or isopropyl. In a second subset thereof $R^1$ is $C_{1-3}$-fluoroalkyl such as difluoromethyl or trifluoromethyl. In one embodiment $R^1$ is methyl. In a second embodiment $R^1$ is trifluoromethyl. In a third embodiment $R^1$ is difluoromethyl.

In another group of formula I are compounds wherein $R^3$ is $C_{1-4}$alkyl, $C_{1-4}$haloalkyl or $C_{3-6}$cycloalkyl. In one embodiment $R^3$ is selected from methyl, difluoromethyl and cyclopropyl. In a second embodiment $R^3$ is methyl.

In another group of formula I are compounds wherein $R^5$ is OH.

In another group of formula I are compounds wherein $R^6$ is H, $C_{1-4}$alkyl or $C_{1-4}$haloalkyl. In one subgroup thereof $R^6$ is selected from H, $C_{1-3}$alkyl and fluoro-, difluoro- and trifluoromethyl. In one embodiment $R^6$ is methyl. In a second embodiment $R^6$ is trifluoromethyl.

In another group of formula I are compounds wherein A is a carbocycle, and $R^8$ is selected from $(CR^aR^b)_nCO_2R^c$ and $C(O)NR^dR^e$. In one subgroup thereof $R^8$ is selected from $CO_2R^c$ and $C(O)NR^dR^e$. In one embodiment A is $C_{3-6}$cycloalkyl and $R^8$ is $CO_2R^c$. In a second embodiment A is $C_{3-6}$cycloalkyl and $R^8$ is $C(O)NR^dR^e$.

In another group of formula I are compounds having the formula Ia:

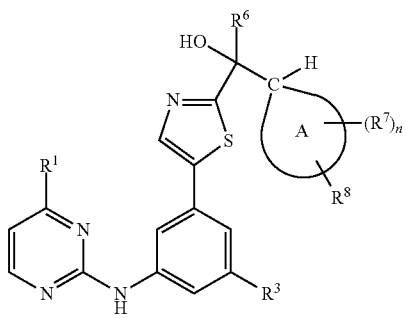

or a pharmaceutically acceptable salt thereof,
wherein
A is a carbocycle;
n is 0, 1 or 2;
$R^1$ is $C_{1-4}$alkyl or $C_{1-4}$fluoroalkyl;
$R^3$ is $C_{1-4}$alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$alkyl;
$R^8$ is $CO_2R^c$ or $CONR^dR^e$;
$R^c$ is H or $C_{1-4}$alkyl,
$R^d$ and $R^e$ are each independently selected from H and $C_{1-4}$alkyl.

In another group of formula I are compounds having the formula Ib:

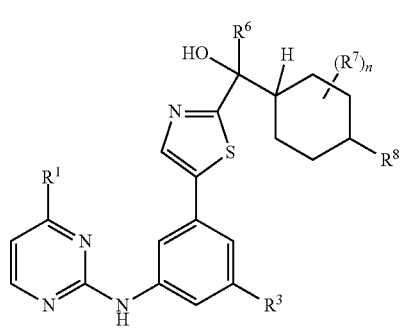

or a pharmaceutically acceptable salt thereof,
wherein
n is 0, 1 or 2;
$R^1$ is $C_{1-4}$alkyl or $C_{1-4}$fluoroalkyl;
$R^3$ is $C_{1-4}$alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$alkyl;
$R^8$ is $CO_2R^c$ or $CONR^dR^e$;

$R^c$ is H or $C_{1-4}$alkyl, $R^d$ and $R^e$ are each independently selected from H and $C_{1-4}$alkyl.

In another group of formula I are compounds having the formula Ic:

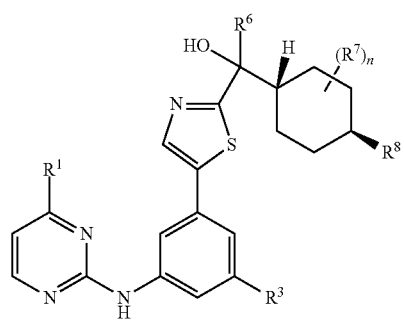

or a pharmaceutically acceptable salt thereof, wherein n, $R^1$, $R^3$, $R^6$, $R^7$, $R^8$, $R^c$, $R^d$, and $R^e$ are as described above for the compounds having the formula Ib.

In one subgroup of the compounds having the formula Ic, $R^8$ is selected from $CO_2R^c$.

Representative compounds of the present invention are as follows, where each named compound is intended to encompass its individual isomers, mixtures thereof (including racemates and diastereomeric mixtures), as well as pharmaceutically acceptable salts thereof:

4-{1-[5-(2-bromo-5-{[4-(difluoromethyl)pyrimidin-2-yl]amino}-3-methylphenyl)-1,3-thiazol-2-yl]-1-hydroxyethyl}cyclohexanecarboxylic acid;

tert-butyl 4-hydroxy-4-[(5-{3-methyl-5-[(4-methylpyrimidin-2-yl)amino]phenyl}-1,3-thiazol-2-yl)methyl]cyclohexanecarboxylate;

3-{1-hydroxy-1-[5-(3-methyl-5-{[4-(trifluoromethyl)pyrimidin-2-yl]amino}phenyl)-1,3-thiazol-2-yl]ethyl}-2,2-dimethylcyclobutanecarboxylic acid;

3-{1-hydroxy-1-[5-(3-methyl-5-{[4-(trifluoromethyl)pyrimidin-2-yl]amino}phenyl)-1,3-thiazol-2-yl]ethyl}tricyclo[3.3.1.1$^{3,7}$]decane-1-carboxylic acid;

6-{1-hydroxy-1-[5-(3-methyl-5-{[4-(trifluoromethyl)pyrimidin-2-yl]amino}phenyl)-1,3-thiazol-2-yl]ethyl}bicyclo[3.1.0]hexane-3-carboxylic acid;

methyl 4-{hydroxy[5-(3-methyl-5-{[4-(trifluoromethyl)pyrimidin-2-yl]amino}phenyl)-1,3-thiazol-2-yl]methyl}cyclohexanecarboxylate;

4-{hydroxy[5-(3-methyl-5-{[4-(trifluoromethyl)pyrimidin-2-yl]amino}phenyl)-1,3-thiazol-2-yl]methyl}cyclohexanecarboxylic acid;

(3-{1-hydroxy-1-[5-(3-methyl-5-{[4-(trifluoromethyl)pyrimidin-2-yl]amino}phenyl)-1,3-thiazol-2-yl]ethyl}-2,2-dimethylcyclobutyl)acetic acid;

4-[1-(5-{3-[(4-cyclopropyl-5-fluoropyrimidin-2-yl)amino]-5-methylphenyl}-1,3-thiazol-2-yl)-1-hydroxyethyl]cyclohexanecarboxylic acid;

ethyl 4-{1-hydroxy-1-[5-(3-methyl-5-{[4-(trifluoromethyl)pyrimidin-2-yl]amino}phenyl)-1,3-thiazol-2-yl]ethyl}-2-methylcyclohexanecarboxylate;

4-{1-[5-(3-{[4-(difluoromethyl)pyrimidin-2-yl]amino}-5-methylphenyl)-1,3-thiazol-2-yl]-2,2,2-trifluoro-1-hydroxyethyl}cyclohexanecarboxylic acid;

4-{2,2,2-trifluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid;

4-[1,2-dihydroxy-1-(5-{3-[(4-methoxypyrimidin-2-yl)amino]-5-methylphenyl}-1,3-thiazol-2-yl)ethyl]cyclohexanecarboxylic acid;

4-[1-(5-{3-[(5-fluoro-4-methylpyrimidin-2-yl)amino]-5-methylphenyl}-1,3-thiazol-2-yl)-1,2-dihydroxyethyl]cyclohexanecarboxylic acid;

N-(4-{1-hydroxy-1-[5-(3-methyl-5-{[4-(trifluoromethyl)pyrimidin-2-yl]amino}phenyl)-1,3-thiazol-2-yl]ethyl}cyclohexyl)methanesulfonamide;

N-{4-[1-hydroxy-1-(5-{3-methyl-5-[(4-methylpyrimidin-2-yl)amino]phenyl}-1,3-thiazol-2-yl)ethyl]cyclohexyl}methanesulfonamide;

ethyl 4-[1-hydroxy-1-(5-{3-methyl-5-[(4-methylpyrimidin-2-yl)amino]phenyl}-1,3-thiazol-2-yl)ethyl]-2-methylcyclohexanecarboxylate;

4-[1-hydroxy-1-(5-{3-methyl-5-[(4-methylpyrimidin-2-yl)amino]phenyl}-1,3-thiazol-2-yl)ethyl]-2-methylcyclohexanecarboxylic acid;

4-{1-hydroxy-1-[5-(3-methyl-5-{[4-(trifluoromethyl)pyrimidin-2-yl]amino}phenyl)-1,3-thiazol-2-yl]ethyl}-2-methylcyclohexanecarboxylic acid;

butyl 4-{1-hydroxy-1-[5-(3-methyl-5-{[4-(trifluoromethyl)pyrimidin-2-yl]amino}phenyl)-1,3-thiazol-2-yl]ethyl}cyclohexanecarboxylate;

1,4-dioxaspiro[4.5]dec-8-yl[5-(3-methyl-5-{[4-(trifluoromethyl)pyrimidin-2-yl]amino}phenyl)-1,3-thiazol-2-yl]methanol;

4-[1-hydroxy-1-(5-{3-methyl-5-[(4-methylpyrimidin-2-yl)amino]phenyl}-1,3-thiazol-2-yl)propyl]cyclohexanecarboxylic acid;

ethyl 4-{1-[5-(3-{[4-(difluoromethyl)pyrimidin-2-yl]amino}-5-methylphenyl)-1,3-thiazol-2-yl]-1-hydroxyethyl}-2-methyl cyclohexanecarboxylate;

4-{1-[5-(3-{[4-(difluoromethyl)pyrimidin-2-yl]amino}-5-methylphenyl)-1,3-thiazol-2-yl]-1-hydroxyethyl}-2-methylcyclohexanecarboxylic acid;

1,4-dioxaspiro[4.5]dec-8-yl[5-(3-methyl-5-{[4-(trifluoromethyl)pyrimidin-2-yl]amino}phenyl)-1,3-thiazol-2-yl]methanone;

ethyl 4-[1-(5-{3-[(5-fluoro-4-methoxypyrimidin-2-yl)amino]-5-methylphenyl}-1,3-thiazol-2-yl)-1-hydroxyethyl]-2-methylcyclohexanecarboxylate;

4-1-(5-{3-[(5-fluoro-4-methoxypyrimidin-2-yl)amino]-5-methylphenyl}-1,3-thiazol-2-yl)-1-hydroxyethyl]-2-methylcyclohexanecarboxylic acid;

4-[1-hydroxy-1-(5-{3-[(4-methoxypyrimidin-2-yl)amino]-5-methylphenyl}-1,3-thiazol-2-yl)ethyl]-2-methylcyclohexanecarboxylic acid;

3-[1-hydroxy-1-(5-{3-methyl-5-[(4-methylpyrimidin-2-yl)amino]phenyl}-1,3-thiazol-2-yl)ethyl]-2,2-dimethylcyclobutyl}acetic acid;

4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanol;

{3-[1-(5-{3-[(5-fluoro-4-methylpyrimidin-2-yl)amino]-5-methylphenyl}-1,3-thiazol-2-yl)-1-hydroxyethyl]-2,2-dimethylcyclobutyl}acetic acid;

4-hydroxy-4-{hydroxy[5-(3-methyl-5-{[4-(trifluoromethyl)pyrimidin-2-yl]amino}phenyl)-1,3-thiazol-2-yl]methyl}cyclohexanecarboxylic acid;

1-[4-(hydroxymethyl)cyclohexyl]-1-[5-(3-methyl-5-{[4-(trifluoromethyl)pyrimidin-2-yl]amino}phenyl)-1,3-thiazol-2-yl]ethanol;

ethyl 4-{1-hydroxy-1-[5-(3-methyl-5-{[4-(trifluoromethyl) pyrimidin-2-yl]amino}phenyl)-1,3-thiazol-2-yl] propyl}cyclohexanecarboxylate;

butyl 4-[1-hydroxy-1-(5-{3-methyl-5-[(4-methylpyrimidin-2-yl)amino]phenyl}-1,3-thiazol-2-yl)ethyl]cyclohexanecarboxylate;

4-[1-hydroxy-1-(5-{3-methyl-5-[(4-methylpyrimidin-2-yl) amino]phenyl}-1,3-thiazol-2-yl)ethyl]cyclohexanecarboxylic acid;

4-{1-hydroxy-1-[5-(3-methyl-5-{[4-(1-methylethyl)pyrimidin-2-yl]amino}phenyl)-1,3-thiazol-2-yl] ethyl}cyclohexanecarboxylic acid;

4-[1-(5-{3-[(4-cyclopropylpyrimidin-2-yl)amino]-5-methylphenyl}-1,3-thiazol-2-yl)-1-hydroxyethyl]cyclohexanecarboxylic acid;

4-[1-hydroxy-1-(5-{3-[(4-methoxypyrimidin-2-yl)amino]-5-methylphenyl}-1,3-thiazol-2-yl)ethyl]cyclohexanecarboxylic acid;

4-{1-hydroxy-1-[5-(3-methyl-5-{[4-(1-methylethoxy)pyrimidin-2-yl]amino}phenyl)-1,3-thiazol-2-yl] ethyl}cyclohexanecarboxylic acid;

4-[1-(5-{3-[(5-fluoro-4-methylpyrimidin-2-yl)amino]-5-methylphenyl}-1,3-thiazol-2-yl)-1-hydroxyethyl]cyclohexanecarboxylic acid;

4-[1-(5-{3-[(5-chloro-4-methylpyrimidin-2-yl)amino]-5-methylphenyl}-1,3-thiazol-2-yl)-1-hydroxyethyl]cyclohexanecarboxylic acid;

4-[1-(5-{3-[(5-fluoro-4-methoxypyrimidin-2-yl)amino]-5-methylphenyl}-1,3-thiazol-2-yl)-1-hydroxyethyl]cyclohexanecarboxylic acid;

4-[1-(5-{3-[(5-chloro-4-methoxypyrimidin-2-yl)amino]-5-methylphenyl}-1,3-thiazol-2-yl)-1-hydroxyethyl]cyclohexanecarboxylic acid;

butyl 4-[1-hydroxy-1-(5-{3-[(4-methoxypyrimidin-2-yl) amino]-5-methylphenyl}-1,3-thiazol-2-yl)ethyl]cyclohexanecarboxylate;

butyl 4-[1-(5-{3-[(5-fluoro-4-methoxypyrimidin-2-yl) amino]-5-methylphenyl}-1,3-thiazol-2-yl)-1-hydroxyethyl]cyclohexanecarboxylate;

butyl 4-[1-hydroxy-1-(5-{3-[(4-methylpyrimidin-2-yl) amino]phenyl}-1,3-thiazol-2-yl)ethyl]cyclohexanecarboxylate;

4-[1-hydroxy-1-(5-{3-[(4-methylpyrimidin-2-yl)amino] phenyl}-1,3-thiazol-2-yl)ethyl]cyclohexanecarboxylic acid;

butyl 4-{1-[5-(3-{[4-(difluoromethyl)pyrimidin-2-yl] amino}-5-methylphenyl)-1,3-thiazol-2-yl]-1-hydroxyethyl}cyclohexanecarboxylate;

4-{1-[5-(3-{[4-(difluoromethyl)pyrimidin-2-yl]amino}-5-methylphenyl)-1,3-thiazol-2-yl]-1-hydroxyethyl}cyclohexanecarboxylic acid;

4-{1-hydroxy-1-[5-(3-methyl-5-{[4-(trifluoromethyl)pyrimidin-2-yl]amino}phenyl)-1,3-thiazol-2-yl] propyl}cyclohexanecarboxylic acid;

4-{1-hydroxy-2-methyl-1-[5-(3-{[4-(trifluoromethyl)pyrimidin-2-yl]amino}phenyl)-1,3-thiazol-2-yl] propyl}cyclohexanecarboxylic acid;

4-{1-hydroxy-2-methyl-1-[5-(3-methyl-5-{[4-(trifluoromethyl)pyrimidin-2-yl]amino}phenyl)-1,3-thiazol-2-yl] propyl}cyclohexanecarboxylic acid;

4-{1,2-dihydroxy-1-[5-(3-methyl-5-{[4-(trifluoromethyl) pyrimidin-2-yl]amino}phenyl)-1,3-thiazol-2-yl] ethyl}cyclohexanecarboxylic acid;

4-[2,2,2-trifluoro-1-hydroxy-1-(5-{3-methyl-5-[(4-methylpyrimidin-2-yl)amino]phenyl}-1,3-thiazol-2-yl)ethyl] cyclohexanecarboxylic acid;

4-[1,2-dihydroxy-1-(5-{3-methyl-5-[(4-methylpyrimidin-2-yl)amino]phenyl}-1,3-thiazol-2-yl)ethyl]cyclohexanecarboxylic acid;

benzyl {4-[1-hydroxy-1-(5-{3-methyl-5-[(4-methylpyrimidin-2-yl)amino]phenyl}-1,3-thiazol-2-yl)ethyl] cyclohexyl}carbamate;

4-{1-hydroxy-1-[5-(3-methyl-5-{[4-(trifluoromethyl)pyrimidin-2-yl]amino}phenyl)-1,3-thiazol-2-yl] ethyl}cyclohexanecarbonitrile;

4-{1-methoxy-1-[5-(3-methyl-5-{[4-(trifluoromethyl)pyrimidin-2-yl]amino}phenyl)-1,3-thiazol-2-yl] ethyl}cyclohexanecarboxylic acid;

4-{2-hydroxy-1-[5-(3-methyl-5-{[4-(trifluoromethyl)pyrimidin-2-yl]amino}phenyl)-1,3-thiazol-2-yl] ethyl}cyclohexanecarboxylic acid;

4-{amino[5-(3-methyl-5-{[4-(trifluoromethyl)pyrimidin-2-yl]amino}phenyl)-1,3-thiazol-2-yl] methyl}cyclohexanecarboxylic acid;

4-[3,4-dihydroxy-1-(5-{3-methyl-5-[(4-methylpyrimidin-2-yl)amino]phenyl}-1,3-thiazol-2-yl)butyl]cyclohexanecarboxylic acid;

4-[1-hydroxy-1-(5-{3-methyl-5-[(4-methylpyrimidin-2-yl) amino]phenyl}-1,3-thiazol-2-yl)ethyl]cyclohexanecarbonitrile;

2-[2-{1-hydroxy-1-[5-(3-methyl-5-{[4-(trifluoromethyl)pyrimidin-2-yl]amino}phenyl)-1,3-thiazol-2-yl] ethyl}cyclopropyl]-2-methylpropanoic acid;

3-{1-hydroxy-1-[5-(3-methyl-5-{[4-(trifluoromethyl)pyrimidin-2-yl]amino}phenyl)-1,3-thiazol-2-yl]ethyl}bicyclo [3.1.0]hexane-6-carboxylic acid;

3-{1-hydroxy-1-[5-(3-methyl-5-{[4-(trifluoromethyl)pyrimidin-2-yl]amino}phenyl)-1,3-thiazol-2-yl] ethyl}cyclopentanecarboxylic acid;

4-{fluoro[5-(3-methyl-5-{[4-(trifluoromethyl)pyrimidin-2-yl]amino}phenyl)-1,3-thiazol-2-yl] methyl}cyclohexanecarboxylic acid;

1-[5-(3-methyl-5-{[4-(trifluoromethyl)pyrimidin-2-yl] amino}phenyl)-1,3-thiazol-2-yl]-[4-(2H-tetrazol-5-yl)cyclohexyl]ethanol;

1-(5-{3-methyl-5-[(4-methylpyrimidin-2-yl)amino]phenyl}-1,3-thiazol-2-yl)-1-[4-(2H-tetrazol-5-yl)cyclohexyl] ethanol;

4-{1-hydroxy-1-[5-(3-methyl-5-{[4-(trifluoromethyl)pyrimidin-2-yl]amino}phenyl)-1,3-thiazol-2-yl] ethyl}cyclohexanecarboxylic acid;

4-{cyclopropyl(hydroxy) [5-(3-methyl-5-{[4-(trifluoromethyl)pyrimidin-2-yl]amino}phenyl)-1,3-thiazol-2-yl] methyl}cyclohexanecarboxylic acid;

4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanecarboxylic acid;

4-{1-fluoro-1-[5-(3-methyl-5-{[4-(trifluoromethyl)pyrimidin-2-yl]amino}phenyl)-1,3-thiazol-2-yl] ethyl}cyclohexanecarboxylic acid;

4-hydroxy-4-[(5-{3-methyl-5-[(4-methylpyrimidin-2-yl) amino]phenyl}-1,3-thiazol-2-yl)methyl]cyclohexanecarboxylic acid;

1-[5-(3-methyl-5-{[4-(trifluoromethyl)pyrimidin-2-yl] amino}phenyl)-1,3-thiazol-2-yl]-1-[4-(2H-tetrazol-5-yl) cyclohexyl]ethanol 4-{hydroxy[5-(3-methyl-5-{[4-(trifluoromethyl)pyrimidin-2-yl]amino}phenyl)-1,3-thiazol-2-yl] methyl}cyclohexanecarboxamide;

4-[1-(5-{2-bromo-3-methyl-5-[(4-methylpyrimidin-2-yl) amino]phenyl}-1,3-thiazol-2-yl)-1-hydroxyethyl]cyclohexanecarboxylic acid;

4-{2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid;
3,3-dimethyl-4-{[5-(3-methyl-5-{[4-(trifluoromethyl)pyrimidin-2-yl]amino}phenyl)-1,3-thiazol-2-yl]carbonyl}cyclohexanone
4-{hydroxy[5-(3-methyl-5-{[4-(trifluoromethyl)pyrimidin-2-yl]amino}phenyl)-1,3-thiazol-2-yl]methyl}-3,3-dimethylcyclohexanol;
4-[(5-{3-methyl-5-[(4-methylpyrimidin-2-yl)amino]phenyl}-1,3-thiazol-2-yl)methyl]cyclohexanecarboxylic acid;
Methyl (1,3-cis, 1,4-trans)-3-hydroxy-2,2-dimethyl-4-{[5-(3-methyl-5-{[4-(trifluoromethyl)pyrimidin-2-yl]amino}phenyl)-1,3-thiazol-2-yl]carbonyl}cyclopentanecarboxylate;
4-[1-hydroxy-1-{5-[3-(hydroxymethyl)-5-{[4-(trifluoromethyl)pyrimidin-2-yl]amino}phenyl]-1,3-thiazol-2-yl]ethyl}cyclohexanecarboxylic acid;
4-{1-[5-(3-cyclopropyl-5-{[4-(trifluoromethyl)pyrimidin-2-yl]amino}phenyl)-1,3-thiazol-2-yl]-1-hydroxyethyl}cyclohexanecarboxylic acid;
4-{1-[5-(3-fluoro-5-{[4-(trifluoromethyl)pyrimidin-2-yl]amino}phenyl)-1,3-thiazol-2-yl]-1-hydroxyethyl}cyclohexanecarboxylic acid;
4-(1-{5-[3-(difluoromethyl)-5-{[4-(trifluoromethyl)pyrimidin-2-yl]amino}phenyl]-1,3-thiazol-2-yl}-1-hydroxyethyl)cyclohexanecarboxylic acid.

In the application, various terms are as defined below:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Carbocycle" refers to a non-aromatic saturated or partially unsaturated monocyclic ring in which all ring atoms are carbon, and the ring being isolated or fused (including ortho-fused, spiro-fused and bridged) to one or two such rings or to a benzene ring. In the case of a polycyclic carbocycle, the attachment point may be on any ring. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-6}$ cycloalkyl" refers to a saturated ring ring having from 3 to 6 ring carbon atoms. Exemplary "cycloalkyl" groups useful in the present invention include, but are not limited to, cyclopropyl, cyclobutyl, cyclopentyl and cyclohexyl.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Analogously, the term "fluoroalkyl" refers to an alkyl group as defined above in which one and up to all hydrogen atoms are replaced by fluorine. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl. Examples of "fluoroalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one $R^7$ substituents on the "A" ring, each substituent is independently selected at each occurrence, and each substituent can be the same or different from the other(s).

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula I or a salt, solvate or physiologically functional derivative thereof.

As used herein, the term "solvate" refers to a complex of variable stoichiometry formed by a solute (in this invention, a compound of formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula I may have the ability to crystallize in more than one form, a characteristic known as polymorphism, and it is understood that such polymorphic forms ("polymorphs") are within the scope of formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of formula I may contain asymmetric or chiral centers, and, therefore, exist in different stereoisomeric forms. It is intended that all stereoisomeric forms of the compounds of formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of formula I may be atropisomers (e.g., substituted biaryls) and are considered as part of this invention.

It is also noted that the compounds of formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base addition salts.

A pharmaceutically acceptable acid addition salt can be formed by reaction of a compound of formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula I can comprise or be, for example, a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of formula I, such as when the compounds are present as mono- or di-hydrates, or mono- or dihydrochlorides.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula I can be prepared without undue experimentation by conventional techniques well known to those skilled in the art or by processes analogous to those described in the Schemes and Examples herein using appropriate isotopically-enriched reagents and/or intermediates The compounds of formula I and salts, solvates and physiologically functional derivatives thereof are believed to be inhibitors of Syk activity, and thus be potentially useful in the treatment of diseases and conditions associated with inappropriate Syk activity.

Compound of formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula I or a pharmaceutically acceptable salt, solvate, or a physiologically functional derivative thereof.

In a further embodiment, the present invention provides for the use of a compound of formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) singaling, B cell receptor signaling, T cell receptor singaling and is an essential component of integrin beta (1), beta (2), and beta (3) signaling in neutrophils. Thus, compounds of the present invention can be used to regulate Fc receptor, ITAM, B cell receptor and integrin singaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler® (Schering Corp.), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
| --- | --- |
| Compound of formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of formula I | 25 |
| Microcrystalline Cellulose | 415 |

| Tablet | mg/tablet |
| --- | --- |
| Providone | 14.0 |
| Pregelatinized Starch | 43.5 |
| Magnesium Stearate | 2.5 |
| | 500 |

| Capsule | mg/capsule |
| --- | --- |
| Compound of formula I | 25 |
| Lactose Powder | 573.5 |
| Magnesium Stearate | 1.5 |
| | 600 |

| Inhalation Aerosol | Per dose |
| --- | --- |
| Compound of formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
| --- | --- |
| Compound of formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula I for the treatment of diseases or conditions associated with inappropriate Syk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula I or a pharmaceutically acceptable salt or solvate thereof, or a physiologically functional derivative thereof, and the use of at least one other pharmaceutically active agent. The compound(s) of formula I and the other pharmaceutically active agent(s) may be administered together or separately and, when administered separately this may occur simultaneously or sequentially in any order. The amounts of the compound(s) of formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)—glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol). fumarate).salmeterol or a pharmaceutically acceptable salt thereof (e.g., salmeterol xinafoate) and fluticasone propionate.

For the treatment of treatment cancer a compound of formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonylgumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl] methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl) methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235, 708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamfiatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-mannoheptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:

Biological Assay

Homogeneous Time-Resolved Fluorescence (HTRF) Assay for the Recombinant Human Syk Enzyme:

A recombinant GST-hSyk fusion protein was used to measure potency of compounds to inhibit human Syk activity. The recombinant human GST-Syk (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 μM final concentration). Final volume of the reaction was 10 μL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% Tween 20. Final volume of the quenching solution was 10 μL. The resulting HTRF signal was measured after 30 minutes on a EnVision (Perkin-Elmer) reader using a time-resolved fluorescence protocol. $IC_{50}$ was determined following 10-dose titration (10 μM to 0.508 nM) and four parameter logistic curve fitting using the Merck Assay Data Analyzer. The rhSyk activity ($IC_{50}$) is expressed as +++(100 nM or less), ++(between 100 and 1000 nM), +(between 1 and 10 μM). $IC_{50}$ values are also provided for the following representative compounds:

| Example | rhSyk (nM) |
| --- | --- |
| Example 1 (faster eluting isomer) | <0.5 |
| Example 1 (slower eluting enantiomer) | 2 |
| 1-3 | 1 |
| 1-11 | 3 |
| 1-18 | <0.5 |
| 2-1 | <0.5 |
| 2-3 | 1258 |
| 2-16 | 93 |
| 2-52 | 1 |
| 2-53 | 13 |
| 2-57 | 123 |
| 2-60 | 5 |
| 2-73 | 1460 |
| 2-74 | 1429 |

-continued

| Example | rhSyk (nM) |
| --- | --- |
| 2-77 | <0.5 |
| 2-79 | 2 |
| 2-101 | 2 |
| 2-109 | 15 |
| 2-110 | 1 |
| 2-112 | 3 |
| 2-114 | 1 |
| 3-2 | 2 |
| 4-6 | 2 |
| Example 5, Step 3 (trans isomer) | 318 |
| 6-3 | 5 |
| Example 7 (trans isomer) | 35 |
| Example 13, step 2 | 301 |
| Example 14 | 850 |
| Example 15 | <0.5 |
| Example 16 | 1 |
| Example 17 | 1 |
| Example 18 | <0.5 |
| Example 22 | 197 |

The compounds of this invention may be made by a variety of methods, including standard chemistry. Illustrative general synthetic methods are set out below and then specific compounds of the invention are prepared in the Examples. Any previously defined variable will continue to have the previously defined meaning unless otherwise indicated.

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of formula I. Those skilled in the art will recognize if a stereocenter exists in compounds of formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)=t-butyloxycarbonyl; BOP=(Benzotriazol-1-yloxy)-tris(dimethylamino)phosphonium hexafluorophosphate; DAST=(Diethylamino)sulfur trifluoride; dba=dibenzylideneacetone; DCE=1,2-dichloroethane; DCM=Dichloromethane; Dibal/Dibal-H=Diisobutylaluminum hydride; DIPEA/DIEA=Diisopropylethylamine; DMAP=N,N-dimethyl-aminopyridine; DME=1,2-dimethoxyethane; DMF=Dimethyl formamide; DMSO=Dimethylsulfoxide; Dppf=1,1'-Bis (diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl) uronium hexafluorophosphate; HMDS=Hexamethyldisilazane; HOBT=1-Hydroxybenzotriazole; HPLC=high pressure liquid chromatography; IPA=Isopropyl alcohol; LDA=Lithium diisopropylamide; mCPBA=Meta-chloroperoxybenzoic acid; Ms=Methanesulfonyl (mesyl); MTBE=Methyl t-butyl ether; NBS=N-bromosuccinimide; Ph=phenyl; SFC=supercritical fluid chromatography; TBAF=t-butylammonium fluoride; TBDMS/TBS=t-butyl dimethylsilyl; TFA=Trifluoroacetic/ trifluoroacetate; THF=Tetrahydrofuran; TLC=Thin-layer chromatography; TMS=Trimethylsilyl; Ts=Toluenesulfonyl (tolyl); TSA=p-toluenesulfonic acid. Abbreviations for alkyl/ cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

SCHEME 1

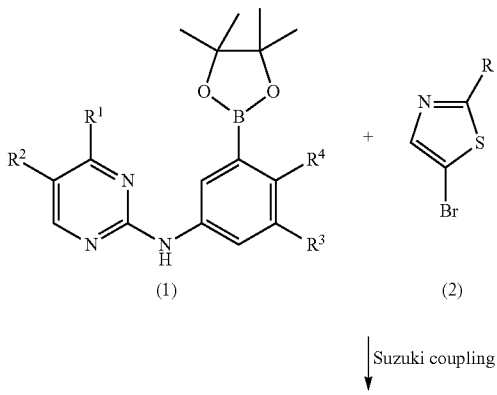

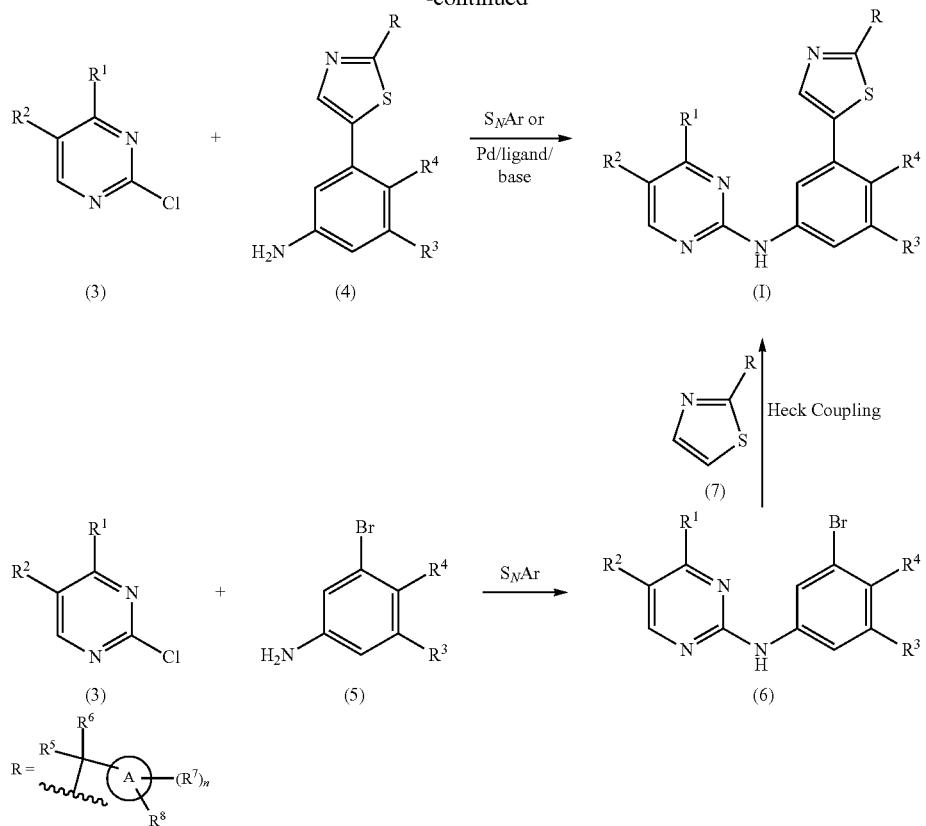

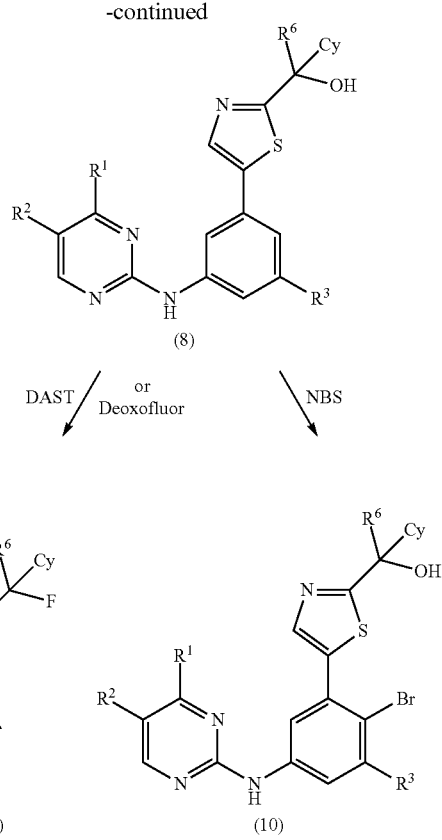

Compounds of formula I may be prepared by Suzuki coupling of boronic esters (1) with a thiazole bromide (2). Boronic esters (1) can be obtained by reacting 2-chloropyrimidines (3) and 3-bromoanilines (5) to form the corresponding N-(3-bromophenyl)-pyrimidine-2-amines (6), followed by Miyaura coupling with bis(pinacolato)diboron. Compounds of formula I can also be obtained by reacting 2-chloropyrimidines (3) and thiazole-substituted anilines (4) in the presence of a Pd catalyst or alternatively an S$_N$Ar reaction. Thiazole-substituted anilines (4), in turn, may be formed under Suzuki coupling conditions using a bromothiazole and nitrophenyl boronic ester, followed by reduction of the nitro group to an amino group using standard conditions known to reduce nitroaromatic compounds to anilines, such as Pd-catalyzed hydrogenation. Compounds of formula I may also be formed by Heck reaction between bromo-substituted anilines (6) with substituted thiazoles (7). Bromo-substituted anilines (6) can be prepared by S$_N$Ar reaction between 2-chloropyrimidines (3) and substituted bromo-anilines (5).

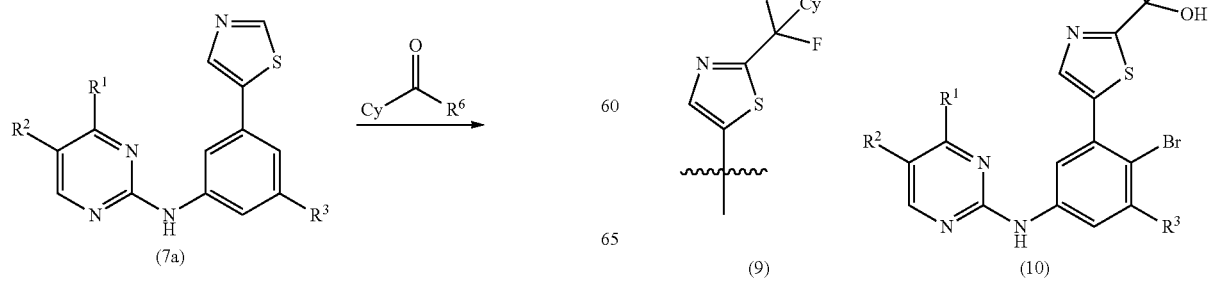

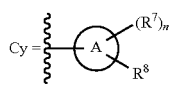

Compounds of formula (7a) can be deprotonated with LDA, and the addition of a carbonyl containing compound yields the alcohol (8). The alcohol (8) can be converted to the fluoride (9) with a fluorinating agent, such as DAST. Alternatively, bromination of (8) with NBS yields (10).

SCHEME 3

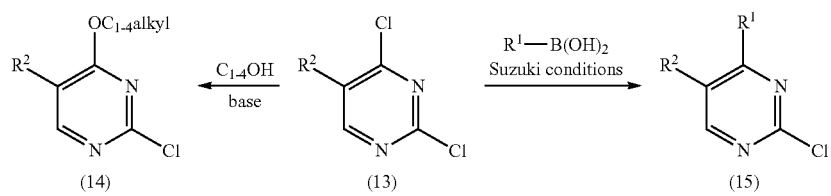

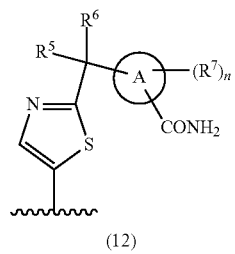

Carboxylic acids, such as (11), can be converted to the amide (12) with amines and standard amide coupling reagents.

SCHEME 4

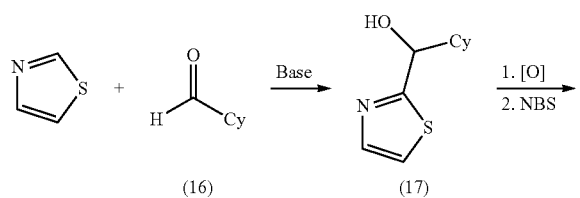

Preparation of 2-chloropyrimidine building blocks starting with 2,4-dichloropyrimidine (13) is illustrated in scheme 4. Pyrimidine functionalization via Suzuki coupling yields substituted 2-chloropyrimidines (15), while a base mediated $S_NAr$ reaction with substituted alcohol nucleophile provides ethers (14).

Preparation of various thiazole building blocks is illustrated in Schemes 5, 6 and 7.

SCHEME 5

As depicted in Scheme 5, deprotonation of thiazole followed by the addition of the aldehyde (16) yields the alcohol (17). Oxidation of the alcohol (17) followed by bromination with NBS yields (18). Nucleophilic addition to the ketone (18) gives the substituted alcohol (19). Alternatively, reductive amination of the ketone (18) affords amines (20).

SCHEME 6

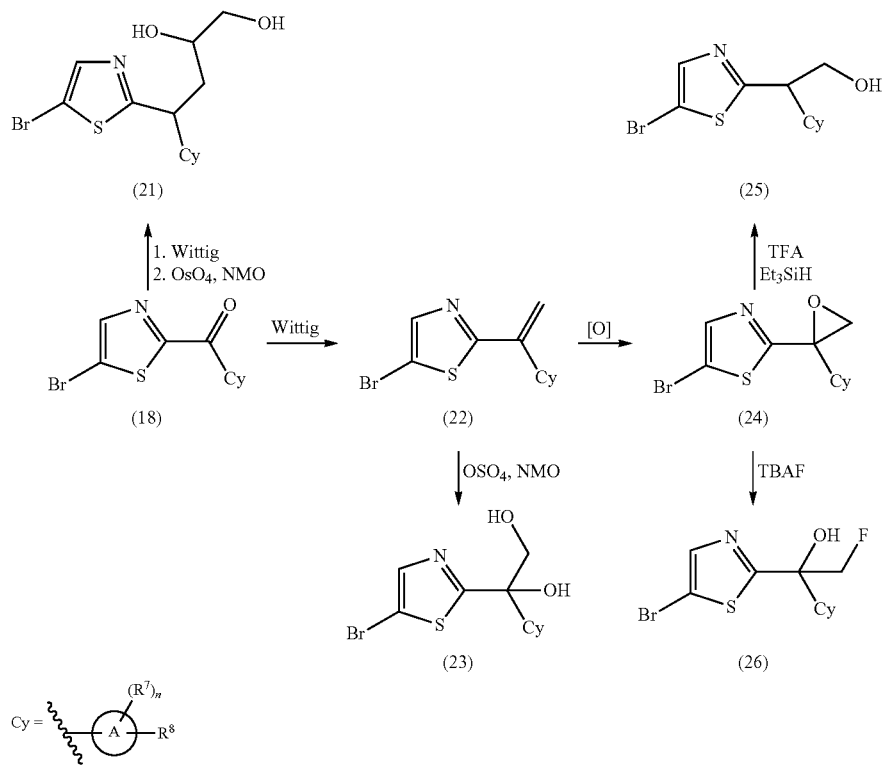

As illustrated in Scheme 6, ketone (18) can be converted to the diol (21) by a Wittig reaction followed by dihydroxylation. Alternatively, (18) can be converted to the 1,1'-disubstituted olefin (22) via a Wittig reaction. Dihydroxylation of the olefin (22) yields the diol (23), while oxidation of (22) gives the epoxide (24). Opening of the epoxide (24) with TFA and triethylsilane yields the primary alcohol (25) while opening with TBAF yields (26).

As illustrated in Scheme 7, reaction of primary bromide (27) with triethylphosphite yields (28). Deprotonation of 28 with sodium hydride followed by ketone addition yields the substituted olefin (29). Dihydroxylation of the olefin (29) leads to the diol (30).

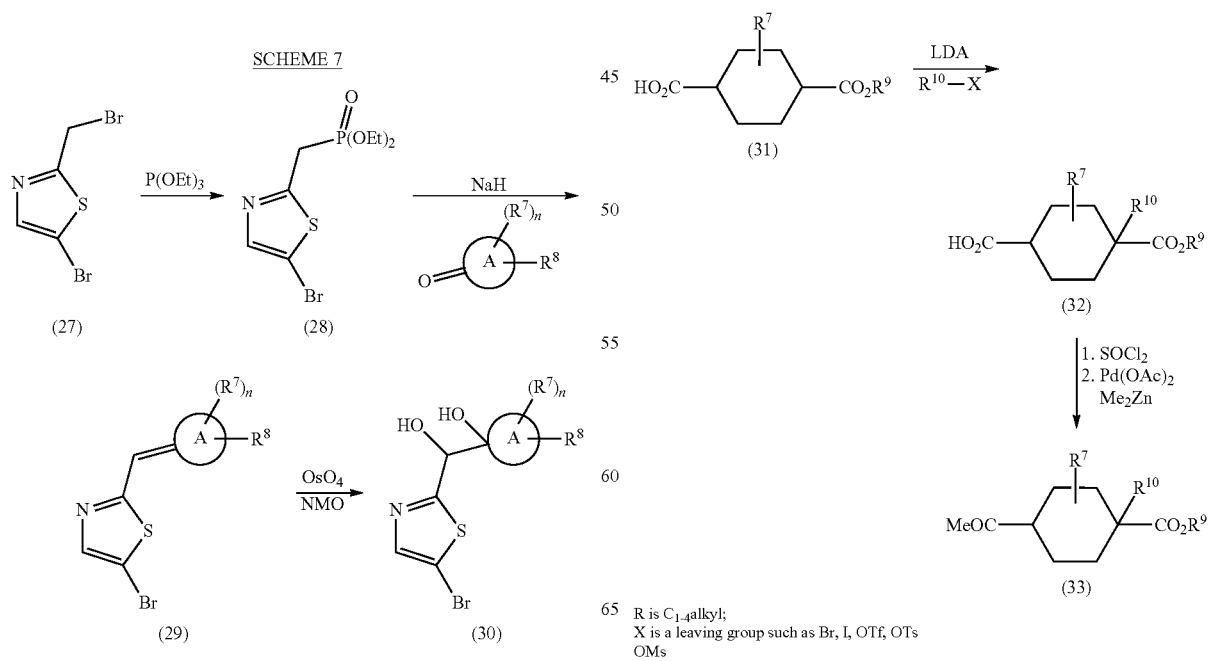

R is $C_{1-4}$alkyl;
X is a leaving group such as Br, I, OTf, OTs OMs

Preparation of substituted cyclohexyl derivatives is illustrated in Scheme 8. α-Alkylation of (31) yields (32). The carboxylic acid (32) can be converted to the acyl chloride with thionyl chloride. Immediate reaction with Pd(OAc)$_2$ and dimethylzinc yields the ketone (33) which can be used as shown in Scheme 2.

Compounds of formula I can be prepared according to the procedures described in the Schemes and Examples herein, using appropriate materials and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

INTERMEDIATE 1

3-methyl-5-(1,3-thiazol-5-yl)aniline

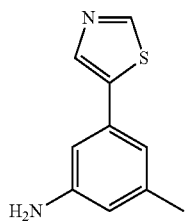

Step 1: Dioxane (720 mL) in a 1 L three-necked round bottom flask was degassed for 30 min. 3-Bromo-5-methylaniline (60 g, 193 mmol), (bispinacolato)diboron (96 g, 377 mmol), potassium acetate (42.7 g, 435 mmol), X-Phos (8.3 g, 17.41 mmol) and Pd$_2$dba$_3$ (3.99 g, 4.35 mmol) were added to the degassed solvent under N$_2$(g). After stirring for 10 min at room temperature, the reaction mixture was heated to an internal temperature of 80° C. After ca. 4 hours, the heating mantle was removed and replaced with an ice water bath. The reaction mixture was cooled to 30° C., and was then filtered through a pad of CELITE (washing with 500 mL of MTBE). This was transferred to a 4 L separatory funnel containing 500 mL pH 8 phosphate buffer, 500 mL brine, and an additional 500 mL of MTBE. The layers were separated and the organic layer was washed with 1 L of a 1:1 v:v mixture of brine and water. The aqueous layers were combined and sequentially back extracted with a second 500 mL portion of MTBE. The combined organics were treated with 100 g of MgSO$_4$ and the resulting mixture stirred for 20 min. The resulting suspension was then filtered and concentrated in vacuo. The resultant residue was purified by chromatography on silica gel (0-25% ethyl acetate in hexanes) to yield 3-methyl-5-(4,4,5,5-tetramethyl-1,3,2-dioxaborolan-2-yl)aniline as a light orange solid. MS ESI: [M+H]$^+$ m/z 234.

Step 2: 3-Methyl-5-(4,4,5,5-tetramethyl-1,3,2-dioxaborolan-2-yl)aniline (20.98 g, 90 mmol), 5-bromothiazole (8.85 mL, 99 mmol) and sodium carbonate (90 mL, 180 mmol) were combined in a flask. 2-Methyl-THF (326 mL) was added and the mixture was degassed with N$_2$ for 1.5 h before 1,1'-bis(diphenylphosphino)ferrocene-palladium(II)dichloride dichloromethane complex (3.67 g, 4.50 mmol) was added. The reaction was heated to 100° C. overnight and was then cooled to room temperature. The reaction mixture was filtered though a pad of CELITE, washing with ethyl acetate. The layers were separated and the aqueous layer was back-extracted with ethyl acetate, dried over Na$_2$SO$_4$, and concentrated. The residue was purified by chromatography on silica gel (0-40% ethyl acetate in hexanes). 3-Methyl-5-(1,3-thiazol-5-yl)aniline was isolated as a yellowish brown solid. MS ESI: [M+H]$^+$ m/z 191. $^1$H NMR (500 MHz, CDCl$_3$) δ 8.71 (s, 1H), 8.02 (s, 1H), 6.80 (s, 1H), 6.71 (s, 1H), 6.50 (s, 1H), 3.71 (s, 2H), 1.79 (s, 3H).

INTERMEDIATE 2

4-cyclopropyl-5-fluoro-N-[3-methyl-5-(1,3-thiazol-5-yl)phenyl]-pyrimidin-2-amine Step 1: 5-Fluoro-2,4-dichloropyrimidine (5 g, 29.9 mmol), cyclopropyl boronic acid (2.57 g, 29.9 mmol), potassium phosphate tribasic (15.89 g, 74.9 mmol) and PdCl$_2$(dppf)-dichloromethane adduct (1.22 g, 1.50 mmol) were added to a dry flask. The flask was degassed with argon and then tetrahydrofuran (150 ml) was added. The reaction mixture was degassed with argon for five minutes, and then heated to 67° C. After 12 hours, the reaction mixture was cooled to room temperature, diluted with ethyl acetate (1000 mL), washed with brine, dried over magnesium sulfate, filtered and concentrated. The residue was purified by flash chromatography on silica gel (EtOAc/hexane gradient) to afford 2-chloro-4-cyclopropyl-5-fluoropyrimidine. MS ESI: [M+H]$^+$ m/z 172.9. $^1$H NMR (500 MHz, DMSO-d$_6$) δ 8.66 (d, J=2.0 Hz, 1H); 2.34-2.26 (m, 1H); 1.26-1.20 (m, 2H); 1.12-1.08 (m, 2H).

Step 2: 3-Methyl-5-(1,3-thiazol-5-yl)aniline (0.250 g, 1.31 mmol), the product of Step 1 (0.227 g, 1.31 mmol), palladium (II) acetate (0.0295 g, 0.131 mmol), xantphos (0.114 g, 0.197 mmol), and cesium carbonate (0.856 g, 2.63 mmol) were added to a dry flask. The flask was degassed with argon and then dioxane (4.4 ml) was added. The reaction mixture was degassed with argon for 5 minutes, and then heated to 100° C. After 2 hours, the reaction mixture was cooled to room temperature, diluted with ethyl acetate, washed with brine, dried over magnesium sulfate, filtered, and concentrated. The residue was purified by flash chromatography on silica gel (EtOAc/dichloromethane gradient) to afford 4-cyclopropyl-5-fluoro-N-[3-methyl-5-(1,3-thiazol-5-yl)phenyl]pyrimidin-2-amine. MS ESI: [M+H]$^+$ m/z 327. $^1$H NMR (500 MHz, DMSO-d$_6$) δ 9.59 (s, 1H); 9.06 (s, 1H); 8.38 (d, J=2.5 Hz, 1H); 8.19 (s, 1H); 7.94 (s, 1H); 7.39 (s, 1H); 7.10 (s, 1H); 2.29 (s, 3H); 2.28-2.23 (m, 1H); 1.18-1.14 (m, 4H).

INTERMEDIATE 3 methyl (1S,3R)-3-acetyl-2,2-dimethylcyclobutanecarboxylate

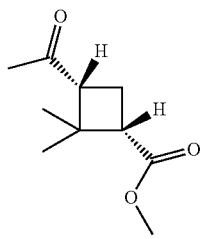

Step 1: (−)-Verbenone (615 mg, 4.09 mmol) was dissolved in a mixture of acetonitrile (2.0 mL), $CCl_4$ (2.0 mL) and water (3.0 mL). Sodium periodate (3.59 g, 16.79 mmol) and ruthenium(III) chloride hydrate (18.68 mg, 0.090 mmol) were added and the resulting biphasic mixture was stirred vigorously at room temperature for 24 hrs. The reaction mixture was then diluted with DCM, washed with $H_2O$ and extracted with DCM (3×). The combined organic layers were dried ($Na_2SO_4$), filtered and concentrated under reduced pressure to give (1R,3S)-3-acetyl-2,2-dimethylcyclobutanecarboxylic acid as a pale yellow oil, which was used without further purification. MS ESI calc'd. for $C_9H_{15}O_3$ [M+H]$^+$ 171. found 171.

Step 2: Acetyl chloride (1.02 ml, 14.32 mmol) was added dropwise to MeOH (10 mL) at 0° C. and the resulting mixture was stirred at 0° C. for 30 mins. (1R,3S)-3-acetyl-2,2-dimethylcyclobutanecarboxylic acid from Step 1 (696 mg, 4.09 mmol) was added as a solution in MeOH (2 mL) and the reaction mixture was stirred overnight while warming up to room temperature. The volatiles were then removed under reduced pressure and the residue was purified by flash chromatography on silica gel (gradient elution, 2% to 20% EtOAc in Hexanes) to give methyl (1R,3S)-3-acetyl-2,2-dimethylcyclobutanecarboxylate as a colorless oil. MS ESI calc'd. for $C_{10}H_{17}O_3$ [M+H]$^+$ 185. found 185. $^1$H NMR (500 MHz, $CDCl_3$) δ 3.66 (s, 3H), 2.88 (dd, J=10.5, 7.6 Hz, 1H), 2.78 (dd, J=10.8, 8.1 Hz, 1H), 2.64 (app q, J=10.8 Hz, 1H), 2.06 (s, 3H), 1.92-1.87 (m, 1H), 1.43 (s, 3H), 0.89 (s, 3H).

INTERMEDIATE 4 methyl 2-(2-acetylcyclopropyl)-2-methylpropanoate

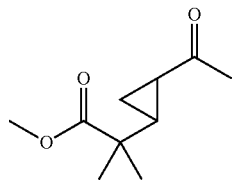

Step 1: To a solution of dimethyl (2-oxopropyl)phosphonate (4.09 mL, 30.0 mmol) in tetrahydrofuran (200 mL) at 0° C. was added potassium tert-butoxide (3.22 g, 28.7 mmol). After 15 minutes the reaction mixture was moved to room temperature, and after an additional 15 minutes methyl 2,2-dimethyl-3-oxopropanoate (3.39 g, 26.0 mmol) was added. The opaque reaction mixture was stirred for 21 hours and then partitioned between diethyl ether (100 ml) and water (100 mL). The layers were separated and the aqueous layer was extracted with diethyl ether (100 mL, 50 mL). The combined organic layers were washed with aqueous saturated sodium bicarbonate solution and brine, dried over sodium sulfate, filtered, and concentrated under reduced pressure. The residue was purified by chromatography on silica gel (0-4% methanol/dichloromethane) to yield methyl (3E)-2,2-dimethyl-5-oxohex-3-enoate. $^1$H NMR (500 MHz, $CDCl_3$) δ 6.95 (d, J=16.4 Hz, 1H), 6.09 (d, J=16.4 Hz, 1H), 3.71 (s, 3H), 2.29 (s, 3H), 1.37 (s, 6H).

Step 2: A solution of trimethylsulfoxium iodide (506 mg, 2.297 mmol) and potassium tert-butoxide (258 mg, 2.297 mmol) in dimethylsulfoxide (6 mL) was stirred for 1.5 hours and then transferred via syringe to a solution of methyl (3E)-2,2-dimethyl-5-oxohex-3-enoate (340 mg, 1.998 mmol) in tetrahydrofuran (6 mL). The reaction mixture was stirred for 14 hours and then partitioned between diethyl ether (25 mL) and a 5:1 v:v mixture of water:saturated aqueous sodium bicarbonate solution (12 mL). The layers were separated and the aqueous layer was extracted with diethyl ether (20 mL, 10 mL). The combined organics were washed with water (3×10 mL) and brine (10 mL), dried over sodium sulfate, filtered, and concentrated under reduced pressure to afford methyl 2-(2-acetylcyclopropyl)-2-methylpropanoate which was carried on without further purification. MS ESI calc'd. for $C_{10}H_{17}O_3$ [M+H]$^+$ 185. found 185.

INTERMEDIATE 5 ethyl 3-acetylbicyclo[3.1.0]hexane-6-carboxylate

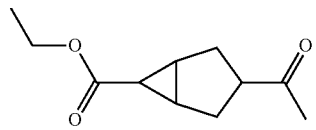

A solution of ethyl diazoacetate (0.266 mL, 2.179 mmol) in dichloromethane (6 mL) was added over 6 hours via syringe pump to a solution of 1-(cyclopent-3-en-1-yl)ethanone (200 mg, 1.816 mmol) and rhodium(II) acetate dimer (16.1 mg, 0.036 mmol) in dichloromethane (6 mL). After an additional 11 hours, the reaction mixture was concentrated under reduced pressure. The residue was purified by chromatography on silica gel (10-30% ethyl acetate/hexanes) to afford ethyl 3-acetylbicyclo[3.1.0]hexane-6-carboxylate. MS ESI calc'd. for $C_{11}H_{17}O_3$ [M+H]$^+$ 197. found 197.

INTERMEDIATE 6

2-chloro-4-difluoromethyl-pyrimidine

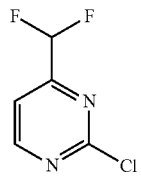

To a solution of difluoroacetic anhydride (50 g, 287 mmol) in $CH_2Cl_2$ (300 mL) cooled to −20° C. was added DMAP (0.351 g, 2.87 mmol) followed by the addition of ethyl vinyl ether (13.8 mL, 144 mmol) at such a rate that the internal temperature did not exceed −10° C. After the addition was complete, the flask was stirred at 0° C. for 12 h before slowly warming to room temperature over 6 h. Water along with CH$_2$Cl$_2$ were added, the layers separated and the organic washed sequentially with aqueous saturated NaHCO$_3$ and then brine. The organic layer was dried with MgSO$_4$, filtered, concentrated in vacuo. The residue was subsequently taken up in EtOH (162 mL), immersed in an ice water bath and then urea (17.25 g, 287 mmol) was added followed by the addition of conc. HCl (43 mL) at such a rate that the internal temperature did not exceed 20° C. When the addition was complete, the cooling bath was removed and the resulting mixture stirred for 18 h before concentration in vacuo. EtOH was added and the mixture concentrated a second time, then EtOAc was added and the mixture was concentrated again (2×). The residue was diluted with EtOAc (100 mL) and the resulting heterogenous mixture stirred for 10 min and then the solvent decanted. This was repeated twice more, then the light brown solid was collected via filtration and dried under vacuum for 48 h before dilution with phosphous oxychloride (215 mL, 2310 mmol). The resulting suspension was heated to 105° C. for 90 min during which time it was observed to become homogenous. The reaction mixture was cooled to room temperature, poured carefully into a 4 L cooled flask containing 2 L of ice and a temperature probe. The mixture was stirred for 1 h until the exotherm had ceased at which time the contents were transferred to a separatory funnel with additional CH$_2$Cl$_2$. The layers were separated and the aqueous layer extracted with CH$_2$Cl$_2$ (2×), then the combined organics were dried with MgSO$_4$, filtered and concentrated in vacuo (200 Torr, 40° C.) to an orange oil. The product was placed under vacuum for 1 min to yield 2-chloro-4-difluoromethyl-pyrimidine as a 62.5 wt % solution in CH$_2$Cl$_2$ as judged by $^1$H NMR). $^1$H NMR (600 MHz, CDCl$_3$) δ 8.82 (d, J=5.0, 1H), 7.57 (d, J=5.0, 1H), 6.51 (t, J=54.4, 1H).

INTERMEDIATE 7

2-chloro-4-(propan-2-yloxy)pyrimidine

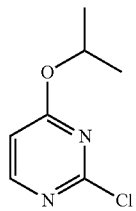

To a solution of 2,4-dichloropyrimidine (5.0 g, 34 mmol) in 2-propanol (84 mL) was added Cs$_2$CO$_3$ (12 g, 37 mmol) and the mixture was stirred at rt for 16 h. The reaction was then heated to 65° C. for 3 h, after which time the reaction was filtered and concentrated. Purification on silica gel using a gradient solvent system of 0-10% EtOAc/Hexanes furnished 2-chloro-4-(propan-2-yloxy)pyrimidine as a colorless oil. $^1$H NMR (500 MHz, CDCl$_3$) δ 8.23 (d, J=5.7, 1H), 6.56 (d, J=5.7, 1H), 5.38 (hept, J=6.2, 1H), 1.34 (d, J=6.2, 6H).

INTERMEDIATE 8

N-[3-methyl-5-(4,4,5,5-tetramethyl-1,3,2-dioxaborolan-2-yl)phenyl]-4-(trifluoromethyl)pyrimidin-2-amine

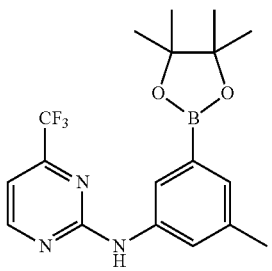 [SMILES: Cc1cc(Nc2nccc(C(F)(F)F)n2)cc(B2OC(C)(C)C(C)(C)O2)c1]

Step 1: A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with 2 L of water, then adjusted to pH 7-8 with aqueous saturated sodium bicarbonate solution, followed by extraction with EtOAc (2×2 L). The organic layers were combined, washed with water (2×2 L), dried over anhydrous sodium sulfate and concentrated in vacuo to afford N-(3-bromo-5-methylphenyl)-4-(trifluoromethyl)pyrimidin-2-amine as a light yellow solid. MS ESI calc'd for C$_{12}$H$_{10}$BrF$_3$N$_3$ [M+H]$^+$ 332, 334. found 332, 334. $^1$H NMR (400 MHz, CDCl$_3$): δ 8.68 (d, J=4.9 Hz, 1H), 7.79 (s, 1H), 7.33-7.23 (m, 2H), 7.10-7.06 (m, 2H), 2.36 (s, 3H).

Step 2: To a solution of N-(3-bromo-5-methylphenyl)-4-(trifluoromethyl)pyrimidin-2-amine (250 g, 753.01 mmol) in 1,4-dioxane (3 L) were added 4,4,5,5-tetramethyl-2-(4,4,5,5-tetramethyl-1,3,2-dioxaborolan-2-yl)-1,3,2-dioxaborolane (225 g, 885.83 mmol), KOAc (225 g, 2.30 mol) and Pd(dppf)Cl$_2$ (19 g, 25.23 mmol). The resulting solution was heated to reflux overnight. The solid was filtered and the filtrate was decolorized by passing through a silica gel column. The fractions were collected and concentrated in vacuo. This resulted in a portion of purified product and a portion of crude product. The crude product was decolorized again with active carbon to provide an additional aliquot of product. The two portions of purified product were combined to afford N-[3-methyl-5-(4,4,5,5-tetramethyl-1,3,2-dioxaborolan-2-yl)phenyl]-4-(trifluoromethyl)pyrimidin-2-amine as a white solid. MS ESI calc'd for C$_{18}$H$_{22}$BF$_3$N$_3$O$_2$ [M+H]$^+$ 380. found 380. $^1$H NMR (400 MHz, CDCl$_3$) δ 8.61 (d, J=5.2, 1H), 7.75 (s, 1H), 7.64 (s, 1H), 7.40-7.30 (m, 2H), 7.00 (d, J=5.2, 1H), 2.39 (s, 3H), 1.35 (s, 12H).

INTERMEDIATE 9

5-fluoro-4-methoxy-N-[3-methyl-5-(4,4,5,5-tetramethyl-1,3,2-dioxaborolan-2-yl)phenyl]pyrimidin-2-amine

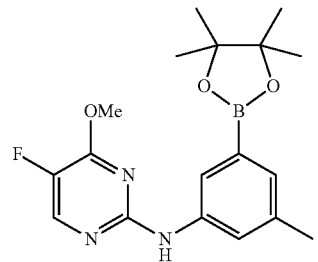 [SMILES: COc1nc(Nc2cc(C)cc(B3OC(C)(C)C(C)(C)O3)c2)ncc1F]

To a flask containing 2-chloro-5-fluoro-4-methoxypyrimidine (0.32 g, 1.97 mmol) and 3-methyl-5-(4,4,5,5-tetramethyl-1,3,2-dioxaborolan-2-yl)aniline (0.40 g, 1.72 mmol) were added dioxane (17 mL) and methanesulfonic acid (0.13 mL, 1.97 mmol). The reaction was heated at 100° C. overnight. The reaction was then cooled to room temperature, diluted with ethyl acetate, washed with water, dried over magnesium sulfate, filtered and concentrated. Flash chromatography was used for purification to yield 5-fluoro-4-methoxy-N-[3-methyl-5-(4,4,5,5-tetramethyl-1,3,2-dioxaborolan-2-yl)phenyl]pyrimidin-2-amine. MS ESI calc'd for C$_{18}$H$_{24}$BFN$_3$O$_3$ [M+H]$^+$ 360. found 360. $^1$H NMR (500

MHz, DMSO-$d_6$) δ 9.51 (s, 1H), 8.27 (d, J=3.2, 1H), 8.00 (s, 1H), 7.57 (s, 1H), 7.07 (s, 1H), 4.01 (s, 3H), 2.25 (s, 3H), 1.26 (s, 12H).

The following intermediates were prepared using the route shown in Intermediate 8 or Intermediate 9. In some cases, the acid used in the $S_NAR$ reaction was changed.

| Intermediate | Structure | Route Used | [M + H]+ obs'd |
|---|---|---|---|
| 10 | 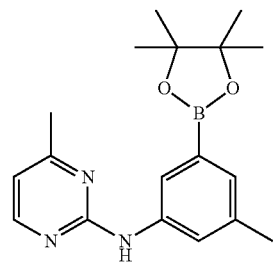 [SMILES: Cc1cc(Nc2nccc(C)n2)cc(B2OC(C)(C)C(C)(C)O2)c1] | Analogous to Intermediate 8 | 326 |
| 11 | 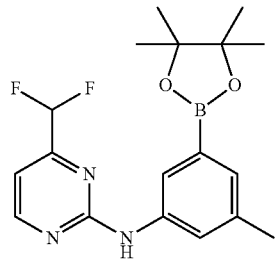 | Analogous to Intermediate 8 | 362 |
| 12 | 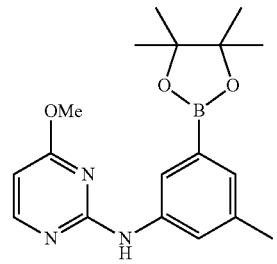 [SMILES: COc1ccnc(Nc2cc(C)cc(B3OC(C)(C)C(C)(C)O3)c2)n1] | Analogous to Intermediate 8 | 342 |
| 13 | 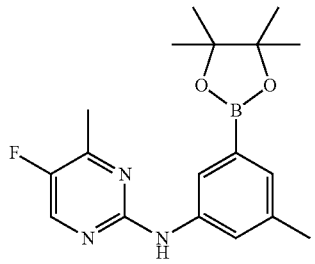 [SMILES: Cc1cc(Nc2ncc(F)c(C)n2)cc(B2OC(C)(C)C(C)(C)O2)c1] | Analogous to Intermediate 9 | 344 |
| 14 | 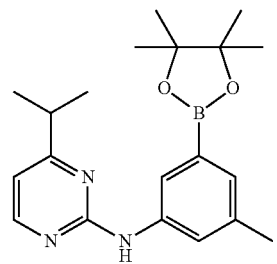 [SMILES: Cc1cc(Nc2nccc(C(C)C)n2)cc(B2OC(C)(C)C(C)(C)O2)c1] | Analogous to Intermediate 9 | 354 |

-continued

| Intermediate | Structure | Route Used | [M + H]+ obs'd |
|---|---|---|---|
| 15 | (4-cyclopropylpyrimidin-2-yl)-NH-(3-methyl-5-(pinacolboronate)phenyl) | Analogous to Intermediate 8 | 352 |
| 16 | (4-isopropoxypyrimidin-2-yl)-NH-(3-methyl-5-(pinacolboronate)phenyl) | Analogous to Intermediate 9 | 370 |
| 17 | (5-chloro-4-methylpyrimidin-2-yl)-NH-(3-methyl-5-(pinacolboronate)phenyl) | Analogous to Intermediate 9 | 360 |
| 18 | (5-chloro-4-methoxypyrimidin-2-yl)-NH-(3-methyl-5-(pinacolboronate)phenyl) | Analogous to Intermediate 9 | 376 |
| 19 | (4-methylpyrimidin-2-yl)-NH-(3-(pinacolboronate)phenyl) | Analogous to Intermediate 9 | 312 |
| 20 | (4-cyclopropyl-5-fluoropyrimidin-2-yl)-NH-(3-methyl-5-(pinacolboronate)phenyl) | Analogous to Intermediate 9 | 370 |

INTERMEDIATE 21

N-[3-methyl-5-(1,3-thiazol-5-yl)phenyl]-4-(trifluoromethyl)pyrimidin-2-amine

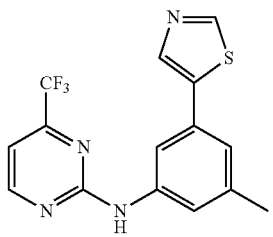 [SMILES: Cc1cc(Nc2nccc(C(F)(F)F)n2)cc(-c2cncs2)c1]

To a solution of N-[3-methyl-5-(4,4,5,5-tetramethyl-1,3,2-dioxaborolan-2-yl)phenyl]-4-(trifluoromethyl)pyrimidin-2-amine (80 g, 211.08 mmol) in 1,4-dioxane (800 mL) was added 5-bromo-1,3-thiazole (28 g, 171.78 mmol), Pd(dppf)Cl$_2$ (8 g, 10.62 mmol) and a solution of sodium carbonate (44.7 g, 421.70 mmol) in water (447 mL). The resulting solution was heated to reflux for 1 hour. Then it was allowed to cool to room temperature and was concentrated in vacuo. The residue was diluted with EtOAc (500 mL) and filtered. The filtrate was washed with brine (2×300 mL) and water (2×300 mL). The organic layer was dried over anhydrous sodium sulfate and concentrated in vacuo. The crude product was recrystallized from EtOAc:DCM in the ratio of 1:5 to afford a portion of product. The mother liquor was applied onto a silica gel column and eluted with dichloromethane/ethyl acetate (2:1) to afford N-[3-methyl-5-(1,3-thiazol-5-yl)phenyl]-4-(trifluoromethyl)pyrimidin-2-amine as a pale yellow solid. MS ESI calc'd for C$_{15}$H$_{12}$F$_3$N$_4$S [M+H]$^+$ 337. found 337. $^1$H NMR (400 MHz, CD$_3$COCD$_3$) δ 9.21 (1H, s), 8.97 (1H, s), 8.84 (1H, d, J=4.8 Hz), 8.21 (2H, m), 7.64 (1H, s), 7.25-7.26 (2H, m), 2.41 (3H, s). rhSyk activity=+++.

INTERMEDIATES 22 ethyl (1S,2R,4S)-4-[1(R)-(5-bromo-1,3-thiazol-2-yl)-1-hydroxyethyl]-2-methyl cyclohexanecarboxylate; ethyl (1S,2R,4S)-4-[1 (S)-(5-bromo-1,3-thiazol-2-yl)-1-hydroxyethyl]-2-methyl cyclohexanecarboxylate; ethyl (1R,2S,4R)-4-[1(R)-(5-bromo-1,3-thiazol-2-yl)-1-hydroxyethyl]-2-methylcyclohexanecarboxylate; ethyl (1R,2S,4R)-4-[1(S)-(5-bromo-1,3-thiazol-2-yl)-1-hydroxyethyl]-2-methylcyclohexanecarboxylate

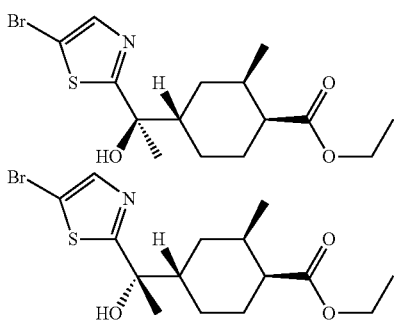

-continued

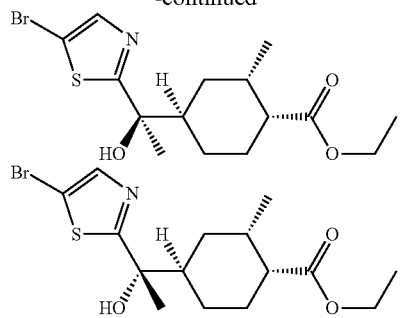

Step 1: To a cooled (0° C.) solution of (methoxymethyl)triphenylphosphonium chloride (55.8 g, 163 mmol) in THF (250 mL) was added KOtBu (1 M in THF, 163 mL, 163 mmol) at such a rate that the internal temperature did not exceed 5° C. When the addition was complete, the resulting mixture was stirred for 1 h at which point ethyl (1,2-cis)-2-methyl-4-oxo-cyclohexanecarboxylate (20 g, 109 mmol) was introduced as a solution in THF (200 mL). The reaction mixture was allowed to warm slowly to room temperature and stirred for 18 h. The vessel was then immersed in an ice bath and water (100 mL) was added followed by 6N HCl (250 mL). The cooling bath was removed and the reaction stirred until hydrolysis was complete by TLC (~2 h) at which point it was diluted with water and EtOAc. The layers were separated, the organics dried with MgSO4, filtered, and concentrated in vacuo to afford ethyl (1,2-cis)4-formyl-2-methylcyclohexanecarboxylate (23 g) as a mixture of isomers. This colorless oil was used directly in the subsequent step without further manipulation.

Step 2: To a 500 mL round bottom flask was added iPrMgCl-LiCl (1.3 M in THF, 92 mL, 119 mmol) and the solution cooled in an ice bath. Thiazole (8.9 mL, 125 mmol) was then introduced at such a rate that the internal temperature did not exceed 5° C. and then the thick slurry was stirred for 1 h. 100 mL of THF was introduced and the reaction mixture cooled to −50° C. at which point ethyl (1,2-cis)-4-formyl-2-methylcyclohexanecarboxylate (mixture of isomers, 23 g) was added as a solution in THF (100 mL) via cannula. When complete, the reaction mixture was permitted to warm slowly to 5° C., stirred for 30 min and then quenched by the addition of water and EtOAc. The layers were separated, the organic mixture dried with MgSO4, filtered and concentrated in vacuo to afford ethyl (1,2-cis)-4-[hydroxy(1,3-thiazol-2-yl)methyl]-2-methylcyclohexanecarboxylate (34 g) as a mixture of isomers. This brown oil was used directly in the subsequent step without further manipulation.

Step 3: The crude mixture of ethyl (1,2-cis)-4-[hydroxy(1,3-thiazol-2-yl)methyl]-2-methylcyclohexanecarboxylate (34 g) was diluted with DMF (200 mL) and NBS (21.2 g, 119 mmol) was added. The resulting mixture was heated to 55° C., stirred until the starting materials were consumed and the heating mantle was then removed. Water (220 mL) containing sodium sulfite (10 g) was added followed by EtOAc. The layers were separated, the organics washed a second time with water, then dried with MgSO4, filtered and concentrated in vacuo. The crude residue was absorbed on silica and purified by flash chromatography to afford ethyl (1,2-cis)-(1,4-trans)-4-[(5-bromo-1,3-thiazol-2-yl)(hydroxy)methyl]-2-methylcyclohexane carboxylate as a yellow oil (1:1 mixture of diastereomers at secondary alcohol stereocenter) and ethyl (1,2-cis)-(1,4-cis)-4-[(5-bromo-1,3-thiazol-2-yl)(hydroxy)

methyl]-2-methylcyclohexanecarboxylate as a yellow oil (3:2 mixture of diastereomers at secondary alcohol stereocenter).

Step 4:

Ethyl (1,2-cis)-(1,2-trans)-4-[(5-bromo-1,3-thiazol-2-yl)(hydroxy)methyl]-2-methylcyclohexane carboxylate (16.0 g, 44.2 mmol) was diluted with $CH_2Cl_2$ (160 mL) and immersed in a room temperature water bath. To this was added Dess-Martin periodinane (20.6 g, 48.6 mmol) resulting in a noticeable exotherm. After 60 min, an aqueous solution of 5% $NaHCO_3$ and 5% sodium sulfite was added and the resulting biphasic mixture stirred until both layers were clear at which point they were separated, the aqueous layer back extracted with $CH_2Cl_2$ and the combined organics dried with $MgSO_4$, filtered and concentrated in vacuo. The crude residue was absorbed on silica and purified by flash chromatography on silica gel to afford ethyl (1,2-cis)-(1,4-trans)-4-[(5-bromo-1,3-thiazol-2-yl)carbonyl]-2-methylcyclohexanecarboxylate as a light yellow oil. MS ESI calc'd. for $C_{14}H_{19}BrNO_3S$ [M+H]$^+$ 360. found 360.

Step 5: Ethyl (1,2-cis)-(1,4-trans)-4-[(5-bromo-1,3-thiazol-2-yl)carbonyl]-2-methylcyclohexane carboxylate (6.7 g, 18.7 mmol) was diluted with THF (67 mL) and cooled in a dry ice/acetone bath. To this solution was added MeMgBr (3 M in $Et_2O$, 6.23 mL, 18.7 mmol) at such a rate that the internal temperature did not exceed −60° C. Following this addition, the reaction mixture was stirred for 1 h at ≤60° C.) then diluted with water, then EtOAc and additional water. The layers were separated and the aqueous layer was re-extracted with EtOAc. The combined organics were dried with $MgSO_4$, filtered and concentrated in vacuo. The crude residue was absorbed on silica gel and purified by flash chromatography to afford ethyl (1,2-cis)-(1,4-trans)4-[1-(5-bromo-1,3-thiazol-2-yl)-1-hydroxyethyl]-2-methylcyclohexane carboxylate as a light yellow oil of a 1:1 mixture of diasteromers that were then separated by chiral SFC to afford all four stereoismoers: ethyl (1S,2R,4S)-4-[(1R)-1-(5-bromo-1,3-thiazol-2-yl)-1-hydroxyethyl]-2-methylcyclohexanecarboxylate, ethyl (1S,2R,4S)-4-[(1S)-1-(5-bromo-1,3-thiazol-2-yl)-1-hydroxyethyl]-2-methylcyclohexane carboxylate, ethyl (1R,2S,4R)-4-[(1R)-1-(5-bromo-1,3-thiazol-2-yl)-1-hydroxyethyl]-2-methylcyclohexanecarboxylate, and ethyl (1R,2S,4R)-4-[(1S)-1-(5-bromo-1,3-thiazol-2-yl)-1-hydroxyethyl]-2-methylcyclohexanecarboxylate. MS ESI calc'd. for $C_{15}H_{23}BrNO_3S$ [M+H]+376, 378. found 376, 378.

INTERMEDIATE 23 cis-methyl-3-acetylcyclopentanecarboxylate

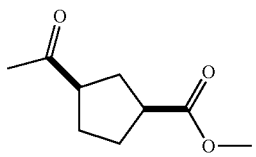

Step 1: To a solution of cis-3-(methoxycarbonyl)cyclopentanecarboxylic acid (2 g, 11.62 mmol) in DCM (20 ml) was added DMF (0.05 mL) followed by dropwise addition of oxalyl chloride (1.118 ml, 12.78 mmol). The reaction mixture was stirred at room temperature for 2 hrs after gas evolution ceased. The volatiles were then removed under reduced pressure and the oily residue was used without further purification in the following step.

Step 2: A solution of methyllithium (1.6 M in $Et_2O$, 55.2 ml, 88 mmol) was added dropwise to a suspension of copper (I) iodide (8.85 g, 46.5 mmol) in THF (97 ml) at 0° C. After being stirred at room temperature for 10 min, the mixture was cooled to −78° C. and the crude acid chloride from Step 1 (2.215 g, 11.62 mmol) was added dropwise as a solution in THF (1 mL). The reaction mixture was stirred for 30 mins at −78° C., quenched with MeOH and allowed to warm up to room temperature. Saturated aq. $NH_4Cl$ was added and the mixture was extracted with $Et_2O$. The organic layer was separated, washed with brine, dried over $Na_2SO_4$ and concentrated under reduced pressure. The residue was purified by $SiO_2$ gel (gradient elution 10% to 80% $Et_2O$ in Hexanes) to give cis-methyl-3-acetylcyclopentanecarboxylate as a colorless oil. MS ESI calc'd. for $C_9H_{15}O_3$ [M+H]$^+$ 171. found 171. $^1$H NMR (500 MHz, $CDCl_3$) δ 3.68 (s, 3H), 2.93-2.85 (m, 1H), 2.84-2.78 (m, 1H), 2.20-2.14 (m, 4H), 2.07-2.01 (m, 1H), 1.95-1.89 (m, 4H).

INTERMEDIATE 24 ethyl trans-4-[(5-bromo-1,3-thiazol-2-yl)carbonyl]cyclohexanecarboxylate

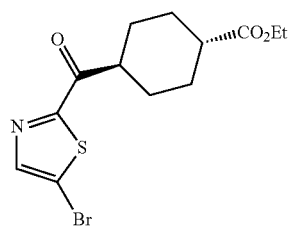 [SMILES: CCOC(=O)[C@H]1CC[C@H](C(=O)c2ncc(Br)s2)CC1]

Step 1: To a cooled (0° C.) solution of (methoxymethyl)triphenylphosphonium chloride (60.4 g, 176 mmol) in THF (250 mL) was added KOtBu (1 M in THF, 176 mL, 176 mmol) at such a rate that the internal temperature did not exceed 5° C. When the addition was complete, the resulting mixture was stirred for 1 h at which point ethyl 4-oxocyclohexanecarboxylate (20 g, 118 mmol) was introduced as a solution in THF (200 mL). The reaction mixture was allowed to warm slowly to room temperature where it was stirred for 18 h. The vessel was then immersed in an ice bath and water (100 mL) was added followed by 6N HCl (250 mL). The cooling bath was removed and the reaction stirred until hydrolysis was complete by TLC (~2 h) at which point it was diluted with water and EtOAc. The layers were separated, the organics dried with $MgSO_4$, filtered, and concentrated in vacuo to afford ethyl 4-formylcyclohexanecarboxylate (23 g) as a 3:2 mixture of trans:cis isomers. This colorless oil was used directly in the subsequent step without further manipulation.

Step 2: To a 500 mL round bottom flask was added iPrMgCl-LiCl (1.3 M in THF, 99 mL, 129 mmol) and the solution cooled in an ice bath. Thiazole (9.7 mL, 135 mmol) was then introduced at such a rate that the internal temperature did not exceed 5° C. and then the thick slurry was stirred for 1 h. 100 mL of THF was introduced and the reaction mixture cooled to −50° C. at which point ethyl 4-formylcyclohexanecarboxylate (23 g) was added as a solution in THF (100 mL) via cannula. When complete the reaction mixture was permitted to warm slowly to 5° C. where it was stirred for 30 min then quenched by the addition of water and EtOAc. The layers were separated, the organic mixture dried with $MgSO_4$, filtered and concentrated in vacuo to afford ethyl 4-[hydroxy(1,3-thiazol-2-yl)methyl]cyclohexanecarboxylate as a 3:2 mixture of trans:cis isomers both of which are racemic mixtures. This brown oil was used directly in the subsequent step without further manipulation.

Step 3: The crude mixture of ethyl 4-[hydroxy(1,3-thiazol-2-yl)methyl]cyclohexanecarboxylate (34 g) was diluted with DMF (220 mL) and NBS (23 g, 129 mmol) was added. The resulting mixture was heated to 55° C. and stirred until the starting materials were consumed, at which point the heating mantle was removed. Water (220 mL) containing sodium sulfite (10 g) was added followed by EtOAc. The layers were separated, the organics washed a second time with water, then dried with MgSO$_4$, filtered and concentrated in vacuo. The crude residue was absorbed on silica and purified by flash chromatography to afford racemic ethyl trans-4-[(5-bromo-1,3-thiazol-2-yl)(hydroxy)methyl]cyclohexanecarboxylate as a white solid and racemic ethyl cis-4-[(5-bromo-1,3-thiazol-2-yl)(hydroxy)methyl]cyclohexanecarboxylate as a yellow oil. Characterization data for the trans isomer: MS ESI calc'd. for C$_{13}$H$_{19}$BrNO$_3$S [M+H]$^+$ 348, 350. found 348, 350. $^1$H NMR (600 MHz, CDCl$_3$) δ 7.53 (d, J=4.3, 1H), 4.66 (d, J=5.0, 1H), 4.06 (q, J=7.1, 2H), 2.20-2.16 (m, 1H), 1.97 (d, J=13.3, 2H), 1.80-1.72 (m, 2H), 1.68 (d, J=12.6, 1H), 1.43-1.31 (m, 2H), 1.25-1.13 (m, 5H).

Step 4: Ethyl trans-4-[(5-bromo-1,3-thiazol-2-yl)(hydroxy)methyl]cyclohexanecarboxylate (11.5 g, 33 mmol) was diluted with CH$_2$Cl$_2$ (115 mL) and immersed in a room temperature water bath. To this was added Dess-Martin periodinane (15.4 g, 36.3 mmol) resulting in a noticeable exotherm. After 30 min, an aqueous solution of 5% NaHCO$_3$ and 5% sodium sulfite was added and the resulting biphasic mixture stirred until both layers were clear. The layers were separated, the aqueous layer back extracted with CH$_2$Cl$_2$ and the combined organics dried with MgSO$_4$, filtered and concentrated in vacuo. The crude residue was absorbed on silica and purified by flash chromatography to afford ethyl trans-4-[(5-bromo-1,3-thiazol-2-yl)carbonyl]cyclohexane-carboxylate (11.1 g, 32 mmol) as a yellow oil. MS ESI calc'd. for C$_{13}$H$_{17}$BrNO$_3$S [M+H]$^+$ 346, 348. found 346, 348. $^1$H NMR (600 MHz, CDCl$_3$) δ 7.82 (s, 1H), 4.14-4.03 (m, 2H), 3.53-3.41 (m, 1H), 2.35-2.21 (m, 1H), 2.15-1.96 (m, 4H), 1.61-1.43 (m, 4H), 1.21 (t, J=7.1, 3H).

INTERMEDIATE 25

N-{trans-4-[1-(5-bromo-1,3-thiazol-2-yl)-1-hydroxyethyl]cyclohexyl}-methanesulfonamide

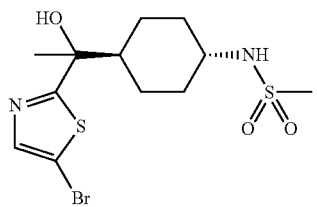 [SMILES: CC(O)(c1ncc(Br)s1)[C@H]1CC[C@H](NS(C)(=O)=O)CC1]

Step 1: To a solution of benzyl {trans-4-[methoxy(methyl)carbamoyl]cyclohexyl}carbamate (3.43 g, 10.71 mmol) in THF (107 mL) at 0° C. was added methylmagnesium bromide (3.0 M in diethyl ether, 5.35 mL, 16.06 mmol) and the reaction was stirred for one hour at 0° C. An additional portion of methylmagnesium bromide (3.0 M in diethyl ether, 5.35 mL, 16.06 mmol) was then added and the reaction was allowed to warm to room temperature and then stirred for one hour. The reaction was slowly quenched with aqueous saturated ammonium chloride. Water and ethyl acetate were added and the organic layer was separated, dried over magnesium sulfate, filtered and concentrated to afford benzyl (trans-4-acetylcyclohexyl)carbamate that was used without further purification.

Step 2: To a solution of thiazole (740 mg, 8.72 mmol) in THF (87 mL) at −78° C. was added n-BuLi (2.5 M in hexanes, 3.84 mL, 9.59 mmol) and the solution was stirred for 30 minutes at −78° C. A solution of benzyl (trans-4-acetylcyclohexyl)carbamate (1.20 g, 4.36 mmol) in THF (5 mL) was added and the reaction was stirred for one hour at −78° C. The reaction was diluted with water and warmed to room temperature. The mixture was extracted with ethyl acetate and the organic layer was separated, dried over magnesium sulfate, filtered and concentrated in vacuo. Column chromatography on silica gel (0-10% methanol gradient in dichloromethane) afforded benzyl {trans-4-[1-hydroxy-1-(1,3-thiazol-2-yl)ethyl]cyclohexyl}carbamate MS ESI calc'd. for C$_{19}$H$_{25}$N$_2$O$_3$S [M+H]$^+$ 361. found 361. $^1$H NMR (500 MHz, DMSO-d$_6$) δ 7.67 (d, J=3.2, 1H), 7.51 (d, J=3.2, 1H), 7.40-7.20 (m, 4H), 7.12 (d, J=8.0, 1H), 5.70 (s, 1H), 4.95 (s, 2H), 3.19-2.98 (m, 1H), 1.88-1.66 (m, 3H), 1.65-1.49 (m, 1H), 1.47-1.33 (m, 4H), 1.28-1.14 (m, 1H), 1.14-0.89 (m, 3H).

Step 3: To a solution of benzyl {trans-4-[1-hydroxy-1-(1,3-thiazol-2-yl)ethyl]cyclohexyl}-carbamate (895 mg, 2.48 mmol) in dichlormethane at −78° C. was added boron tribromide (1.0 M in dichloromethane, 2.7 mL, 2.7 mmol) dropwise. After one hour, the solution was warmed to 0° C. Another portion of boron tribromide (1.0 M in dichloromethane, 2.7 mL, 2.7 mmol) was then added dropwise and the reaction was allowed to warm to room temperature. The solution was then carefully diluted with methanol and concentrated in vacuo. The residue was purified by chromatography on silica gel to afford 1-(trans-4-aminocyclohexyl)-1-(1,3-thiazol-2-yl)ethanol. MS ESI calc'd. for C$_{11}$H$_{19}$N$_2$OS [M+H]$^+$ 227. found 227. $^1$H NMR (500 MHz, DMSO-d$_6$) δ 7.67 (d, J=3.3, 1H), 7.51 (d, J=3.2, 1H), 5.69 (s, 1H), 2.46-2.39 (m, 1H), 1.80-1.65 (m, 3H), 1.63-1.50 (m, 1H), 1.43 (s, 3H), 1.40-1.32 (m, 1H), 1.24-1.11 (m, 1H), 1.03-0.86 (m, 3H).

Step 4: To a solution of 1-(trans-4-aminocyclohexyl)-1-(1,3-thiazol-2-yl)ethanol (100 mg, 0.44 mmol) in dichlormethane (2.9 mL) and triethylamine (0.31 mL, 2.21 mmol) at 0° C. was added methanesulfonyl chloride (34 μL, 0.44 mmol) and the reaction was allowed to stir for 10 minutes at 0° C. and then diluted with water, dichloromethane and aqueous saturated sodium bicarbonate. The organic layer was separated, dried over magnesium sulfate, filtered and concentrated in vacuo. The residue was purified by column chromatography on silica gel (0-100% ethyl acetate gradient in hexanes) to afford N-{trans-4-[1-hydroxy-1-(1,3-thiazol-2-yl)ethyl]cyclohexyl}methanesulfonamide. MS ESI calc'd. for C$_{12}$H$_{21}$N$_2$O$_3$S$_2$ [M+H]$^+$ 305. found 305. $^1$H NMR (500 MHz, CDCl$_3$) δ 7.70 (d, J=3.2, 1H), 7.28 (d, J=3.2, 1H), 4.25-4.14 (m, 1H), 3.30-3.13 (m, 1H), 2.95 (s, 3H), 2.18-2.09 (m, 1H), 2.09-2.02 (m, 2H), 1.96-1.88 (m, 1H), 1.80-1.69 (m, 1H), 1.64-1.53 (m, 3H), 1.40-1.28 (m, 1H), 1.28-1.13 (m, 3H).

Step 5: To a solution of N-{trans-4-[1-hydroxy-1-(1,3-thiazol-2-yl)ethyl]cyclohexyl}methanesulfonamide (178 mg, 0.59 mmol) in DMF (4.0 mL) was added N-bromosuccinimide (104 mg, 0.585 mmol) and the reaction was heated at 50° C. for one hour. The reaction was then cooled to room temperature and another portion of N-bromosuccinimide (52 mg, 0.292 mmol) was added. The reaction was then heated at 50° C. for one hour. The solution was then cooled to room temperature and diluted with water and ethyl acetate. The organic layer was separated, dried over magnesium sulfate, filtered and concentrated in vacuo. The residue was purified by column chromatography on silica gel to afford N-{trans-4-[1-(5-bromo-1,3-thiazol-2-yl)-1-hydroxyethyl] cyclohexyl}methanesulfonamide. MS ESI calc'd. for $C_{12}H_{20}N_2O_3S_2$ [M+H]$^+$ 383, 385. found 383, 385. $^1$H NMR (500 MHz, DMSO-d$_6$) δ 7.73 (s, 1H), 6.91 (d, J=7.4, 1H), 5.95 (s, 1H), 2.99-2.87 (m, 1H), 2.54 (s, 3H), 1.94-1.72 (m, 4H), 1.52 (t, J=11.9, 1H), 1.47-1.39 (m, 4H), 1.30-0.92 (m, 3H).

INTERMEDIATE 26 trans-4-acetylcyclohexanecarbonitrile

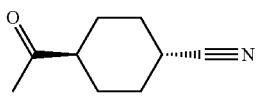

Step 1: To a solution of trans-4-cyanocyclohexanecarboxylic acid (1.29 g, 8.42 mmol) in dichloromethane (7.7 mL) was added thionyl chloride (2.0 M in dichloromethane, 10.11 mL, 20.21 mmol) and the reaction was heated at 38° C. overnight. Then, the reaction was concentrated to afford trans-4-cyanocyclohexanecarbonyl chloride that was used in the next step without further purification.

Step 2: To the product from step 1 (1.44 g, 8.42 mmol) was added dioxane (56 mL) and the solution was degassed via subsurface bubbling with argon for 30 minutes. Pd(OAc)$_2$ (95 mg, 0.42 mmol) was added and argon was bubbled through the solution for 15 minutes. Dimethylzinc (2.0 M in toluene, 4.21 mL, 8.42 mmol) was added and the solution was evacuated and then purged with argon 5 times. The reaction was heated overnight at 38° C. The mixture was then cooled to room temperature, diluted carefully with water and ethyl acetate, filtered through a pad of CELITE and washed with ethyl acetate. The organic layer of the filtrate was then dried over magnesium sulfate, filtered and concentrated in vacuo. The residue was purified by column chromatography on silica gel to afford trans-4-acetylcyclohexanecarbonitrile. $^1$H NMR (500 MHz, CDCl$_3$) δ 2.52-2.32 (m, 2H), 2.23-2.12 (m, 5H), 2.07-1.93 (m, 2H), 1.72-1.53 (m, 2H), 1.48-1.33 (m, 2H).

INTERMEDIATE 27 trans-ethyl 4-[1-(5-bromo-1,3-thiazol-2-yl)-1-hydroxypropyl]-cyclohexanecarboxylate

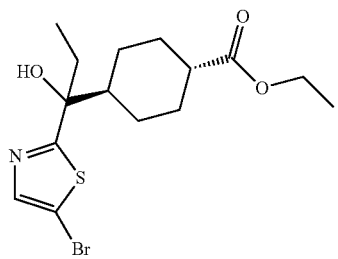 [SMILES: CCOC(=O)[C@H]1CC[C@H](C(O)(CC)c2ncc(Br)s2)CC1]

A solution of ethyl trans-4-[(5-bromo-1,3-thiazol-2-yl) carbonyl]cyclohexanecarboxylate (500 mg, 1.444 mmol) in THF (6 mL) was cooled to −60° C. Ethylmagnesium bromide (3.0 M in THF, 481 µl, 1.444 mmol) was added dropwise and the resulting mixture was stirred for 1 hour. The mixture was diluted with water and EtOAc and the layers were separated. The organic layer was washed with saturated sodium bicarbonate, brine, dried over sodium sulfate, filtered and concentrated under reduced pressure. The residue was purified by chromatography on silica gel (5-80% EtOAc/Hexanes) to afford racemic-trans-ethyl 4-[1-(5-bromo-1,3-thiazol-2-yl)-1-hydroxypropyl]cyclohexanecarboxylate as a yellow solid. The racemic mixture was purified by super critical fluid chromatography (Chiral Technology AD-H 2.1×25 cm, 5 uM, 30%/70% Methanol/CO$_2$ with a 14 minute run time) to afford enantiomer 1 and enantiomer 2 as clear oils. Enantiomer 1 (retention time=7.24 min): MS ESI calc'd. for $C_{12}H_{22}BrNO_3S$ [M+H]$^+$ 376, 378. found 376, 378. $^1$H NMR (500 MHz, DMSO-d$_6$) δ 7.75 (s, 1H), 5.62 (s, 1H), 3.99 (q, J=7.0, 2H), 2.20-0.80 (m, 15H), 0.68 (t, J=6.9, 3H). Enantiomer 2 (retention time=10.18 min): MS ESI calcd for $C_{17}H_{26}BrNO_3S$ [M+H]$^+$ 376, 378. found 376, 378. $^1$H NMR (500 MHz, DMSO-d$_6$) δ 7.75 (s, 1H), 5.62 (s, 1H), 3.99 (q, J=7.0, 2H), 2.20-0.8 (m, 15H), 0.68 (t, J=6.9, 3H).

INTERMEDIATE 28 ethyl trans-4-[(S)-(5-bromo-1,3-thiazol-2-yl)(cyclopropyl)-hydroxymethyl]cyclohexanecarboxylate
ethyl trans-4-[(R)-(5-bromo-1,3-thiazol-2-yl)(cyclopropyl)hydroxymethyl]-cyclohexanecarboxylate

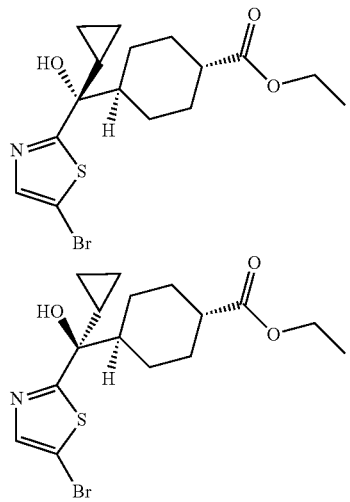

A solution of ethyl trans-4-[(5-bromo-1,3-thiazol-2-yl) carbonyl]cyclohexanecarboxylate (518 mg, 1.49 mmol) in anhydrous THF (16 ml) was treated dropwise over 20 min with cyclopropylmagnesium bromide (1.49 mmol, 0.5 M in tetrahydrofuran, 2.99 mL) at 0° C. under a nitrogen atmosphere. After stirring 1 h at room temperature, additional cyclopropylmagnesium bromide (2.23 mmol, 0.5 M in tetrahydrofuran, 4.48 mL) was added dropwise over 20 min at 0° C. and then the mixture was allowed to reach room temperature. After 4 h the mixture was diluted with saturated ammonium chloride and ethyl acetate, washed with brine, dried over magnesium sulfate, filtered and concentrated in vacuo. The residue was purified by chromatography on silica gel (0% to 20% EtOAc in hexanes) to afford racemic ethyl trans-4-[(5-bromo-1,3-thiazol-2-yl)(cyclopropyl)hydroxymethyl] cyclohexanecarboxylate as a white solid. Two enantiomers were separated by chiral super critical fluid chromatography (Chiral Technology AS, 2.1×25 cm, 10 uM, 45/55 MeOH/CO2, Flow Rate: 70 mL/min, 14 min run time, WL: 220 nm) Elution was observed at 7.91 min and 10.78 min. Pooled fractions of each peak were concentrated under reduced pressure.

Enantiomer 1 (retention time=7.91 min): ethyl trans-4-[(S or R)-(5-bromo-1,3-thiazol-2-yl)-(cyclopropyl)hydroxymethyl]cyclohexanecarboxylate. MS ESI calc'd. for $C_{16}H_{22}BrNO_3S$ [M+H]$^+$ 388, 390. found 388, 390. $^1$H NMR (500 MHz, CDCl$_3$) δ 7.56 (s, 1H), 4.10 (q, J=7.1, 2H), 2.24-2.11 (m, 2H), 2.10-2.02 (m, 1H), 1.99-1.94 (m, 1H), 1.92-1.84 (m, 1H), 1.58-1.12 (m, 6H), 1.23 (t, J=7.1, 3H), 0.60-0.49 (m, 2H), 0.40-0.27 (m, 2H).

Enantiomer 2 (retention time=10.78 min): ethyl trans-4-[(R or S)-(5-bromo-1,3-thiazol-2-yl)-(cyclopropyl)hydroxymethyl]cyclohexanecarboxylate. MS ESI calc'd. for $C_{16}H_{22}BrNO_3S$ [M+H]$^+$ 388, 390. found 388, 390. $^1$H NMR (500 MHz, CDCl$_3$) δ 7.56 (s, 1H), 4.10 (q, J=7.1, 2H), 2.24-2.11 (m, 2H), 2.10-2.02 (m, 1H), 1.99-1.94 (m, 1H), 1.92-1.84 (m, 1H), 1.58-1.12 (m, 6H), 1.23 (t, J=7.1, 3H), 0.60-0.49 (m, 2H), 0.40-0.27 (m, 2H).

INTERMEDIATE 29 ethyl trans-4-[1-(5-bromo-1,3-thiazol-2-yl)-1-hydroxy-2-methylpropyl]cyclohexanecarboxylate

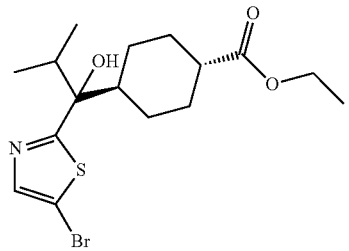 [SMILES: CCOC(=O)[C@H]1CC[C@H](C(O)(c2ncc(Br)s2)C(C)C)CC1]

A solution of ethyl trans-4-[(5-bromo-1,3-thiazol-2-yl)carbonyl]cyclohexanecarboxylate (800 mg, 2.31 mmol) in anhydrous THF (16 ml) was treated dropwise over 1 h with isopropylmagnesium bromide (2.31 mmol, 2 M, 1.15 mL) at 0° C. under a nitrogen atmosphere. After stirring at 0° C. for 15 min, the reaction was allowed to reach room temperature. After 1 h, the reaction mixture was quenched with saturated ammonium chloride and taken up in ethyl acetate, washed with brine and dried over magnesium sulfate, filtered and concentrated in vacuo. The residue was purified by chromatography on silica gel (0% to 20% EtOAc in hexanes) and then by preparative HPLC reverse phase (C-18) eluting with 55% to 100% water in acetonitrile (0.1% trifluoroacetic acid). The collected fractions were diluted with ethyl acetate and washed with saturated sodium bicarbonate, brine, dried over magnesium sulfate, filtered and concentrated in vacuo to afford racemic ethyl trans-4-[1-(5-bromo-1,3-thiazol-2-yl)-1-hydroxy-2-methylpropyl]cyclohexanecarboxylate as a white solid. MS ESI calc'd. for $C_{16}H_{24}BrNO_3S$ [M+H]$^+$ 390, 392. found 390, 392. $^1$H NMR (500 MHz, CDCl$_3$) δ 7.60 (s, 1H), 4.10 (q, J=7.1, 2H), 2.30-2.20 (m, 1H), 2.17-2.06 (m, 1H), 2.05-1.79 (m, 2H), 1.93-1.81 (m, 1H), 1.62-1.50 (m, 1H), 1.48-1.20 (m, 5H), 1.22 (t, J=7.1, 3H), 0.88 (d, J=9.8, 3H), 0.87 (d, J=9.8, 3H).

INTERMEDIATE 30 ethyl trans-4-[1-(5-bromo-1,3-thiazol-2-yl)-2-hydroxyethyl]cyclohexanecarboxylate

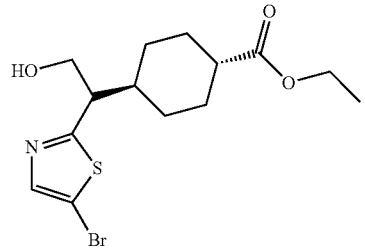 [SMILES: CCOC(=O)[C@H]1CC[C@H](C(CO)c2ncc(Br)s2)CC1]

Step 1: Methyl(triphenyl)phosphonium bromide (774 mg, 2.166 mmol) was suspended in anhydrous diethyl ether (5 mL) and potassium tert-butoxide (2.311 mmol, 1.78 M in THF, 1.29 mL) was added at 0° C. dropwise. The suspension was left 25 min at the same temperature (solution became orange-brown). A solution of diethyl ether (1 ml) and ethyl trans-4-[(5-bromo-1,3-thiazol-2-yl)carbonyl]cyclohexanecarboxylate (500 mg, 1.444 mmol) was added dropwise at 0° C. The mixture was left at the same temperature for 30 min, allowed to reach room temperature, left under stirring additional 90 min, diluted with water and taken up in ethyl acetate. The organic phase was washed with brine, dried over magnesium sulfate, filtered and concentrated in vacuo. The residue was purified by chromatography on silica gel (0% to 10% EtOAc in hexanes) to afford ethyl trans-4-[1-(5-bromo-1,3-thiazol-2-yl)ethenyl]-cyclohexanecarboxylate (62%) as an oil. MS ESI calc'd. for $C_{14}H_{18}BrNO_2S$ for [M+H]$^+$ 344, 346. found 344, 346. $^1$H NMR (500 MHz, CDCl$_3$) δ 7.55 (s, 1H), 5.60 (s, 1H), 5.19 (s, 1H), 4.04 (q, J=7.0, 2H), 2.62-2.78 (m, 1H), 2.20-2.30 (m, 1H), 1.90-2.02 (m, 3H), 1.50-1.60 (m, 2H), 1.10-1.30 (m, 2H), 1.17 (t, J=7.0, 3H), 0.72-0.82 (m, 1H).

Step 2: A solution of ethyl trans-4-[1-(5-bromo-1,3-thiazol-2-yl)ethenyl]cyclohexanecarboxylate (308 mg, 0.895 mmol) from Step 1 in dichloromethane (10 mL) was treated portionwise at 0° C. with meta-chloroperbenzoic acid (261 mg, 1.163 mmol, 77%). The mixture was stirred at room temperature for 16 h, diluted with dichloromethane and washed with 2N sodium hydroxide. The aqueous phase was extracted with dichloromethane and the combined organic layers were washed with brine, dried over magnesium sulfate and filtered. The volatiles were removed under reduced pressure and the crude product was purified by chromatography on silica gel (0% to 20% EtOAc in hexanes) to afford ethyl trans-4-[2-(5-bromo-1,3-thiazol-2-yl)oxiran-2-yl]cyclohexanecarboxylate as a colorless oil. MS ESI calc'd. for $C_{14}H_{18}BrNO_3S$ [M+H]$^+$ 360, 362. found 360, 362.

Step 3: A solution in DCM (0.7 mL) of ethyl trans-4-[2-(5-bromo-1,3-thiazol-2-yl)oxiran-2-yl]cyclohexanecarboxylate (30 mg, 0.082 mmol) from Step 2 was treated with trifluoroacetic acid (0.266 mL, 1.665 mmol) and triethylsilane (0.128 mL, 1.665 mmol) and left at 45° C. 16 h. The volatiles were removed under reduced pressure and the residue was taken up in dichloromethane, washed with saturated sodium bicarbonate, brine, dried over magnesium sulfate, filtered and concentrated in vacuo to afford racemic ethyl trans-4-[1-(5-bromo-1,3-thiazol-2-yl)-2-hydroxyethyl]cyclohexanecarboxylate which was used as such without further characterization. MS ESI calc'd. for $C_{14}H_{20}BrNO_3S$ [M+H]$^+$ 362, 364, found 362, 364.

INTERMEDIATE 31 trans-4-[amino(5-bromo-1,3-thiazol-2-yl)methyl]cyclohexanecarboxylic acid

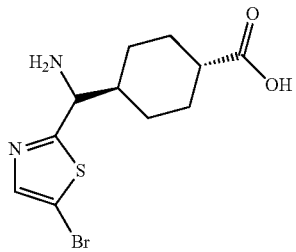 [SMILES: NC(c1ncc(Br)s1)[C@H]1CC[C@H](C(=O)O)CC1]

Step 1: trans-Ethyl 4-(5-bromothiazole-2-carbonyl)cyclohexanecarboxylate (150 mg, 0.433 mmol), sodium cyanoborohydride (63 mg, 1.00 mmol), ammonium acetate (83 mg, 1.08 mmol), THF (0.6 mL), and methanol (1.8 mL) were combined in a sealed vial and heated to a temperature of 80° C. for 16 hours. The mixture was cooled to 23° C. and subsequently transferred to a separatory funnel containing EtOAc. The organic layer was washed with saturated aqueous sodium bicarbonate, dried over sodium sulfate, filtered and concentrated to afford crude trans-ethyl 4-(amino(5-bromothiazol-2-yl)methyl)cyclohexanecarboxylate, which was used directly in the subsequent synthetic transformation without purification. MS ESI calc'd. For $C_{13}H_{20}BrN_2O_2S$ [M+H]$^+$ 347, 349. found 347, 349.

Step 2: The crude mixture from Step 1 was dissolved in methanol (3 mL), and sodium hydroxide (1.0 M in water, 0.950 mL, 0.950 mmol) was added to the resulting solution. The reaction mixture was then heated to a temperature of 50° C. for 30 minutes. The reaction was subsequently cooled, acidified with TFA (0.1 mL) and concentrated to afford racemic trans-4-[amino(5-bromo-1,3-thiazol-2-yl)methyl]cyclohexanecarboxylic acid, which was used in subsequent synthetic transformations without purification. MS ESI calc'd. for $C_{11}H_{15}BrN_2O_2S$ [M+H]$^+$ 319, 321. found 319, 321.

INTERMEDIATE 32 butyl trans-4-[(1S or 1R)-1-(5-bromo-1,3-thiazol-2-yl)-1-methoxyethyl]cyclohexanecarboxylate

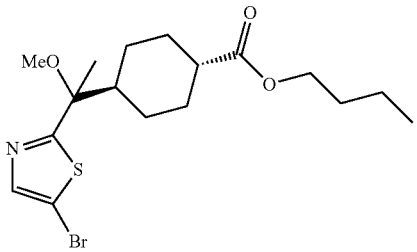 [SMILES: CCCCOC(=O)[C@H]1CC[C@H](C(C)(OC)c2ncc(Br)s2)CC1]

An anhydrous solution of butyl trans-4-[(1S or 1R)-1-(5-bromo-1,3-thiazol-2-yl)-1-hydroxyethyl]cyclohexanecarboxylate (Example 19, Step 3, $R_t$=7.86 min) (50 mg, 0.128 mmol) in DMF (1 mL) was treated at 0° C. with sodium hydride (7 mg, 0.179 mmol, 60% in mineral oil) and then stirred at room temperature for 10 min. Iodomethane (9 uL, 0.141 mmol) was added to the reaction mixture dropwise. After 1 h, additional NaH (4.5 mg, 0.128 mmol, 60% in mineral oil) was added at 0° C. followed by iodomethane (9 uL, 0.141 mmol). The resultant mixture was left under stirring at room temperature for 20 min, quenched with 1N hydrochloric acid and taken up in ethyl acetate. The organic phase was washed with brine and dried over magnesium sulfate, filtered and concentrated in vacuo. The residue was purified by chromatography on silica gel (0% to 15% EtOAc in hexanes) to afford butyl trans-4-[(1S or 1R)-1-(5-bromo-1,3-thiazol-2-yl)-1-methoxyethyl]cyclohexanecarboxylate as on oil. MS ESI calc'd. for $C_{17}H_{26}BrNO_3S$ [M+H]$^+$ 404, 406. found 404, 406. $^1$H NMR (500 MHz, CDCl$_3$) δ 7.57 (s, 1H), 4.12 (t, J=7.1, 2H), 3.21 (s, 3H), 2.21-2.13 (m, 1H), 2.07-2.00 (m, 1H), 1.99-1.92 (m, 2H), 1.75-1.66 (m, 1H), 1.61-1.50 (m, 3H), 1.51 (s, 3H), 1.46-1.30 (m, 4H), 1.21-1.12 (m, 1H), 1.03-0.93 (m, 1H), 0.91 (t, J=7.1, 3H).

INTERMEDIATE 33 ethyl trans-4-[1-(5-bromo-1,3-thiazol-2-yl)-1,2-dihydroxyethyl]cyclohexanecarboxylate

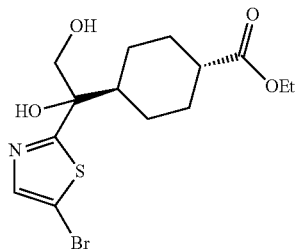 [SMILES: CCOC(=O)[C@H]1CC[C@H](C(O)(CO)c2ncc(Br)s2)CC1]

Ethyl trans-4-[1-(5-bromo-1,3-thiazol-2-yl)ethenyl]cyclohexanecarboxylate (40 mg, 0.12 mmol), 4-methylmorpholine N-oxide (31 mg, 0.27 mmol), THF (0.8 ml), water (0.4 ml) and osmium tetroxide (0.22 ml, 0.028 mmol) were combined and the mixture was stirred at room temperature for 40 min. The mixture was then diluted with saturated sodium thiosulfate and extracted with EtOAc. The organic phase was washed with water, brine, dried over sodium sulfate and concentrated in vacuo. The residue was purified on silica gel (EtOAc/hexane=1/1) to afford racemic ethyl trans-4-[1-(5-bromo-1,3-thiazol-2-yl)-1,2-dihydroxyethyl]cyclohexanecarboxylate. MS ESI calc'd. for $C_{14}H_{20}BrNO_4S$ [M+H]$^+$ 378, 380. found 378, 380. $^1$H NMR (500 MHz, CDCl$_3$) δ 7.55 (s, 1H), 4.15 (dd, J=5.7, 11.1, 1H), 4.07 (q, J=7.1, 2H), 3.74 (dd, J=7.0, 11.1, 1H), 2.61 (t, J=6.4, 1H), 2.20-2.10 (m, 1H), 2.05-1.84 (m, 3H), 1.85-1.70 (m, 1H), 1.60 (d, J=12.8, 1H), 1.46-1.13 (m, 5H), 1.13-1.05 (m, 1H).

INTERMEDIATE 34 ethyl trans-4-[1-(5-bromo-1,3-thiazol-2-yl)-2,2,2-trifluoro-1-hydroxyethyl]cyclohexanecarboxylate

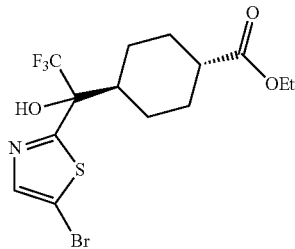 [SMILES: CCOC(=O)[C@H]1CC[C@H](C(O)(c2ncc(Br)s2)C(F)(F)F)CC1]

To a solution of ethyl trans-4-[(5-bromo-1,3-thiazol-2-yl)carbonyl]cyclohexane-carboxylate (608 mg, 1.756 mmol) in THF (15 ml) was added trifluoromethyl trimethylsilane (0.520 ml, 3.51 mmol). Then, tetrabutylammonium fluoride (7.0 ml, 7.00 mmol) was added to the mixture slowly. After 1 h, the mixture was diluted with water and extracted with EtOAc. The organic phase was washed with brine, dried over sodium sulfate, filtered and concentrated in vacuo. The residue was purified on silica gel (0-20% EtOAc in hexane) to afford racemic ethyl trans-4-[1-(5-bromo-1,3-thiazol-2-yl)-2,2,2-trifluoro-1-hydroxyethyl]cyclohexanecarboxylate. MS ESI calc'd. for $C_{14}H_{17}BrF_3NO_3S$ [M+H]$^+$ 416, 418. found 416, 418. $^1$H NMR (500 MHz, CDCl$_3$) δ 7.68 (s, 1H), 4.11 (q, J=7.1, 2H), 2.47-2.32 (m, 1H), 2.28-1.92 (m, 4H), 1.55-1.16 (m, 5H), 0.90 (t, J=7.3, 3H).

INTERMEDIATE 35 ethyl trans-4-[1-(5-bromo-1,3-thiazol-2-yl)-3,4-dihydroxybutyl]cyclohexanecarboxylate

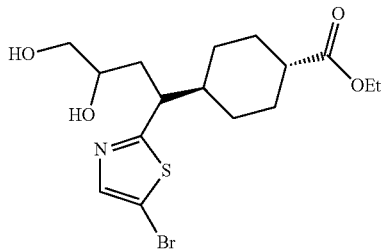 [SMILES: CCOC(=O)[C@H]1CC[C@H](C(CC(O)CO)c2ncc(Br)s2)CC1]

Step 1: Methyltriphenylphosphonium bromide (2.58 g, 7.22 mmol), potassium tert-butoxide (0.8248 g, 7.35 mmol) and toluene (24 ml) were combined and heated under reflux for 1 h. Then, the mixture was cooled to −10° C. and ethyl trans-4-[(5-bromo-1,3-thiazol-2-yl) carbonyl]cyclohexanecarboxylate (1.022 g, 2.95 mmol) in 2 ml of toluene was added dropwise. The mixture was stirred between 2° C. to 3° C. for 1.5 h. The reaction was diluted with aqueous saturated ammonium chloride, extracted with EtOAc (2×) and the combined organic phases were washed with water, brine, dried over sodium sulfate and concentrated in vacuo. The residue was purified on silica gel (0-8% EtOAc in hexane) to afford ethyl trans-4-[1-(5-bromo-1,3-thiazol-2-yl)but-3-en-1-yl]cyclohexanecarboxylate. MS ESI calc'd. for $C_{16}H_{22}BrNO_2S$ [M+H]$^+$ 372, 374. found 372, 374. $^1$H NMR (500 MHz, CDCl$_3$) δ 7.56 (s, 1H), 5.65 (dd, J=6.9, 10.2, 1H), 5.13-4.79 (m, 2H), 4.10 (q, J=7.1, 2H), 2.97-2.89 (m, 1H), 2.62-2.38 (m, 2H), 2.23-1.86 (m, 4H), 1.70-1.60 (m, 2H), 1.50-1.28 (m, 2H), 1.23 (t, J=7.0, 3H), 1.12-0.92 (m, 2H).

Step 2: Ethyl trans-4-[1-(5-bromo-1,3-thiazol-2-yl)but-3-en-1-yl]cyclohexanecarboxylate (40 mg, 0.107 mmol), 4-methylmorpholine N-oxide (14 mg, 0.120 mmol), THF (0.8 ml), water (0.4 ml) and osmium tetroxide (0.2 ml, 0.025 mmol). The mixture was stirred at room temperature for 15 min. The mixture was diluted with sodium thiosulfate and extracted with EtOAc. The organic phase was washed with water, brine, dried over sodium sulfate and concentrated in vacuo. The residue was purified on silica (0-100% EtOAc in hexane) to afford ethyl trans-4-[1-(5-bromo-1,3-thiazol-2-yl)-3,4-dihydroxybutyl]cyclohexanecarboxylate. MS ESI calc'd. for $C_{16}H_{24}BrNO_4S$ [M+H]$^+$ 406, 408. found 406, 408. $^1$H NMR (500 MHz, CDCl$_3$) δ 7.54 (s, 1H), 4.08 (q, J=7.1, 2H), 3.70-2.93 (m, 3H), 2.60-2.42 (m, 1H), 2.25-2.06 (m, 1H), 2.06-1.51 (m, 7H), 1.51-1.30 (m, 2H), 1.22 (t, J=7.1, 3H), 1.14-0.92 (m, 2H).

INTERMEDIATE 36 trans- and cis-ethyl 4-[(5-bromo-1,3-thiazol-2-yl)(hydroxy)methyl]-4-hydroxycyclohexanecarboxylate

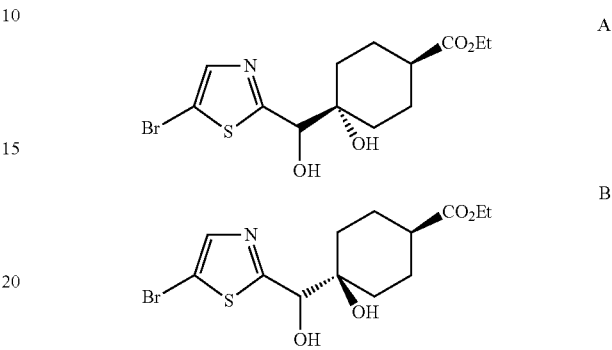

Step 1: 5-Bromo-2-methylthiazole (2.00 g, 11.23 mmol) was combined with N-bromosuccinimide (2.199 g, 12.36 mmol) and benzoyl peroxide (0.136 g, 0.562 mmol) in carbon tetrachloride (40 mL). The mixture was stirred under reflux overnight. The reaction was cooled to room temperature and the brown solution was filtered to remove solids and the filter cake was washed once with carbon tetrachloride. The combined filtrate was concentrated to a brown residue and purified by chromatography on silica gel (0-25% ether in hexanes) to afford 5-bromo-2-(bromomethyl)-1,3-thiazole as a yellow oil. $^1$H NMR (500 MHz, CDCl$_3$) δ 7.63 (s, 1H), 4.67 (s, 2H).

Step 2: 5-Bromo-2-(bromomethyl)-1,3-thiazole (1.02 g, 3.97 mmol) and triethyl phosphite (1.389 mL, 7.94 mmol) were combined in toluene (8 mL) and stirred at reflux overnight. The reaction was cooled to room temperature and concentrated in vacuo. The residue was purified by chromatography on silica gel (0-5% methanol in ethyl acetate) to afford diethyl[(5-bromo-1,3-thiazol-2-yl)methyl]phosphonate as a yellow oil. MS ESI calc'd. for $C_8H_{14}BrNO_3PS$ [M+H]$^+$ 314, 316. found 314, 316. $^1$H NMR (500 MHz, CDCl$_3$) δ 7.59 (s, 1H), 4.17-4.09 (m, 4H), 3.57 (d, J=21.2 Hz, 2H), 1.32 (t, J=7.1 Hz, 6H).

Step 3: A suspension of sodium hydride (60% in mineral oil, 122 mg, 3.06 mmol) in THF (10 mL) was cooled to 0° C., and diethyl[(5-bromo-1,3-thiazol-2-yl)methyl]phosphonate (769 mg, 2.448 mmol) in THF (2 mL) was added dropwise and subsequently stirred at 0° C. for 30 minutes. Ethyl 4-oxocyclohexanecarboxylate (417 mg, 2.448 mmol) in THF (2 mL) was then added, and allowed to warm to room temperature over 2 h. Then, the reaction was diluted with saturated ammonium chloride and extracted with ethyl acetate (2×). The combined organic layers were washed with brine, dried over magnesium sulfate, and concentrated under reduced pressure. The residue was purified by chromatography on silica gel (0-10% ethyl acetate in hexanes) to afford ethyl 4-[(5-bromo-1,3-thiazol-2-yl)methylidene]cyclohexanecarboxylate as a yellow oil. MS ESI calc'd. for $C_{13}H_{17}BrNO_2S$ [M+H]$^+$ 330, 332. found 330, 332. $^1$H NMR (600 MHz, CDCl$_3$) δ 7.62 (s, 1H), 6.34 (s, 1H), 4.14 (q, J=7.1 Hz, 2H), 3.41-3.33 (m, 1H), 2.60-2.52 (m, 1H), 2.47-2.40 (m, 1H), 2.31-2.19 (m, 2H), 2.12-2.02 (m, 2H), 1.80-1.63 (m, 2H), 1.26 (t, J=7.1 Hz, 3H).

Step 4: Ethyl 4-[(5-bromo-1,3-thiazol-2-yl)methylidene]cyclohexanecarboxylate (415 mg, 1.257 mmol), then 4-methylmorpholine N-oxide (294 mg, 2.51 mmol) were taken up in acetone (8 mL) and water (1 mL), and osmium tetroxide (4 wt % in water, 0.986 mL, 0.126 mmol) was added. The reaction was stirred at room temperature for 3 hours then diluted with 10% $Na_2S_2O_3$ and extracted with ethyl acetate (2×). The combined organic layers were washed with brine, dried over magnesium sulfate and concentrated under reduced pressure. The residue was purified by reverse phase HPLC (35-70% acetonitrile in water with 0.1% TFA) to separate the diastereomers of ethyl 4-[(5-bromo-1,3-thiazol-2-yl)(hydroxy)methyl]-4-hydroxycyclohexanecarboxylate. The pooled fractions of each isolated diastereomer were separately combined, concentrated to remove acetonitrile, diluted with aqueous saturated sodium bicarbonate, and extracted with dichloromethane (2×). Independently for each diastereomer, the combined organic layers were washed with brine, dried over magnesium sulfate and concentrated under reduced pressure. The faster eluting peak isolated by HPLC was intermediate 36-A: trans-ethyl 4-[(5-bromo-1,3-thiazol-2-yl)(hydroxy)methyl]-4-hydroxycyclohexanecarboxylate. MS ESI calc'd. for $C_{13}H_{19}BrNO_4S$ [M+H]$^+$ 364, 366. found 364, 366. $^1$H NMR (600 MHz, DMSO-d$_6$) δ 7.73 (s, 1H), 4.60 (s, 1H), 4.03 (q, J=7.1 Hz, 2H), 2.45 (s, 1H), 1.88-1.58 (m, 6H), 1.47-1.35 (m, 2H), 1.29-1.18 (m, 1H), 1.13 (t, J=7.1 Hz, 3H).

The slower eluting peak isolated by HPLC was intermediate 36-B: cis-ethyl 4-[(5-bromo-1,3-thiazol-2-yl)(hydroxy)methyl]-4-hydroxycyclohexanecarboxylate. MS ESI calc'd. for $C_{13}H_{19}BrNO_4S$ [M+H]$^+$ 364, 366. found 364, 366. $^1$H NMR (600 MHz, DMSO-d$_6$) δ 7.74 (s, 1H), 4.43 (s, 1H), 4.01 (q, J=7.1 Hz, 2H), 2.20-2.10 (m, 1H), 1.75-1.53 (m, 6H), 1.48-1.22 (m, 3H), 1.14 (t, J=7.1 Hz, 3H).

INTERMEDIATES 37 methyl (1S,3R)-3-[(1R)-1-hydroxy-1-(1,3-thiazol-2-yl)ethyl]cyclopentanecarboxylate, methyl (1S,3R)-3-[(1S)-1-hydroxy-1-(1,3-thiazol-2-yl)ethyl]cyclopentanecarboxylate, methyl (1R,3S)-3-[(1R)-1-hydroxy-1-(1,3-thiazol-2-yl)ethyl]cyclopentanecarboxylate, and methyl (1R,3S)-3-[(1S)-1-hydroxy-1-(1,3-thiazol-2-yl)ethyl]cyclopentanecarboxylate

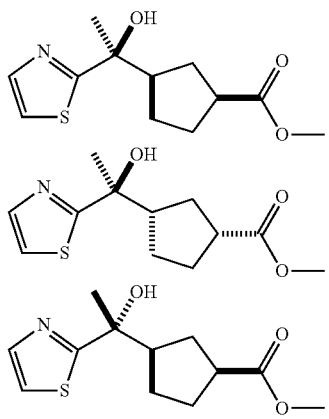

-continued

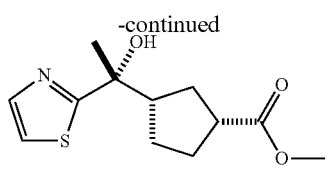

Thiazole (501 mg, 5.88 mmol) was dissolved in THF (1.2 mL) and isopropylmagnesium chloride lithium chloride complex (1.3 M solution in THF, 5.88 mL, 7.64 mmol) was added dropwise, and the resulting mixture was stirred at room temperature for 1 hr. Cis-methyl 3-acetylcyclopentanecarboxylate (1.2 g, 7.05 mmol) was then added as a solution in THF (2 mL) and the reaction mixture was stirred for 3 hrs at room temperature. The reaction mixture was diluted with saturated $NH_4Cl$ and diethyl ether. The organic layer was separated, dried over magnesium sulfate, filtered and concentrated under reduced pressure. The residue was purified by chromatography on silica gel (12% to 100% $Et_2O$ in Hexanes) to afford cis-methyl 3-[1-hydroxy-1-(1,3-thiazol-2-yl)ethyl]cyclopentanecarboxylate as a colorless oil; MS ESI calc'd. for $C_{12}H_{18}NO_3S$ [M+H]$^+$ 256. found 256.

The above product was then separated in the four single enantiomerically pure title compounds by SFC (Column: Chiral Technology AD-H 2.1×25 cm, 5 uM. Mobile Phase: 10%/90% Ethanol/$CO_2$. Flow rate: 70 mL/Min. Wavelength: 220 nm).

Isomer 1
(R$_t$=4.98 min): $^1$H NMR (500 MHz, CDCl$_3$) δ 7.70 (d, J=3.2 Hz, 1H), 7.23 (d, J=3.4 Hz, 1H), 4.17 (bs, 1H), 3.69 (s, 3H), 2.80-2.76 (m, 2H), 1.97-1.93 (m, 3H), 1.91-1.66 (m, 3H), 1.59 (s, 3H).

Isomer 2
(R$_t$=5.55 min): $^1$H NMR (500 MHz, CDCl$_3$) δ 7.68 (d, J=3.1 Hz, 1H), 7.22 (d, J=3.2 Hz, 1H), 4.28 (bs, 1H), 3.64 (s, 3H), 2.78-2.73 (m, 2H), 1.96-1.82 (m, 3H), 1.77-1.60 (m, 3H), 1.57 (s, 3H).

Isomer 3
(R$_t$=7.39 min): $^1$H NMR (500 MHz, CDCl$_3$) δ 7.70 (bs, 1H), 7.23 (d, J=2.7 Hz, 1H), 4.28 (bs, 1H), 3.68 (s, 3H), 2.87-2.80 (m, 1H), 2.68-2.63 (m, 1H), 2.10-2.05 (m, 1H), 1.96-1.81 (m, 3H), 1.63 (s, 3H), 1.57-1.42 (m, 1H), 1.40-1.36 (m, 1H).

Isomer 4
(R$_t$=7.88 min): $^1$H NMR (500 MHz, CDCl$_3$) δ 7.68 (d, J=3.0 Hz, 1H), 7.22 (d, J=2.8 Hz, 1H), 3.92 (bs, 1H), 3.66 (s, 3H), 2.83-2.80 (m, 1H), 2.67-2.63 (m, 1H), 2.08-2.06 (m, 1H), 1.94-1.78 (m, 3H), 1.62 (s, 3H), 1.56-1.52 (m, 1H), 1.38-1.36 (m, 1H).

INTERMEDIATE 38

-[trans-4-(hydroxymethyl)cyclohexyl]-1-(1,3-thiazol-2-yl)ethanol

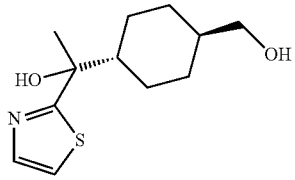 [SMILES: CC(O)(c1nccs1)[C@H]1CC[C@H](CO)CC1]

Step 1: Thiazole (100 mg, 1.175 mmol) was dissolved in THF (11 mL) and cooled to a temperature of −78° C. N-butyllithium (2 M in hexanes, 0.587 mL, 1.175 mmol) was added and the mixture was allowed to stir for 30 minutes at −78° C. A solution of trans-butyl 4-acetylcyclohexanecarboxylate (319 mg, 1.410 mmol) in THF (1 mL) was then added to the mixture, and the combined solution was allowed to stir for 1 hour at −78° C. The reaction was diluted with water, warmed to 23° C., and transferred to a separatory funnel containing EtOAc. The layers were separated and the organic layer was washed with water, dried over sodium sulfate, filtered and concentrated. The residue was purified by chromatography on silica gel to afford butyl trans-4-[1-hydroxy-1-(1,3-thiazol-2-yl)ethyl]cyclohexanecarboxylate. MS ESI calc'd. for $C_{16}H_{26}NO_3S$ [M+H]$^{+\ 312}$. found 312.

Step 2: Butyl trans-4-[1-hydroxy-1-(1,3-thiazol-2-yl)ethyl]cyclohexanecarboxylate (150 mg, 0.482 mmol) was placed in a vial under an atmosphere of nitrogen and THF (2 mL) was added. Lithium aluminum hydride (3.5 M in THF, 0.270 mL, 0.945 mmol) was added. After 20 min of stirring at 23° C. the reaction was diluted carefully with methanol (5 mL) via dropwise addition. The resulting white suspension was filtered through CELITE, and the filtrate was concentrated to afford 1-[trans-4-(hydroxymethyl)cyclohexyl]-1-(1,3-thiazol-2-yl)ethanol, which was used in subsequent synthetic transformations without purification. MS ESI calc'd. for $C_{12}H_{19}NO_2S$ [M+H]$^+$ 242. found 242.

INTERMEDIATE 39 methyl 4-[1-hydroxy-1-(1,3-thiazol-2-yl)ethyl]-1-methylcyclohexanecarboxylate

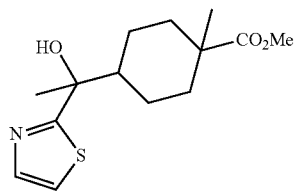 [SMILES: COC(=O)C1(C)CCC(C(C)(O)c2nccs2)CC1]

Step 1: To a solution of lithium diisopropyl amide (1.8 M in tetrahydrofuran/heptane/ethylbenzene, 46.2 mL, 83 mmol) at −78° C. was added a solution of 4-(methoxycarbonyl)-cyclohexanecarboxylic acid (6.2 g, 33.3 mmol) in tetrahydrofuran (80 mL) over 15 minutes via cannula needle. After 40 minutes of stirring, iodomethane (3.12 mL, 49.9 mmol) was added over 30 seconds to the brown reaction mixture. After 45 minutes the reaction bath was allowed to warm to room temperature over four hours, then the reaction mixture was cooled to 0° C. before hydrochloric acid (2.0 M in water, 100 mL) was added. The reaction mixture was diluted with hexanes (50 mL) and the layers were separated. The aqueous layer was extracted with ethyl acetate (2×100 mL). The combined organic layers were washed with brine (3×50 mL), dried over sodium sulfate, filtered, and concentrated to give 4-(methoxycarbonyl)-4-methylcyclohexanecarboxylic acid, which was used without further purification.

Step 2: A solution of 4-(methoxycarbonyl)-4-methylcyclohexanecarboxylic acid (6.67 g, 33.3 mmol) in dichloromethane (30 mL) was charged with thionyl chloride (40 mL, 80 mmol) and then heated to 38° C. for 17 hours. The reaction mixture was cooled to room temperature and then concentrated under reduced pressure to yield methyl 4-(chlorocarbonyl)-1-methylcyclohexanecarboxylate, which was used without further purification.

Step 3: To a deoxygenated solution of methyl 4-(chlorocarbonyl)-1-methylcyclohexanecarboxylate (7.282 g, 33.3 mmol) and palladium (II) acetate (374 mg, 1.665 mmol) in 1,4-dioxane (200 mL) was added dimethylzinc (2.0 M in toluene, 16.65 mL, 33.3 mmol). The black reaction mixture was heated under an inert atmosphere at 38° C. for 15 hours before being diluted with water (30 mL). The resulting suspension was filtered twice through CELITE. The filtrate was dried over magnesium sulfate and concentrated under reduced pressure. The residue was purified by chromatography on silica gel (5-45% ethyl acetate/hexanes) to afford methyl 4-acetyl-1-methylcyclohexanecarboxylate. MS ESI calc'd. for $C_{11}H_{18}O_3$ [M+H]$^+$ 199. found 199.

Step 4: To a solution of thiazole (0.309 mL, 4.36 mmol) in tetrahydrofuran (5 mL) was added a solution of isopropylmagnesium chloride lithium chloride complex (1.0 M in tetrahydrofuran, 3.36 mL, 4.36 mmol). After 20 minutes, the resulting solution was added to a solution of methyl 4-acetyl-1-methylcyclohexanecarboxylate (864.9 mg, 4.36 mmol) in tetrahydrofuran (10 mL) via syringe over 6 minutes. After 90 minutes, saturated aqueous ammonium chloride solution (5 mL) was added to the reaction mixture and the resulting suspension was partitioned between water (5 mL) and ethyl acetate (30 mL). The organic layer was washed with saturated aqueous sodium bicarbonate solution and brine, dried over sodium sulfate, filtered, and concentrated under reduced pressure. The residue was purified by chiral chromatography (methanol/supercritical $CO_2$) to give four separate stereoisomers (peak 1, peak 2, peak 3, peak 4) of methyl 4-[1-hydroxy-1-(1,3-thiazol-2-yl)ethyl]-1-methylcyclohexanecarboxylate. MS ESI calc'd. for $C_{14}H_{21}NO_3S$ [M+H]$^+$ 284. found 284.

INTERMEDIATE 40

(1S,2S)-1-hydroxy-N-methyl-1-phenylpropan-2-aminium trans-4-[(1R or 1S)-1-(5-bromo-1,3-thiazol-2-yl)-1-hydroxyethyl]cyclohexanecarboxylate

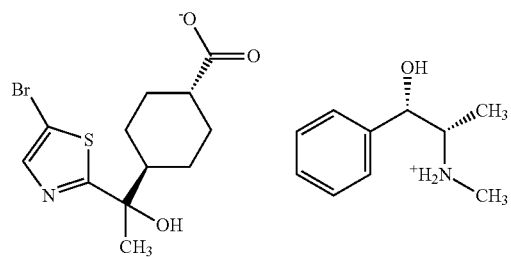

Step 1: Sodium hydroxide (3.0 M in $H_2O$, 5.98 mL, 17.93 mmol) was added to a solution of racemic butyl trans-4-[1-(5-bromo-1,3-thiazol-2-yl)-1-hydroxyethyl]cyclohexanecarboxylate (2.0 g, 5.12 mmol) in methanol (6 mL) and heated to 70° C. for 3 hour. Then, the reaction was cooled to room temperature and acidified with hydrochloric acid (3.0 M in $H_2O$). Water (10 mL) was added and the mixture was stirred overnight at which point crystallization occurred. The reaction was filtered and the filter cake was washed with water and then dried under a nitrogen bag to afford racemic trans-4-[1-(5-bromo-1,3-thiazol-2-yl)-1-hydroxyethyl]cyclohexanecarboxylic acid as a white solid. MS ESI calc'd. for $C_{12}H_{17}BrNO_3S$ [M+H]$^+$ 334, 336. found 334, 336. $^1$H NMR (600 MHz, DMSO-d$_6$) δ 11.92 (s, 1H), 7.69 (s, 1H), 5.91 (s, 1H), 2.03-1.93 (m, 1H), 1.92-1.85 (m, 1H), 1.85-1.77 (m, 2H), 1.62-1.51 (m, 1H), 1.48-1.35 (m, 4H), 1.25-1.08 (m, 3H), 1.04-0.88 (m, 1H).

Step 2: (1R,2R)-2-(methylamino)-1-phenylpropan-1-ol (0.25 g, 1.50 mmol) was added to a solution of racemic trans-4-[1-(5-bromo-1,3-thiazol-2-yl)-1-hydroxyethyl]cyclohexanecarboxylic acid (500 mg, 1.50 mmol) and the resulting solution was stirred at room temperature overnight, at which point crystallization occurred. The resulting solid was collected by filtration and washed with 1:1 EtOAc:hexane. The resulting mother liquor was concentrated in vacuo and then isopropanol (3.5 mL) and (1S,2S)-2-(methylamino)-1-phenylpropan-1-ol were added. The reaction was stirred overnight, at which point crystallization occurred. Then EtOAc (3 mL) was added and after 20 minutes, the solid was collected via filtration and the filter cake was washed with EtOAc and then dried under a nitrogen bag to afford (1S,2S)-1-hydroxy-N-methyl-1-phenylpropan-2-aminium trans-4-[(1R or 1S)-1-(5-bromo-1,3-thiazol-2-yl)-1-hydroxyethyl] cyclohexanecarboxylate as a white solid. MS ESI calc'd. for $C_{12}H_{17}BrNO_3S$ [M+H]$^+$ 334, 336. found 334, 336. $^1$H NMR (500 MHz, DMSO-d$_6$) δ 7.73 (s, 1H), 7.30-7.27 (m, 4H), 7.25-7.19 (m, 1H), 5.95 (s, 1H), 4.20 (d, J=7.7, 1H), 2.60-2.52 (m, 1H), 2.29 (s, 3H), 2.03-1.92 (m, 1H), 1.92-1.86 (m, 1H), 1.86-1.78 (m, 2H), 1.63-1.52 (m, 1H), 1.48-1.37 (m, 4H), 1.27-1.08 (m, 4H), 1.06-0.89 (m, 1H), 0.68 (d, J=6.4, 3H).

EXAMPLE 1 trans-4-{(1R)-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid trans-4-{(1S)-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid

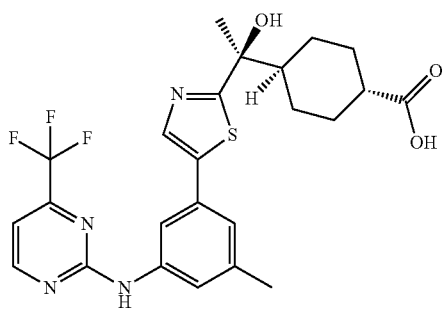

-continued

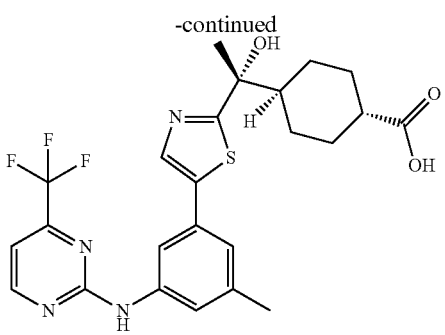

Step 1: A flask containing THF (78 mL) was cooled to −78° C. LDA (1.8 M in THF/heptane/ethylbenzene, 21.7 mL, 39.1 mmol) was added followed by a solution of N-[3-methyl-5-(1,3-thiazol-5-yl)phenyl]-4-(trifluoromethyl)pyrimidin-2-amine (2.63 g, 7.82 mmol) in THF (25 mL). The resulting solution was allowed to stir at −78° C. for thirty minutes. A solution of butyl trans-4-acetylcyclohexanecarboxylate (2.65 g, 11.73 mmol) in THF (10 mL) was added in one portion and the solution was stirred for 1 hour at −78° C. The reaction was then diluted with water and allowed to warm to room temperature. The mixture was then diluted with water and ethyl acetate. The organic layer was separated, dried over magnesium sulfate, filtered and concentrated in vacuo. The residue was purified by chromatography on silica gel to afford racemic butyl trans-4-{1-hydroxy-1-[5-(3-methyl-5-{[4-(trifluoromethyl)pyrimidin-2-yl]amino}-phenyl)-1,3-thiazol-2-yl]ethyl}cyclohexanecarboxylate. MS ESI calc'd. for $C_{28}H_{34}F_3N_4O_3S$ [M+H]$^+$ 563. found 563. $^1$H NMR (500 MHz, DMSO-d$_6$) δ 10.24 (s, 1H), 8.83 (d, J=4.9, 1H), 7.98-7.91 (m, 2H), 7.45 (s, 1H), 7.27 (d, J=4.9, 1H), 7.14 (s, 1H), 5.84 (s, 1H), 3.96 (t, J=6.5, 2H), 2.31 (s, 3H), 2.16-2.06 (m, 1H), 1.99-1.79 (m, 2H), 1.64 (s, 1H), 1.58-1.44 (m, 6H), 1.32-1.18 (m, 6H), 1.04 (d, J=13.1, 1H), 0.85 (t, J=7.4, 3H). rhSyk=+++

Step 2: To a solution of butyl trans-4-{1-hydroxy-1-[5-(3-methyl-5-{[4-(trifluoromethyl)-pyrimidin-2-yl]amino}phenyl)-1,3-thiazol-2-yl]ethyl}cyclohexanecarboxylate (600 mg, 1.066 mmol) in methanol (10.7 mL) was added sodium hydroxide (1.0 M in H$_2$O, 2.13 mL, 2.13 mmol) and the reaction was heated overnight at 100° C. The reaction was then cooled to room temperature, acidified with HCl (1.0 M in H$_2$O) to a pH of ~3 and then diluted with water and ethyl acetate. The organic layer was separated, dried over magnesium sulfate, filtered and concentrated. The residue was purified and at the same time the enantiomers separated by supercritical fluid chromatography (Chiral OJ column, 35%:75% methanol/CO$_2$ 5.0 min run time) to yield trans-4-{(1R)-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid and trans-4-{(1S)-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid. Characterization data for the faster eluting enantiomer (R$_t$=3.22 min): MS ESI calc'd. for $C_{24}H_{26}F_3N_4O_3S$ [M+H]$^+$ 507. found 507. $^1$H NMR (500 MHz, DMSO-d$_6$) δ 10.24 (s, 1H), 8.83 (d, J=4.9, 1H), 7.99-7.92 (m, 2H), 7.45 (s, 1H), 7.27 (d, J=4.9, 1H), 7.14 (s, 1H), 5.82 (s, 1H), 2.31 (s, 3H), 2.10-1.95 (m, 1H), 1.95-1.73 (m, 2H), 1.72-1.58 (m, 1H), 1.58-1.50 (m, 1H), 1.47 (s, 3H), 1.32-1.11 (m, 4H), 1.10-0.94 (m, 1H). rhSyk=+++. The slower eluting enantiomer R$_t$=4.04 min. rhSyk=+++

The following compounds were prepared in an analogous manner of that described in Example 1 using appropriate intermediates. Unless otherwise specified, the terms cis and trans refer to the stereochemistry around the cycloalkyl ring.

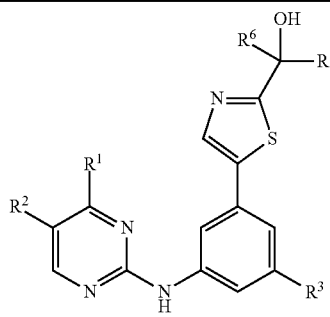

| Ex. | R¹/R² | R⁶ | R | rhSyk Activity | [M + H]+ Obs'd | Form(s) |
|---|---|---|---|---|---|---|
| 1-1 | CF₃/H | CH₃ | (1S,3R) 2,2-dimethylcyclobutane-CO₂H | +++ | 507 | TFA Salt |
| 1-2 | CF₃/H | CH₃ | adamantane-CO₂H (racemic) | +++ | 559 | TFA Salt |
| 1-3 | CF₃/H | CH₃ | cyclopropane w/ C(CH₃)₂CO₂H (racemic, cis isomer) | +++ | 507 | Free Base |
| 1-4 | CF₃/H | CH₃ | cyclopropane w/ C(CH₃)₂CO₂H (racemic, trans isomer) | +++ | 507 | Free Base |
| 1-5 | CF₃/H | CH₃ | cyclopropane w/ C(CH₃)₂CO₂H (trans isomer, enantiomer 1) | +++ | 507 | Free Base |
| 1-6 | CF₃/H (S) | CH₃ | cyclopropane w/ C(CH₃)₂CO₂H (trans isomer, enantiomer 2) | +++ | 507 | Free Base |
| 1-7 | CF₃/H | CH₃ | bicyclic HO₂C- (isomer 1) | +++ | 505 | TFA Salt |

-continued

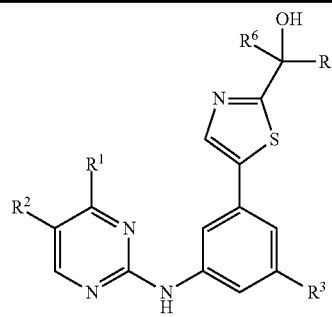

| Ex. | R¹/R² | R⁶ | R | rhSyk Activity | [M + H]+ Obs'd | Form(s) |
|---|---|---|---|---|---|---|
| 1-8 | CF₃/H | CH₃ | HO₂C—[bicyclic]—⸿ (isomer 2) | +++ | 505 | TFA Salt |
| 1-9 | CF₃/H | CH₃ | HO₂C—[bicyclic]—⸿ (isomer 3) | +++ | 505 | TFA Salt |
| 1-10 | CF₃/H | CH₃ | HO₂C—[bicyclic]—⸿ (enantiomer 1) | +++ | 505 | TFA Salt |
| 1-11 | CF₃/H | CH₃ | HO₂C—[bicyclic]—⸿ (enantiomer 2) | +++ | 505 | TFA Salt |
| 1-12 | CF₃/H | CH₃ | ⸿—[bicyclic]—CO₂H | +++ | 505 | TFA Salt |
| 1-13 | CF₃/H | H | H₃CO₂C—[cyclohexyl]—⸿ (mixture of cis and trans isomers) | +++ | 507 | Free Base |
| 1-14 | CF₃/H | H | HO₂C—[cyclohexyl]—⸿ (mixture of cis and trans isomers) | +++ | 493 | Free Base |
| 1-15 | CF₃/H | H | HO₂C—[cyclohexyl]—⸿ (cis isomer, racemic mixture) | +++ | 493 | Free Base |

-continued

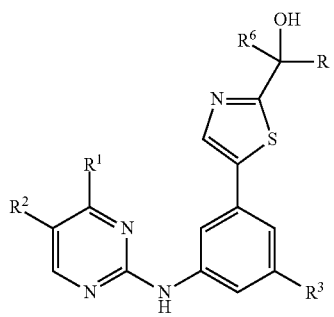

| Ex. | R¹/R² | R⁶ | R | rhSyk Activity | [M + H]+ Obs'd | Form(s) |
|---|---|---|---|---|---|---|
| 1-16 | $CF_3$/H | H | $HO_2C$-cyclohexyl- (trans isomer, racemic mixture) | +++ | 493 | Free Base |
| 1-17 | $CF_3$/H | $CH_3$ | $H_3C$, $CH_3$ dimethylcyclobutyl-$CH_2CO_2H$ (cis isomer, racemic mixture) | +++ | 521 | Ammonium Salt |
| 1-18 | cPr/F | $CH_3$ | $HO_2C$-cyclohexyl- (trans isomer, racemic mixture) | +++ | 497 | TFA Salt |
| 1-19 | $CF_3$/H | $CH_3$ | HO-$CH_2$-cyclohexyl- (trans isomer, racemic mixture) | +++ | 493 | Free Base |
| 1-20 | | | (full structure shown) | ++ | 505 | Free Base |

EXAMPLE 2 trans-4-{(R)-cyclopropyl(hydroxy) [5-(3-methyl-5-{[4-(trifluoromethyl)pyrimidin-2-yl]amino}phenyl)-1,3-thiazol-2-yl]methyl}cyclohexanecarboxylic acid trans-4-{(S)-cyclopropyl(hydroxy) [5-(3-methyl-5-{[4-(trifluoromethyl)pyrimidin-2-yl]amino}phenyl)-1,3-thiazol-2-yl]methyl}cyclohexanecarboxylic acid

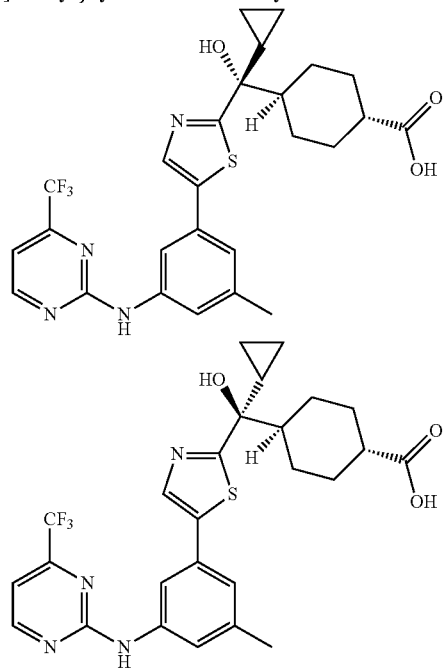

Step 1: A mixture of (4-trifluoromethyl-pyrimidin-2-yl)-[3-methyl-5-(4,4,5,5-tetramethyl-[1,3,2]dioxaborolan-2-yl)-phenyl]-amine (29 mg, 0.077 mmol), ethyl trans-4-[(R or S)-(5-bromo-1,3-thiazol-2-yl)(cyclopropyl)hydroxymethyl] cyclohexanecarboxylate (Intermediate 28, faster eluting enantiomer, $R_t$=7.91 min) (30 mg, 0.077 mmol), and $PdCl_2$ $(dppf)_2$-$CH_2Cl_2$ adduct (3 mg, 0.05 mmol) was taken up in degassed 2-methyltetrahydrofuran (1 mL) and sodium carbonate (2 M in water, 77 uL). The reaction flask was purged with nitrogen and heated to 80° C. for 16 h. The mixture was cooled to room temperature, diluted with ethyl acetate washed with brine and dried over magnesium sulfate, filtered and concentrated in vacuo. The residue was purified by chromatography on silica gel (0% to 50% EtOAc in hexanes) to afford 30 mg (69%) of ethyl trans-4-{(S or R)-cyclopropyl (hydroxy)[5-(3-methyl-5-{[4-(trifluoromethyl)pyrimidin-2-yl]amino}phenyl)-1,3-thiazol-2-yl] methyl}cyclohexanecarboxylate as a colorless oil. MS ESI calc'd. for $C_{28}H_{31}F_3N_4O_3S$ [M+H]$^+$ 561. found 561. $^1$H NMR (500 MHz, DMSO-$d_6$) δ 10.25 (s, 1H), 8.83 (d, J=4.8, 1H), 8.03-7.88 (m, 2H), 7.44 (s, 1H), 7.28 (d, J=4.7, 1H), 7.14 (s, 1H), 5.21 (s, 1H), 4.00 (q, J=7.1, 2H), 2.30 (s, 3H), 2.16-1.99 (m, 2H), 1.95-1.80 (m, 3H), 1.62-1.47 (m, 1H), 1.44-1.07 (m, 10H), 0.47-0.33 (m, 2H).

Step 2: To a solution of the trans-4-{(S or R)-cyclopropyl (hydroxy)[5-(3-methyl-5-{[4-(trifluoromethyl)pyrimidin-2-yl]amino}phenyl)-1,3-thiazol-2-yl] methyl}cyclohexanecarboxylate (30 mg, 0.054 mmol) from Step 1 in a mixture 1:1:1 of THF:methanol:water (1.5 mL) was added sodium hydroxide (1M, 0.214 mL) and left 16 h at room temperature. The reaction mixture was quenched with hydrochloric acid (1M in water) and extracted with ethyl acetate. The organic phase was washed with brine, dried over magnesium sulfate, filtered and concentrated in vacuo. The residue was purified by reverse phase preparative HPLC (C-18, eluting with 50% to 100% water in acetonitrile containing 0.1% trifluoroacetic acid) to afford trans-4-{(R or S)-cyclopropyl(hydroxy)[5-(3-methyl-5-{[4-(trifluoromethyl)pyrimidin-2-yl]amino}phenyl)-1,3-thiazol-2-yl] methyl}cyclohexanecarboxylic acid as a pale yellow solid. MS ESI calc'd. for $C_{26}H_{27}F_3N_4O_3S$ [M+H]$^+$ 533. found 533. $^1$H NMR (500 MHz, DMSO-$d_6$) δ 11.97 (s, 1H), 10.24 (s, 1H), 8.83 (d, J=5.0, 1H), 7.96 (s, 1H), 7.94 (s, 1H), 7.45 (s, 1H), 7.28 (d, J=5.0, 1H), 7.13 (s, 1H), 5.18 (s, 1H), 2.31 (s, 3H), 2.08-1.97 (m, 2H), 1.96-1.83 (m, 3H), 1.57-1.51 (m, 1H), 1.40-1.05 (m, 6H), 0.45-0.32 (m, 2H), 0.22-0.14 (m, 1H). rhSyk=+++. This reaction sequence was also followed to prepare trans-4-{(R or S)-cyclopropyl(hydroxy)[5-(3-methyl-5-{[4-(trifluoromethyl)pyrimidin-2-yl]amino}phenyl)-1,3-thiazol-2-yl]methyl}cyclohexanecarboxylic using Intermediate 28 (slower eluting enantiomer, $R_t$=10.78 min) in step 1. rhSyk=+++.

The following compounds were prepared using the route shown in Example 2 using the appropriate intermediates. Unless otherwise specified, the terms cis and trans refer to the stereochemistry around the cycloalkyl ring.

| Ex. | $R^1/R^2$ | $R^6$ | R | rhSyk Activity | [M + H]+ Obs'd | Form(s) |
|---|---|---|---|---|---|---|
| | | | $R^3 = CH_3$ | | | |
| 2-1 | $CF_3$/H | $CH_3$ | HO$_2$C-cyclohexyl- (cis isomer, racemic) | +++ | 507 | TFA Salt |

-continued

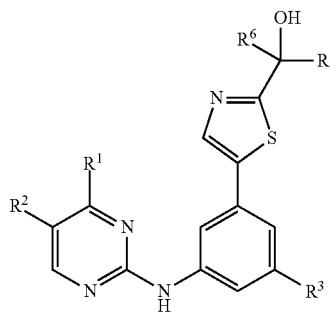

| Ex. | R¹/R² | R⁶ | R | rhSyk Activity | [M + H]+ Obs'd | Form(s) |
|---|---|---|---|---|---|---|
| 2-2 | CF₃/H | CH₃ | nBu—OC(O)—⬡—⌇ (cis isomer, enantiomer 1) | ++ | 563 | Free Base |
| 2-3 | CF₃/H | CH₃ | nBu—OC(O)—⬡—⌇ (cis isomer, enantiomer 2) | + | 563 | Free Base |
| 2-4 | CF₃/H | CH₃ | HO₂C—⬡—⌇ (cis isomer, enantiomer 2) | +++ | 507 | Free Base |
| 2-5 | CF₃/H | Et | Et—O₂C—⬡—⌇ (trans isomer, enantiomer 1) | ++ | 549 | Free Base |
| 2-6 | CF₃/H | CH₃ | HO₂C—⬡—⌇ (cis isomer, enantiomer 1) | +++ | 507 | Free Base |
| 2-7 | CF₃/H | Et | Et—O₂C—⬡—⌇ (trans isomer, enantiomer 2) | +++ | 549 | Free Base |
| 2-8 | CF₃/H | Et | HO₂C—⬡—⌇ (trans isomer, enantiomer 1) | +++ | 521 | Free Base |

-continued

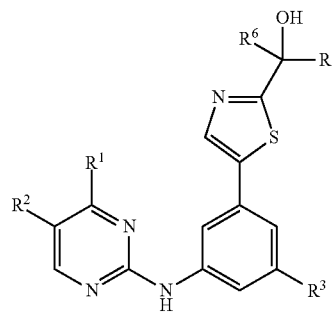

| Ex. | R¹/R² | R⁶ | R | rhSyk Activity | [M + H]+ Obs'd | Form(s) |
|---|---|---|---|---|---|---|
| 2-9 | CF₃/H | Et | HO₂C-cyclohexyl- (trans isomer, enantiomer 2) | +++ | 521 | Free Base |
| 2-10 | CF₃/H | CH₃ | Et—O₂C-(1)-cyclohexyl(4)-, 2-H₃C ((1,2-cis)-(1,4-trans), isomer 1) | ++ | 549 | Free Base |
| 2-11 | CF₃/H | CH₃ | Et—O₂C-(1)-cyclohexyl(4)-, 2-H₃C ((1,2-cis)-(1,4-trans), isomer 2) | ++ | 549 | Free Base |
| 2-12 | CH₃/H | CH₃ | Et—O₂C-(1)-cyclohexyl(4)-, 2-H₃C ((1,2-cis)-(1,4-trans), isomer 1) | ++ | 495 | Free Base |
| 2-13 | CF₃/H | CH₃ | Et—O₂C-(1)-cyclohexyl(4)-, 2-H₃C ((1,2-cis)-(1,4-trans), isomer 3) | ++ | 549 | Free Base |
| 2-14 | CF₃/H | CH₃ | Et—O₂C-(1)-cyclohexyl(4)-, 2-H₃C ((1,2-cis)-(1,4-trans), isomer 4) | ++ | 549 | Free Base |

-continued

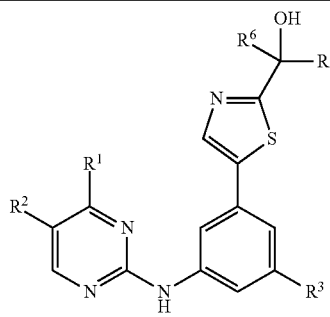

| Ex. | $R^1/R^2$ | $R^6$ | R | rhSyk Activity | [M + H]+ Obs'd | Form(s) |
|---|---|---|---|---|---|---|
| 2-15 | $CH_3$/H | $CH_3$ | H₃C—cyclohexyl(2-methyl,1-CO₂Et,4-linker) ((1,2-cis)-(1,4-trans), isomer 2) | ++ | 495 | Free Base |
| 2-16 | $CH_3$/H | $CH_3$ | H₃C—cyclohexyl(2-methyl,1-CO₂Et,4-linker) ((1,2-cis)-(1,4-trans), isomer 3) | +++ | 495 | Free Base |
| 2-17 | $CH_3$/H | $CH_3$ | H₃C—cyclohexyl(2-methyl,1-CO₂H,4-linker) ((1,2-cis)-(1,4-trans), isomer 1) | +++ | 467 | Free Base |
| 2-18 | $CH_3$/H | $CH_3$ | H₃C—cyclohexyl(2-methyl,1-CO₂H,4-linker) ((1,2-cis)-(1,4-trans), isomer 2) | +++ | 467 | Free Base |
| 2-19 | $CF_3$/H | $CH_3$ | H₃C—cyclohexyl(2-methyl,1-CO₂H,4-linker) ((1,2-cis)-(1,4-trans), isomer 1) | +++ | 521 | Free Base |
| 2-20 | $CF_3$/H | $CH_3$ | H₃C—cyclohexyl(2-methyl,1-CO₂H,4-linker) ((1,2-cis)-(1,4-trans), isomer 2) | +++ | 521 | Free Base |

-continued

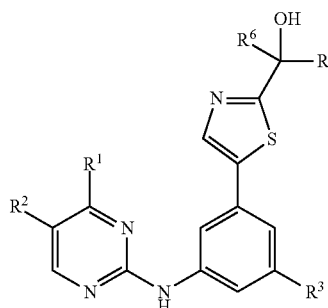

| Ex. | R¹/R² | R⁶ | R | rhSyk Activity | [M + H]+ Obs'd | Form(s) |
|---|---|---|---|---|---|---|
| 2-21 | CH₃/H | CH₃ | H₃C–[cyclohexane with 2-Me, 1-CO₂H, 4-link]<br>((1,2-cis)-(1,4-trans), isomer 3) | +++ | 467 | Free Base |
| 2-22 | CH₃/H | CH₃ | H₃C–[cyclohexane with 2-Me, 1-CO₂H, 4-link]<br>((1,2-cis)-(1,4-trans), isomer 4) | +++ | 467 | Free Base |
| 2-23 | CF₃/H | CH₃ | H₃C–[cyclohexane with 2-Me, 1-CO₂H, 4-link]<br>((1,2-cis)-(1,4-trans), isomer 3) | +++ | 521 | Free Base |
| 2-24 | CF₃/H | CH₃ | H₃C–[cyclohexane with 2-Me, 1-CO₂H, 4-link]<br>((1,2-cis)-(1,4-trans), isomer 4) | +++ | 521 | Free Base |
| 2-25 | CH₃/H | Et | HO₂C–[cyclohexane]<br>(trans isomer, enantiomer 1) | +++ | 467 | Free Base |
| 2-26 | CH₃/H | Et | HO₂C–[cyclohexane]<br>(trans isomer, enantiomer 2) | +++ | 467 | Free Base |

-continued

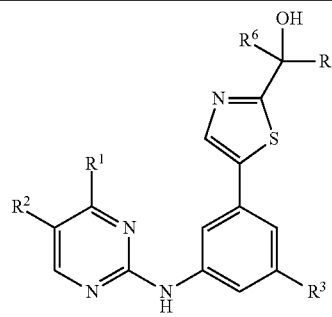

| Ex. | R¹/R² | R⁶ | R | rhSyk Activity | [M + H]+ Obs'd | Form(s) |
|---|---|---|---|---|---|---|
| 2-27 | CHF₂/H | CH₃ | H₃C at position 2, Et—O₂C at position 1, attachment at position 4 ((1,2-cis)-(1,4-trans), isomer 1) | +++ | 531 | Free Base |
| 2-28 | CHF₂/H | CH₃ | H₃C at position 2, HO₂C at position 1, attachment at position 4 ((1,2-cis)-(1,4-trans), isomer 1) | +++ | 503 | Free Base |
| 2-29 | CHF₂/H | CH₃ | H₃C at position 2, HO₂C at position 1, attachment at position 4 ((1,2-cis)-(1,4-trans), isomer 2) | +++ | 503 | Free Base |
| 2-30 | CHF₂/H | CH₃ | H₃C at position 2, HO₂C at position 1, attachment at position 4 ((1,2-cis)-(1,4-trans), isomer 3) | +++ | 503 | Free Base |
| 2-31 | CHF₂/H | CH₃ | H₃C at position 2, HO₂C at position 1, attachment at position 4 ((1,2-cis)-(1,4-trans), isomer 4) | +++ | 503 | Free Base |
| 2-32 | OCH₃/F | CH₃ | H₃C at position 2, Et—O₂C at position 1, attachment at position 4 ((1,2-cis)-(1,4-trans), isomer 1) | ++ | 529 | Free Base |

-continued

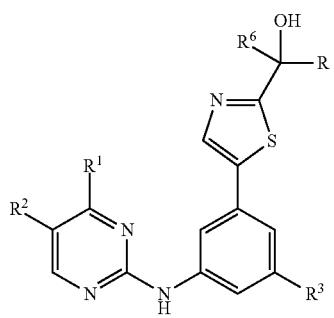

| Ex. | R¹/R² | R⁶ | R | rhSyk Activity | [M + H]+ Obs'd | Form(s) |
|---|---|---|---|---|---|---|
| 2-33 | OCH₃/F | CH₃ | (1,2-cis)-(1,4-trans) cyclohexane with HO₂C at 1, CH₃ at 2, attachment at 4, isomer 1 | +++ | 501 | TFA Salt |
| 2-34 | OCH₃/H | CH₃ | (1,2-cis)-(1,4-trans) cyclohexane with HO₂C at 1, CH₃ at 2, attachment at 4, isomer 1 | +++ | 483 | Free Base |
| 2-35 | CH₃/H | CH₃ | (1,3-cis) cyclobutane with two CH₃ at 2, CH₂CO₂H at 1, attachment at 3, isomer 1 | +++ | 467 | Free Base |
| 2-36 | CF₃/H | CH₃ | (1,3-cis) cyclobutane with two CH₃, CH₂CO₂H at 1, attachment at 3, isomer 1 | +++ | 521 | Free Base |
| 2-37 | CH₃/H | CH₃ | (1,3-cis) cyclobutane with two CH₃, CH₂CO₂H at 1, attachment at 3, isomer 2 | +++ | 467 | Free Base |
| 2-38 | CF₃/H | CH₃ | (1,3-cis) cyclobutane with two CH₃, CH₂CO₂H at 1, attachment at 3, isomer 2 | +++ | 521 | Free Base |

-continued

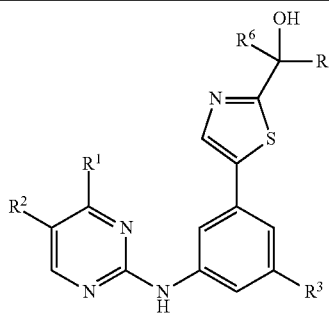

| Ex. | R¹/R² | R⁶ | R | rhSyk Activity | [M + H]+ Obs'd | Form(s) |
|---|---|---|---|---|---|---|
| 2-39 | CF₃/H | CH₃ | H₃C, CH₃ cyclobutyl-CO₂H ((1,3-cis), isomer 3) | +++ | 521 | Free Base |
| 2-40 | CH₃/F | CH₃ | H₃C, CH₃ cyclobutyl-CO₂H ((1,3-cis), isomer 1) | +++ | 485 | Free Base |
| 2-41 | CH₃/H | CH₃ | H₃C, CH₃ cyclobutyl-CO₂H ((1,3-cis), isomer 1) | +++ | 467 | Free Base |
| 2-42 | CF₃/H | CH₃ | H₃C, CH₃ cyclobutyl-CO₂H ((1,3-cis), isomer 4) | +++ | 521 | Free Base |
| 2-43 | CH₃/F | CH₃ | H₃C, CH₃ cyclobutyl-CO₂H ((1,3-cis), isomer 2) | +++ | 485 | Free Base |
| 2-44 | CF₃/H | H | HO₂C-cyclohexyl-OH (trans isomer, enantiomer 1) | +++ | 509 | Free Base |
| 2-45 | CF₃/H | H | HO₂C-cyclohexyl-OH (cis isomer, enantiomer 1) | +++ | 509 | Free Base |

-continued

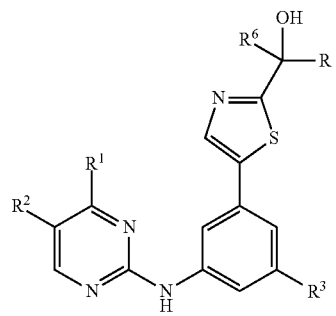

| Ex. | R¹/R² | R⁶ | R | rhSyk Activity | [M + H]+ Obs'd | Form(s) |
|---|---|---|---|---|---|---|
| 2-46 | CF₃/H | H | HO₂C—⟨cyclohexyl⟩—OH (trans isomer, enantiomer 1) | +++ | 509 | Free Base |
| 2-47 | CF₃/H | H | HO₂C—⟨cyclohexyl⟩—OH (trans isomer, enantiomer 2) | +++ | 509 | Free Base |
| 2-48 | CF₃/H | H | HO₂C—⟨cyclohexyl⟩—OH (cis isomer, enantiomer 1) | +++ | 509 | Free Base |
| 2-49 | CF₃/H | H | HO₂C—⟨cyclohexyl⟩—OH (cis isomer, enantiomer 2) | +++ | 509 | Free Base |
| 2-50 | CH₃/H | CH₃ | nBu—OC(O)—⟨cyclohexyl⟩— (trans isomer, racemic) | ++ | 509 | Free Base |
| 2-51 | CH₃/H | CH₃ | HO₂C—⟨cyclohexyl⟩— (trans isomer, racemic) | +++ | 453 | Free Base |
| 2-52 | CH₃/H | CH₃ | HO₂C—⟨cyclohexyl⟩— (trans isomer, enantiomer 1) | +++ | 453 | Free Base |

-continued

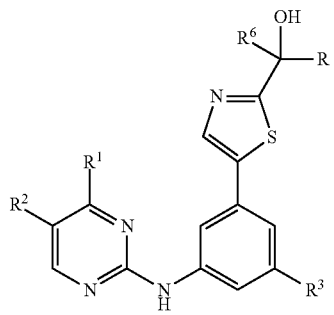

| Ex. | R¹/R² | R⁶ | R | rhSyk Activity | [M + H]+ Obs'd | Form(s) |
|---|---|---|---|---|---|---|
| 2-53 | $CH_3$/H | $CH_3$ | HO₂C—⬡—⌇ (trans isomer, enantiomer 2) | +++ | 453 | Free Base |
| 2-54 | $CH(CH_3)_2$/H | $CH_3$ | HO₂C—⬡—⌇ (trans isomer, enantiomer 1) | +++ | 481 | Ammonium Salt |
| 2-55 | cPr/H | $CH_3$ | HO₂C—⬡—⌇ (trans isomer, enantiomer 1) | +++ | 479 | Ammonium Salt |
| 2-56 | $OCH_3$/H | $CH_3$ | HO₂C—⬡—⌇ (trans isomer, enantiomer 1) | +++ | 469 | Free Base; Ammonium Salt |
| 2-57 | $CH_3$/H | $CH_3$ | Bn(O)₂C-HN—⬡—⌇ (trans isomer, racemic) | ++ | 558 | Free Base |
| 2-58 | $OCH(CH_3)_2$/H | $CH_3$ | HO₂C—⬡—⌇ (trans isomer, enantiomer 1) | +++ | 497 | Ammonium Salt |
| 2-59 | $CH_3$/F | $CH_3$ | HO₂C—⬡—⌇ (trans isomer, enantiomer 1) | +++ | 471 | Ammonium Salt |

-continued

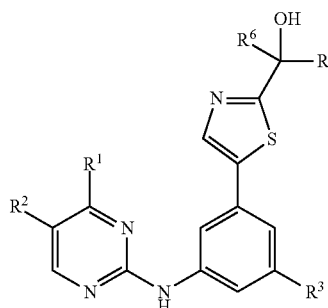

| Ex. | R¹/R² | R⁶ | R | rhSyk Activity | [M + H]+ Obs'd | Form(s) |
|---|---|---|---|---|---|---|
| 2-60 | CH₃/Cl | CH₃ | HO₂C—⟨cyclohexyl⟩— (trans isomer, enantiomer 1) | +++ | 487 | Ammonium Salt |
| 2-61 | OCH₃/F | CH₃ | HO₂C—⟨cyclohexyl⟩— (trans isomer, enantiomer 1) | +++ | 487 | Ammonium Salt |
| 2-62 | OCH₃/Cl | CH₃ | HO₂C—⟨cyclohexyl⟩— (trans isomer, enantiomer 1) | +++ | 503 | Ammonium Salt |
| 2-63 | CH(CH₃)₂/H | CH₃ | HO₂C—⟨cyclohexyl⟩— (trans isomer, enantiomer 2) | +++ | 481 | Ammonium Salt |
| 2-64 | cPr/H | CH₃ | HO₂C—⟨cyclohexyl⟩— (trans isomer, enantiomer 2) | +++ | 479 | Ammonium Salt; TFA salt |
| 2-65 | CF₃/H | CH₃ | NC—⟨cyclohexyl⟩— (trans isomer, racemic) | +++ | 488 | Free Base |
| 2-66 | OCH₃/H | CH₃ | HO₂C—⟨cyclohexyl⟩— (trans isomer, enantiomer 2) | +++ | 469 | Ammonium Salt |

-continued

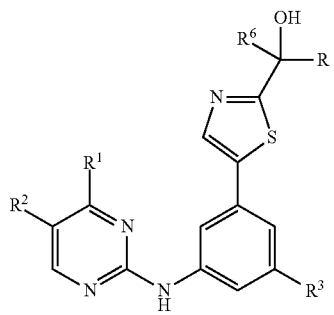

| Ex. | R¹/R² | R⁶ | R | rhSyk Activity | [M + H]+ Obs'd | Form(s) |
|---|---|---|---|---|---|---|
| 2-67 | OCH(CH₃)₂/H | CH₃ | HO₂C—⟨cyclohexyl⟩— (trans isomer, enantiomer 2) | +++ | 497 | Ammonium Salt |
| 2-68 | CH₃/Cl | CH₃ | HO₂C—⟨cyclohexyl⟩— (trans isomer, enantiomer 2) | +++ | 487 | Ammonium Salt |
| 2-69 | OCH₃/F | CH₃ | HO₂C—⟨cyclohexyl⟩— (trans isomer, enantiomer 2) | +++ | 487 | Free Base; Ammonium Salt |
| 2-70 | CH₃/H | CH₃ | NC—⟨cyclohexyl⟩— (trans isomer, racemic) | +++ | 434 | Free Base |
| 2-71 | OCH₃/Cl | CH₃ | HO₂C—⟨cyclohexyl⟩— (trans isomer, enantiomer 2) | +++ | 503 | Ammonium Salt |
| 2-72 | OCH₃/H | CH₃ | nBu—OC(O)—⟨cyclohexyl⟩— (trans isomer, enantiomer 1) | ++ | 525 | Free Base |
| 2-73 | OCH₃/F | CH₃ | nBu—OC(O)—⟨cyclohexyl⟩— (trans isomer, enantiomer 1) | + | 543 | Free Base |

-continued

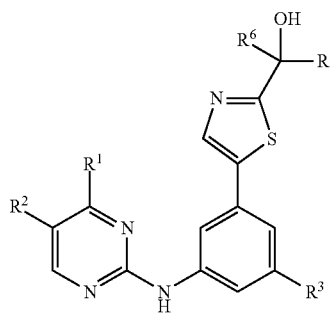

| Ex. | $R^1/R^2$ | $R^6$ | R | rhSyk Activity | $[M+H]^+$ Obs'd | Form(s) |
|---|---|---|---|---|---|---|
| 2-76 | $CHF_2$/H | $CH_3$ | nBu—OC(O)—cyclohexyl— (trans isomer, enantiomer 1) | ++ | 545 | Free Base |
| 2-77 | $CHF_2$/H | $CH_3$ | $HO_2C$—cyclohexyl— (trans isomer, enantiomer 1) | +++ | 489 | Free Base |
| 2-78 | $CHF_2$/H | $CH_3$ | nBu—OC(O)—cyclohexyl— (trans isomer, enantiomer 2) | ++ | 545 | Free Base |
| 2-79 | $CHF_2$/H | $CH_3$ | $HO_2C$—cyclohexyl— (trans isomer, enantiomer 2) | +++ | 489 | Free Base |
| 2-81 | $CF_3$/H | $CH_3$ | —cyclohexyl—$NHSO_2CH_3$ (trans isomer, racemic) | +++ | 556 | Free Base |
| 2-82 | $CH_3$/H | $CH_3$ | —cyclohexyl—$NHSO_2CH_3$ (trans isomer, racemic) | +++ | 502 | Free Base |
| 2-85 | $CF_3$/H | iPr | $HO_2C$—cyclohexyl— (trans isomer, enantiomer 1) | +++ | 535 | Free Base |

-continued

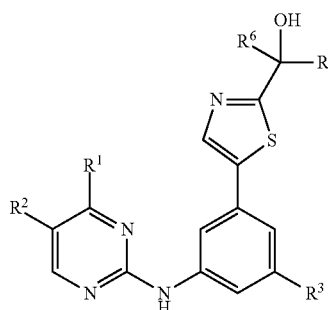

| Ex. | R¹/R² | R⁶ | R | rhSyk Activity | [M + H]+ Obs'd | Form(s) |
|---|---|---|---|---|---|---|
| 2-86 | CF₃/H | iPr | HO₂C—⟨cyclohexyl⟩—⁂ (trans isomer, enantiomer 2) | +++ | 535 | Free Base |
| 2-87 | CH₃/H | CH₃ | H₃C, HO₂C—⟨1,2,4-cyclohexyl⟩—⁂ ((1,2-cis)-(1,4-cis), isomer 1) | +++ | 467 | Free Base |
| 2-88 | CH₃/H | CH₃ | H₃C, HO₂C—⟨1,2,4-cyclohexyl⟩—⁂ ((1,2-cis)-(1,4-cis), isomer 2) | +++ | 467 | Free Base |
| 2-89 | CH₃/H | CH₃ | H₃C, HO₂C—⟨1,2,4-cyclohexyl⟩—⁂ ((1,2-cis)-(1,4-cis), isomer 3) | +++ | 467 | Free Base |
| 2-90 | CH₃/H | CH₃ | H₃C, HO₂C—⟨1,2,4-cyclohexyl⟩—⁂ ((1,2-cis)-(1,4-cis), isomer 4) | +++ | 467 | Free Base |
| 2-95 | CF₃/H | CH₂OH | HO₂C—⟨cyclohexyl⟩—⁂ (trans isomer, racemic) | +++ | 523 | TFA Salt |

-continued

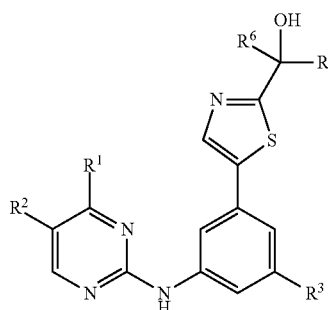

| Ex. | R¹/R² | R⁶ | R | rhSyk Activity | [M + H]+ Obs'd | Form(s) |
|---|---|---|---|---|---|---|
| 2-96 | CH₃/H | CF₃ | HO₂C–⬡–⁓ (trans isomer, racemic) | +++ | 507 | TFA Salt |
| 2-97 | CH₃/H | CH₂OH | HO₂C–⬡–⁓ (trans isomer, racemic) | +++ | 469 | TFA Salt |
| 2-98 | CF₃/H | CH₂OH | HO₂C–⬡–⁓ (trans isomer, enantiomer 1) | +++ | 523 | Free Base |
| 2-99 | CF₃/H | CH₂OH | HO₂C–⬡–⁓ (trans isomer, enantiomer 2) | +++ | 523 | Free Base |
| 2-100 | CH₃/H | CF₃ | HO₂C–⬡–⁓ (trans isomer, enantiomer 1) | +++ | 507 | Free Base |
| 2-101 | CH₃/H | CF₃ | HO₂C–⬡–⁓ (trans isomer, enantiomer 2) | +++ | 507 | Free Base |
| 2-102 | CHF₂/H | CF₃ | HO₂C–⬡–⁓ (trans isomer, enantiomer 1) | +++ | 543 | Free Base |

-continued

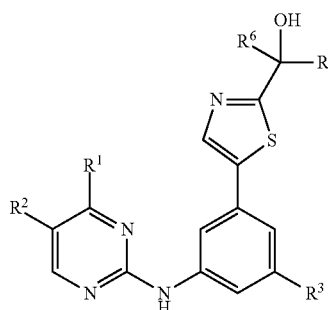

| Ex. | R¹/R² | R⁶ | R | rhSyk Activity | [M + H]+ Obs'd | Form(s) |
|---|---|---|---|---|---|---|
| 2-103 | CHF₂/H | CF₃ | HO₂C—⌬—⌇ (trans isomer, enantiomer 2) | +++ | 543 | Free Base |
| 2-104 | CF₃/H | CF₃ | HO₂C—⌬—⌇ (trans isomer, enantiomer 1) | +++ | 561 | Free Base |
| 2-105 | CF₃/H | CF₃ | HO₂C—⌬—⌇ (trans isomer, enantiomer 2) | +++ | 561 | Free Base |
| 2-106 | CH₃/H | CH₂OH | HO₂C—⌬—⌇ (trans isomer, enantiomer 1) | +++ | 469 | Free Base |
| 2-107 | CH₃/H | CH₂OH | HO₂C—⌬—⌇ (trans isomer, enantiomer 2) | +++ | 469 | Free Base |
| 2-108 | OCH₃/H | CH₂OH | HO₂C—⌬—⌇ (trans isomer, racemic) | +++ | 485 | TFA Salt |
| 2-109 | CH₃/F | CH₂OH | HO₂C—⌬—⌇ (trans isomer, racemic) | +++ | 487 | TFA Salt |

-continued

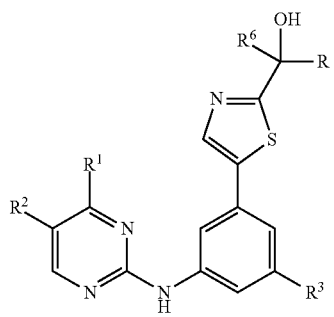

| Ex. | R¹/R² | R⁶ | R | rhSyk Activity | [M + H]+ Obs'd | Form(s) |
|---|---|---|---|---|---|---|
| 2-114 | CH₂F/H | CH₃ | HO₂C—⬡—⁓ (trans isomer, racemic) | +++ | 489 | TFA Salt |
| | | | R³ = H | | | |
| 2-74 | CH₃/H | CH₃ | nBu—OC(O)—⬡—⁓ (trans isomer, enantiomer 1) | + | 495 | Free Base |
| 2-75 | CH₃/H | CH₃ | HO₂C—⬡—⁓ (trans isomer, enantiomer 1) | +++ | 439 | Free Base |
| 2-80 | CF₃/H | iPr | HO₂C—⬡—⁓ (trans isomer, racemic) | +++ | 521 | TFA Salt |
| 2-83 | CF₃/H | iPr | HO₂C—⬡—⁓ (trans isomer, enantiomer 1) | +++ | 521 | Free Base |
| 2-84 | CF₃/H | iPr | HO₂C—⬡—⁓ (trans isomer, enantiomer 2) | +++ | 521 | Free Base |

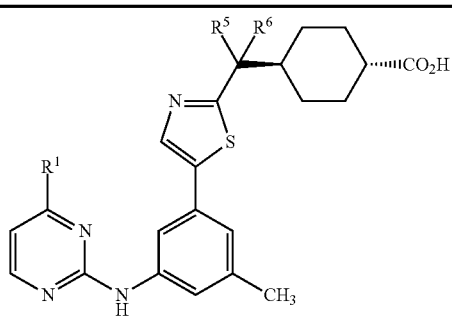

| Ex. | $R^1$ | $R^5$ | $R^6$ | rhSyk Activity | [M + H]+ Obs'd | Form(s) |
|---|---|---|---|---|---|---|
| 2-110* | $CF_3$ | $OCH_3$ | $CH_3$ | +++ | 521 | TFA Salt |
| 2-111** | $CF_3$ | H | $CH_2OH$ | +++ | 507 | TFA Salt |
| 2-112** | $CF_3$ | $NH_2$ | H | +++ | 492 | TFA Salt |
| 2-113** | $CH_3$ | H | $CH_2CH(OH)CH_2OH$ | +++ | 497 | Free Base |

*single enantiomer
**racemic

EXAMPLE 3

-{1-hydroxy-1-[5-(3-methyl-5-{[4-(trifluoromethyl)pyrimidin-2-yl]amino}phenyl)-1,3-thiazol-2-yl]ethyl}-1-methylcyclohexanecarboxylic acid

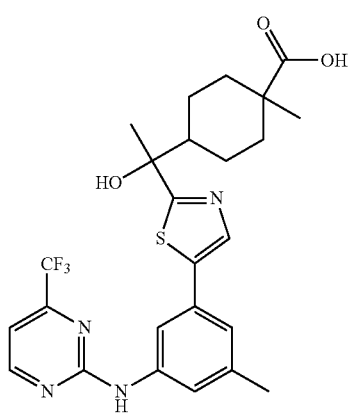 [SMILES: Cc1cc(Nc2nccc(C(F)(F)F)n2)cc(-c2cnc(C(C)(O)C3CCC(C)(C(=O)O)CC3)s2)c1]

Step 1: A solution of N-(3-bromo-5-methylphenyl)-4-(trifluoromethyl)pyrimidin-2-amine (41 mg, 0.123 mmol), Cataxium A (8.9 mg, 0.025 mmol), tris(dibenzylideneacetone)dipalladium(0) (5.7 mg, 0.0062 mmol), pivalic acid (0.006 mL, 0.049 mmol) and methyl 4-[1-hydroxy-1-(1,3-thiazol-2-yl)ethyl]-1-methylcyclohexanecarboxylate (peak 3) (51.2 mg, 0.370 mmol) in dimethylacetamide (0.55 mL) was heated at 125° C. for 24 hours. The reaction mixture was then allowed to cool to room temperature and diluted with diethyl ether (10 mL), ethyl acetate (20 mL) and saturated aqueous sodium bicarbonate solution (10 mL). The layers were separated and the organic layer was washed with water (3×10 mL) and brine (10 mL), dried over sodium sulfate, filtered and concentrated under reduced pressure. The residue was purified by chromatography on silica gel (20-50% ethyl acetate/hexanes) to provide methyl 4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanecarboxylate. MS ESI calc'd. for $C_{26}H_{30}F_3N_4O_3S$ [M+H]$^+$ 535. found 535. $^1$H NMR (500 MHz, CDCl$_3$) δ 8.66 (d, J=4.9 Hz, 1H), 7.91 (s, 1H), 7.87 (s, 1H), 7.34 (s, 1H), 7.27 (s, 1H), 7.10 (s, 1H), 7.06 (d, J=4.9 Hz, 1H), 3.76 (s, 3H), 3.06 (s, 1H), 2.40 (s, 3H), 1.83-1.66 (m, 6H), 1.65 (s, 3H), 1.50-1.42 (m, 2H), 1.39-1.33 (m, 1H), 1.17 (s, 3H).

Step 2: To a solution of methyl 4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanecarboxylate (37.8 mg, 0.071 mmol) in tetrahydrofuran (0.6 mL) and methanol (1.2 mL) was added sodium hydroxide (1.0 M in water, 0.283 mL, 0.283 mmol). The reaction mixture was irradiated to 160° C. for 5 min in a microwave oven. After cooling to room temperature, hydrochloric acid (2.0 M in water, 0.145 mL, 0.290 mmol) was added. The mixture was partitioned between 10% IPA:CHCl$_3$ and brine, and then the layers were separated. The aqueous layer was extracted with 10% IPA:CHCl$_3$, and the combined organic layers were dried over sodium sulfate, filtered and concentrated under reduced pressure to yield 4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanecarboxylic acid. MS ESI calc'd. for $C_{25}H_{27}F_3N_4O_3S$ [M+H]$^+$ 521. found 521. $^1$H NMR (500 MHz, DMSO-d$_6$) δ 11.99 (s, 1H), 10.24 (s, 1H), 8.83 (d, J=4.9 Hz, 1H), 7.95 (s, 2H), 7.45 (s, 1H), 7.27 (d, J=4.9 Hz, 1H), 7.14 (s, 1H), 5.83 (s, 1H), 2.31 (s, 3H), 1.70-1.38 (m, 6H), 1.48 (s, 3H), 1.36-1.28 (m, 1H), 1.26-1.16 (m, 2H), 1.02 (s, 3H). rhSyk (isomer 3)=+++

The following compounds were prepared using the route shown in Example 3 using the appropriate intermediates. Unless otherwise specified, the terms cis and trans refer to the stereochemistry around the cycloalkyl ring.

| Ex. | R | rhSyk Activity | [M + H]+ Obs'd | Form(s) |
|---|---|---|---|---|
| 3-1 | HO₂C-cyclopentyl (1,3-trans, isomer 1) | +++ | 493 | TFA Salt |
| 3-2 | HO₂C-cyclopentyl (1,3-trans, isomer 2) | +++ | 493 | TFA Salt |
| 3-3 | HO₂C-cyclopentyl (1,3-trans, isomer 3) | +++ | 493 | TFA Salt |
| 3-4 | HO₂C-cyclopentyl (1,3-trans, isomer 4) | +++ | 493 | TFA Salt |
| 3-5 | H₃C, HO₂C-cyclohexyl (isomer 1) | +++ | 521 | Free Base |
| 3-6 | H₃C, HO₂C-cyclohexyl (isomer 2) | +++ | 521 | Free Base |
| 3-7 | H₃C, HO₂C-cyclohexyl (isomer 4) | +++ | 521 | TFA Salt |

EXAMPLE 4 trans-4-{1-fluoro-1-[5-(3-methyl-5-{[4-(trifluoromethyl) pyrimidin-2-yl]amino}phenyl)-1,3-thiazol-2-yl] ethyl}cyclohexanecarboxylic acid

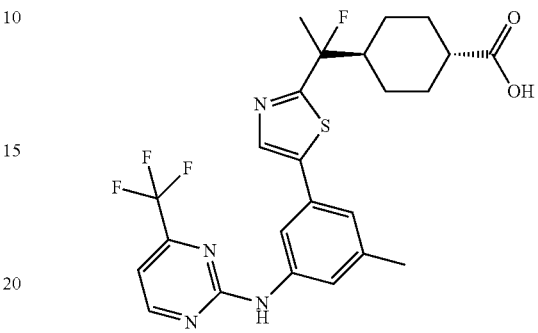

Step 1: To a solution of butyl trans-4-{1-hydroxy-1-[5-(3-methyl-5-{[4-(trifluoromethyl)-pyrimidin-2-yl] amino}phenyl)-1,3-thiazol-2-yl] ethyl}cyclohexanecarboxylate (200 mg, 0.355 mmol) in dichloromethane (1.8 mL) and a catalytic amount of ethanol (1.0 µL, 0.018 mmol) was added deoxofluor (0.33 mL, 1.78 mmol) dropwise. The reaction was stirred for 20 minutes and then the reaction was carefully diluted with water and ethyl acetate. The organic layer was separated, dried over magnesium sulfate, filtered and concentrated in vacuo. The residue was purified by chromatography on silica gel to afford butyl trans-4-{1-fluoro-1-[5-(3-methyl-5-{[4-(trifluoromethyl) pyrimidin-2-yl]amino}phenyl)-1,3-thiazol-2-yl] ethyl}cyclohexanecarboxylate. MS ESI calc'd. for $C_{28}H_{33}F_4N_4O_2S$ [M+H]$^+$ 565. found 565.

Step 2: To a solution of butyl trans-4-{1-fluoro-1-[5-(3-methyl-5-{[4-(trifluoromethyl)-pyrimidin-2-yl] amino}phenyl)-1,3-thiazol-2-yl] ethyl}cyclohexanecarboxylate (80 mg, 0.14 mmol) in methanol (1.5 mL) was added sodium hydroxide (1.0 M in $H_2O$, 0.28 mL, 0.28 mmol) and the reaction was heated to 60° C. overnight. Then, the reaction was cooled to room temperature, acidified to a pH of ~3 with HCl (1.0 M in water) and diluted with water and ethyl acetate. The organic layer was separated, dried over magnesium sulfate, filtered and concentrated in vacuo to afford racemic trans-4-{1-fluoro-1-[5-(3-methyl-5-{[4-(trifluoromethyl)pyrimidin-2-yl] amino}phenyl)-1,3-thiazol-2-yl] ethyl}cyclohexanecarboxylic acid. MS ESI calc'd. for $C_{24}H_{25}F_4N_4O_2S$ [M+H]$^+$ $^{509}$. found 509. $^1$H NMR (500 MHz, DMSO-d₆) 12.01 (s, 1H), 10.28 (s, 1H), 8.84 (d, J=4.8, 1H), 8.07 (d, J=3.3, 1H), 8.02 (s, 1H), 7.47 (s, 1H), 7.29 (d, J=4.9, 1H), 7.19 (s, 1H), 2.32 (s, 3H), 2.16-2.01 (m, 1H), 2.00-1.87 (m, 4H), 1.85 (s, 1H), 1.67 (s, 3H), 1.35-1.19 (m, 4H).

The following compounds were prepared using the route shown in Example 4 using the appropriate intermediates. Unless otherwise specified, the terms cis and trans refer to the stereochemistry around the cycloalkyl ring.

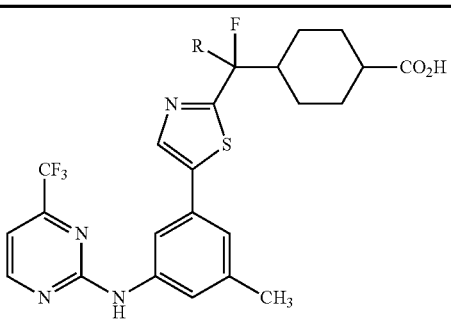

| Ex. | R | rhSyk Activity | [M + H]+ Obs'd | Form(s) |
|---|---|---|---|---|
| 4-1 | CH₃ (trans isomer, enantiomer 1) | +++ | 509 | Free Base |
| 4-2 | H (mixture of cis and trans isomers) | +++ | 495 | TFA Salt |
| 4-3 | H (trans isomer, enantiomer 1) | +++ | 495 | TFA Salt |
| 4-4 | H (trans isomer, enantiomer 2) | +++ | 495 | TFA Salt |
| 4-5 | H (cis isomer, enantiomer 1) | +++ | 495 | TFA Salt |
| 4-6 | H (cis isomer, enantiomer 2) | +++ | 495 | TFA Salt |

EXAMPLE 5 trans-4-hydroxy-4-[(5-{3-methyl-5-[(4-methylpyrimidin-2-yl)amino]phenyl}-1,3-thiazol-2-yl)methyl]cyclohexanecarboxylic acid cis-4-hydroxy-4-[(5-{3-methyl-5-[(4-methylpyrimidin-2-yl)amino]phenyl}-1,3-thiazol-2-yl)methyl]cyclohexanecarboxylic acid

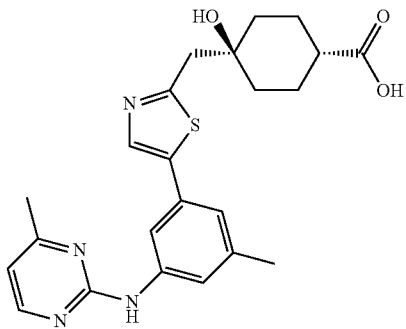

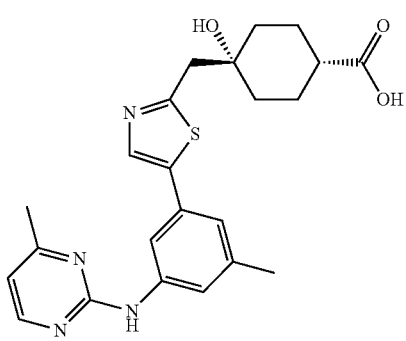

Step 1: To a solution of 2-methylthiazole (1.0 g, 10.1 mmol) in THF (101 mL) at −78° C. was added n-butyllithium (2.5 M in hexanes, 6.05 mL, 15.1 mmol) and the solution was stirred for 30 minutes at −78° C. A solution of tert-butyl 4-oxocyclohexanecarboxylate (2.4 g, 12.1 mmol) in THF (5 mL) was added in one portion and the reaction was maintained at −78° C. for one hour. The reaction was then diluted with water and allowed to warm to room temperature. The mixture was then further diluted with water and ethyl acetate and the organic layer was separated, dried over magnesium sulfate, filtered and concentrated in vacuo. The residue was purified by chromatography on silica gel to afford tert-butyl trans-4-hydroxy-4-(1,3-thiazol-2-ylmethyl)cyclohexanecarboxylate and tert-butyl cis-4-hydroxy-4-(1,3-thiazol-2-ylmethyl)cyclohexanecarboxylate. Characterization for the cis isomer: MS ESI calc'd. for $C_{15}H_{24}N_2O_3S$ [M+H]⁺ 298. found 298. ¹H NMR (500 MHz, DMSO-$d_6$) δ 7.67 (d, J=3.3 Hz, 1H), 7.54 (d, J=3.3 Hz, 1H), 4.52 (s, 1H), 3.01 (s, 2H), 2.10-1.99 (m, 1H), 1.69-1.44 (m, 7H), 1.42-1.26 (m, 10H). Characterization for the trans isomer: MS ESI calc'd. for $C_{15}H_{23}N_2O_3S$ [M+H]⁺ 298. found 298. ¹H NMR (500 MHz, DMSO-$d_6$) δ 7.66 (d, J=3.3 Hz, 1H), 7.54 (d, J=3.3 Hz, 1H), 4.70 (s, 1H), 3.07 (s, 2H), 2.30-2.14 (m, 1H), 1.83-1.65 (m, 2H), 1.63-1.43 (m, 5H), 1.43-1.26 (m, 10H).

Step 2: To a solution of tert-butyl trans-4-hydroxy-4-(1,3-thiazol-2-ylmethyl)cyclohexane-carboxylate (192 mg, 0.646 mmol) in DMF (6.5 mL) was added N-bromosuccinimide (149 mg, 0.839 mmol) and the reaction was stirred for one hour at room temperature. At that time, more N-bromosuccinimide (149 mg, 0.839 mmol) was added and the reaction was stirred for 3 hours. The reaction was then diluted with water and ethyl acetate. The organic layer was separated, dried over magnesium sulfate, filtered and concentrated in vacuo. The residue was purified by column chromatography on silica gel to afford tert-butyl trans-4-[(5-bromo-1,3-thiazol-2-yl)methyl]-4-hydroxycyclohexanecarboxylate. MS ESI calc'd. for $C_{15}H_{23}BrNO_3S$ [M+H]⁺ 376, 378. found 376, 378. ¹H NMR (600 MHz, CDCl₃) δ 7.59 (s, 1H), 3.12 (s, 2H), 2.40-2.23 (m, 1H), 1.96-1.84 (m, 2H), 1.71-1.59 (m, 3H), 1.58-1.45 (m, 3H), 1.42 (s, 9H).

Step 3: To a flask containing 4-methyl-N-[3-methyl-5-(4,4,5,5-tetramethyl-1,3,2-dioxaborolan-2-yl)phenyl]pyrimidin-2-amine (145 mg, 0.446 mmol), tert-butyl trans-4-[(5-bromo-1,3-thiazol-2-yl)methyl]-4-hydroxycyclohexanecarboxylate (168 mg, 0.446 mmol), 1,1'-bis(diphenylphosphino)ferrocenedichloro palladium (II) dichlormethane complex (16 mg, 0.022 mmol) were added degassed 2-methyltetrahydrofuran and sodium carbonate (2 M in water, 0.45 mL, 0.90 mmol). The mixture was then evacuated and purged with argon 5 times. The reaction was then heated at 80° C. overnight. The reaction was then cooled to room temperature and diluted with water and ethyl acetate. The organic layer was separated, dried over magnesium sulfate, filtered and concentrated in vacuo. The residue was purified by chromatography on silica gel to afford tert-butyl trans-4-hydroxy-4-[(5-{3-methyl-5-[(4-methylpyrimidin-2-yl)amino]phenyl}-1,3-thiazol-2-yl)methyl]cyclohexanecarboxylate. MS ESI calc'd. for $C_{27}H_{35}N_4O_3S$ [M+H]⁺ 495. found 495. ¹H NMR (500 MHz, DMSO-$d_6$) δ 9.57 (s, 1H), 8.34 (d, J=5.0 Hz, 1H), 7.96 (s, 1H), 7.91 (s, 1H), 7.52 (s, 1H), 7.03 (s, 1H), 6.74 (d, J=5.0 Hz, 1H), 4.78 (s, 1H), 3.07 (s, 2H), 2.36 (s, 3H), 2.29 (s, 3H), 2.28-2.21 (m, 1H), 1.74 (s, 2H), 1.56 (s, 5H), 1.43-1.32 (m, 10H). rhSyk=++. In a similar manner as above, tert-butyl cis-4-hydroxy-4-[(5-{3-methyl-5-[(4-methylpyrimidin-2-yl)amino]phenyl}-1,3-thiazol-2-yl)methyl]cyclohexanecarboxylate was prepared. MS ESI calc'd. for $C_{27}H_{35}N_4O_3S$ [M+H]⁺ 495. found 495. rhSyk=++.

Step 4: To a solution of tert-butyl trans-4-hydroxy-4-[(5-{3-methyl-5-[(4-methylpyrimidin-2-yl)amino]phenyl}-1,3-thiazol-2-yl)methyl]cyclohexanecarboxylate (103 mg, 0.208 mmol) in methanol (1.0 mL) was added sodium hydroxide (1.0 M in $H_2O$, 1.0 mL, 1.0 mmol) and the reaction was heated to 80° C. overnight. The reaction was then cooled, acidified with HCl (1.0 M in $H_2O$) to a pH of ~3 and then diluted with water and ethyl acetate. The organic layer was separated, dried over magnesium sulfate, filtered and concentrated in vacuo. An epimeric mixture of products was observed. The isomers were separated by supercritical fluid chromatography (chiral OJ column, 4:6 methanol/$CO_2$ with a 4.5 minute run time) to yield trans-4-hydroxy-4-[(5-{3-methyl-5-[(4-methylpyrimidin-2-yl)amino]phenyl}-1,3-thiazol-2-yl)methyl]-cyclohexanecarboxylic acid ($R_t$=2.53 min) and cis-4-hydroxy-4-[(5-{3-methyl-5-[(4-methyl-pyrimidin-2-yl)amino]phenyl}-1,3-thiazol-2-yl)methyl]cyclohexanecarboxylic acid ($R_t$=3.43 min). Characterization data for the trans isomer: MS ESI calc'd. for $C_{23}H_{27}N_4O_3S$ $[M+H]^+$ 439. found 439. $^1$H NMR (500 MHz, DMSO-$d_6$) δ 9.57 (s, 1H), 8.34 (d, J=5.0 Hz, 1H), 7.95 (s, 1H), 7.91 (s, 1H), 7.52 (s, 1H), 7.04 (s, 1H), 6.74 (d, J=5.0 Hz, 1H), 4.78 (s, 1H), 3.08 (s, 2H), 2.36 (s, 3H), 2.29 (s, 3H), 2.28-2.21 (m, 1H), 1.89-1.70 (m, 2H), 1.67-1.48 (m, 4H), 1.46-1.30 (m, 2H). rhSyk=+++

Characterization data for the cis isomer: MS ESI calc'd. For $C_{23}H_{27}N_4O_3S$ $[M+H]^+$ 439. found 439. $^1$H NMR (500 MHz, DMSO-$d_6$) δ 9.57 (s, 1H), 8.34 (d, J=5.0, 1H), 7.96 (s, 1H), 7.92 (s, 1H), 7.52 (s, 1H), 7.04 (s, 1H), 6.74 (d, J=5.0, 1H), 4.59 (s, 1H), 3.01 (s, 2H), 2.36 (s, 3H), 2.29 (s, 3H), 2.10 (s, 1H), 1.75-1.45 (m, 6H), 1.43-1.23 (m, 2H). rhSyk=+++

EXAMPLE 6

2-{[3-(2-{(1R)-1-hydroxy-1-[trans-4-(2H-tetrazol-5-yl)cyclohexyl]ethyl}-1,3-thiazol-5-yl)-5-methylphenyl]amino}-4-(trifluoromethyl)pyrimidin-1-ium trifluoroacetate 2-{[3-(2-{(1S)-1-hydroxy-1-[trans-4-(2H-tetrazol-5-yl)cyclohexyl]ethyl}-1,3-thiazol-5-yl)-5-methylphenyl]amino}-4-(trifluoromethyl)pyrimidin-1-ium trifluoroacetate

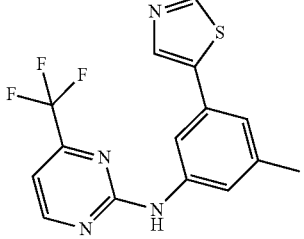

-continued

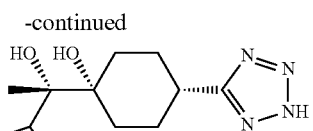

To a solution of trans-4-{1-hydroxy-1-[5-(3-methyl-5-{[4-(trifluoromethyl)pyrimidin-2-yl]amino}phenyl)-1,3-thiazol-2-yl]ethyl}cyclohexanecarbonitrile (214 mg, 0.439 mmol) in DMF (4.4 mL) was added zinc bromide (99 mg, 0.439 mmol) and sodium azide (29 mg, 0.439 mmol) and the reaction was heated overnight to 130° C. The reaction was then cooled to room temperature and diluted with a small amount of water. DMSO (2 mL) was added and the solution was purified by reverse phase HPLC to afford racemic 2-{[3-(2-{1-hydroxy-1-[trans-4-(2H-tetrazol-5-yl)cyclohexyl]ethyl}-1,3-thiazol-5-yl)-5-methylphenyl]amino}-4-(trifluoromethyl)pyrimidin-1-ium trifluoroacetate. The enantiomers were separated by supercritical fluid chromatography (chiral OJ column, 2:8 methanol/$CO_2$ with a 12 minute run time) to yield 2-{[3-(2-{(1R)-1-hydroxy-1-[trans-4-(2H-tetrazol-5-yl)cyclohexyl]ethyl}-1,3-thiazol-5-yl)-5-methylphenyl]amino}-4-(trifluoromethyl)pyrimidin-1-ium trifluoroacetate and 2-{[3-(2-{(1S)-1-hydroxy-1-[trans-4-(2H-tetrazol-5-yl)cyclohexyl]ethyl}-1,3-thiazol-5-yl)-5-methylphenyl]amino}-4-(trifluoromethyl)pyrimidin-1-ium trifluoroacetate. Characterization for the faster eluting enantiomer ($R_t$=6.38 min): MS ESI calc'd. for $C_{24}H_{27}F_3N_8OS$ $[M+H]^+$ 531. found 531. $^1$H NMR (500 MHz, DMSO-$d_6$) δ 10.25 (s, 1H), 8.83 (d, J=4.9, 1H), 7.99-7.94 (m, 2H), 7.46 (s, 1H), 7.27 (d, J=4.9, 1H), 7.15 (s, 1H), 5.90 (s, 1H), 2.90-2.71 (m, 1H), 2.31 (s, 3H), 2.13-1.88 (m, 3H), 1.83-1.67 (m, 1H), 1.67-1.56 (m, 1H), 1.51 (s, 3H), 1.47-1.31 (m, 3H), 1.29-1.09 (m, 1H). rhSyk=+++. rhSyk (slower eluting enantiomer, $R_t$=8.71 min)= +++

The following compounds were prepared using the route shown in Example 6 using the appropriate intermediates:

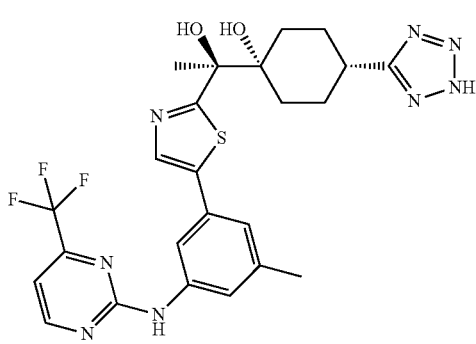

| Ex. | $R^1$ | rhSyk Activity | [M + H]+ Obs'd | Form(s) |
|---|---|---|---|---|
| 6-1 | $CF_3$ (racemic mixture) | +++ | 531 | TFA Salt |
| 6-2 | $CH_3$ (racemic mixture) | +++ | 477 | TFA Salt |

-continued

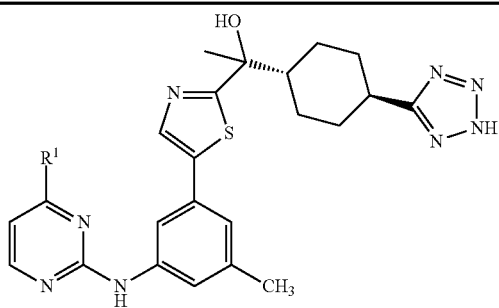

| Ex. | R[1] | rhSyk Activity | [M + H]+ Obs'd | Form(s) |
|---|---|---|---|---|
| 6-3 | CH$_3$ (enantiomer 1) | +++ | 477 | TFA Salt |
| 6-4 | CH$_3$ (enantiomer 2) | +++ | 477 | TFA Salt |

EXAMPLE 7 cis-4-{hydroxy[5-(3-methyl-5-{[4-(trifluoromethyl)pyrimidin-2-yl]amino}phenyl)-1,3-thiazol-2-yl]methyl}cyclohexanecarboxamide trans-4-{hydroxy[5-(3-methyl-5-[4-(trifluoromethyl)pyrimidin-2-yl]amino phenyl)-1,3-thiazol-2-yl]methyl}cyclohexanecarboxamide

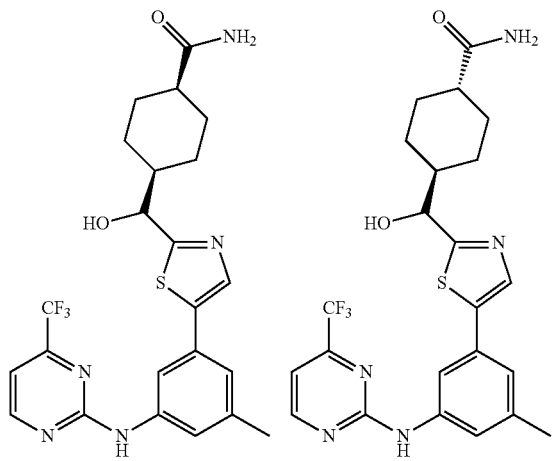

Step 1: A flask containing THF (5 mL) was cooled to −78° C. LDA (1.8 M in THF/heptane/ethylbenzene, 3.3 mL, 5.95 mmol) was added followed by a solution of N-[3-methyl-5-(1,3-thiazol-5-yl)phenyl]-4-(trifluoromethyl)pyrimidin-2-amine (0.50 g, 1.49 mmol) in THF (5 mL) in one portion and the resulting solution was allowed to stir at −78° C. for thirty minutes. A solution of methyl 4-formylcyclohexanecarboxylate (336 mg, 1.93 mmol) in THF (5 mL) was then added in one portion and the resulting solution was stirred for 1 hour at −78° C. The reaction was then diluted with water and allowed to warm to room temperature. The mixture was then further diluted with water and ethyl acetate. The organic layer was separated, dried over magnesium sulfate, filtered and concentrated in vacuo. The residue was purified by chromatography on silica gel to afford methyl 4-{hydroxyl[5-(3-methyl-5-{[4-(trifluoromethyl)pyrimidin-2-yl]amino}phenyl)-1,3-thiazol-2-yl]methyl}cyclohexanecarboxylate as a mixture of 4 isomers. MS ESI calc'd. for $C_{24}H_{25}F_3N_4O_3S$ [M+H]+ 507. found 507. $^1$H NMR (500 MHz, DMSO-$d_6$) δ 10.24 (s, 1H), 8.82 (d, J=5.1, 1H), 7.96 (s, 1H), 7.95 (s, 1H), 7.44 (s, 1H), 7.27 (d, J=4.9, 1H), 7.15 (s, 1H), 6.20 (d, J=5.0, 1H), 3.55 (s, 3H), 2.30 (s, 3H), 1.99 (m, 1H), 1.88 (m, 2H), 1.66 (s, 3H), 1.45 (m, 1H), 1.37-1.15 (m, 3H).

Step 2: To a solution of methyl 4-{hydroxyl[5-(3-methyl-5-{[4-(trifluoromethyl)-pyrimidin-2-yl]amino}phenyl)-1,3-thiazol-2 yl]methyl}cyclohexanecarboxylate in methanol (1.96 mL) was added 1N NaOH (0.79 mL, 0.79 mmol) and the mixture was stirred at room temperature for 16 h. THF (1.96 mL) was added and the mixture was stirred at 60° C. for 6 h, then cooled to room temperature and added HCl (1M in H$_2$O) until the pH=3. The mixture was diluted with 3:1 CHCl$_3$:isopropanol and the organic layers were separated, dried over magnesium sulfate, filtered and concentrated. The residue was purified by column chromatography to afford 4-{hydroxy[5-(3-methyl-5-{[4-(trifluoromethyl)pyrimidin-2-yl]amino}phenyl)-1,3-thiazol-2-yl]methyl}cyclohexanecarboxylic acid as a white solid. The cis and trans isomers were separated by supercritical fluid chromatography (chiral OJ column, 1:3 methanol/CO$_2$ with an 11 minute run time). Characterization data for the cis isomer (Rt=5.15 min): MS ESI calc'd. for $C_{23}H_{24}F_3N_4O_3S$ [M+H]+ 493. found 493. $^1$H NMR (500 MHz, CD$_3$OD) δ 8.69 (d, J=4.8, 1H), 8.00 (s, 1H), 7.91 (s, 1H), 7.43 (s, 1H), 7.11 (s, 1H), 7.10 (s, 1H), 4.68 (d, J=5.1, 1H), 3.34 (s, 1H), 2.36 (s, 3H), 2.20 (m, 1H), 2.02 (m, 2H), 1.84 (m, 2H), 1.70 (m, 1H), 1.50-1.18 (m, 3H). Second eluting enantiomer R$_t$=8.26 min.

Step 3: To a solution of cis-4-{hydroxy[5-(3-methyl-5-{[4-(trifluoromethyl)pyrimidin-2-yl]amino}phenyl)-1,3-thiazol-2-yl]methyl}cyclohexanecarboxylic acid (24 mg, 0.049 mmol), EDC (19 mg, 0.097 mmol), HOBt (13 mg, 0.097 mmol) and diisopropylethyl amine (51 uL, 0.292 mmol) in DMF (1 mL) was added ammonium chloride (7.8 mg, 0.15 mmol) and the mixture was stirred at room temperature for 16 h. The solution was then diluted with water and extracted with ethyl acetate (3×). The organic layers were combined, dried with magnesium sulfate, filtered and concentrated. The residue was purified by column chromatography to afford cis-4-{hydroxy[5-(3-methyl-5-{[4-(trifluoromethyl)pyrimidin-2-yl]amino}phenyl)-1,3-thiazol-2-yl]methyl}cyclohexanecarboxamide as a white solid. MS ESI calc'd. for $C_{23}H_{25}F_3N_5O_2S$ [M+H]+ 492. found 492. $^1$H NMR (500 MHz, DMSO-$d_6$) δ 10.25 (s, 1H), 8.83 (d, J=4.9, 1H), 7.96 (s, 2H), 7.45 (s, 1H), 7.27 (d, J=4.9, 1H), 7.16 (s, 1H), 7.13 (s, 1H), 6.68 (s, 1H), 6.14 (d, J=4.9, 1H), 4.76-4.56 (m, 1H), 3.15 (d, J=5.2, 1H), 2.31 (s, 3H), 2.24 (s, 1H), 1.86 (d, J=5.9, 2H), 1.73 (s, 1H), 1.67 (d, J=8.6, 1H), 1.49-1.31 (m, 4H). rhSyk=+++

In a similar manner as above, trans-4-{hydroxy[5-(3-methyl-5-{[4-(trifluoromethyl)pyrimidin-2-yl]amino}phenyl)-1,3-thiazol-2-yl]methyl}cyclohexanecarboxamide was prepared. MS ESI calc'd. For $C_{23}H_{24}F_3N_5O_2S$ [M+H]+ 492. found 492. rhSyk=+++.

EXAMPLE 8 trans-4-[(1R or 1S)-1-(5-{2-bromo-3-methyl-5-[(4-methylpyrimidin-2-yl)amino]phenyl}-1,3-thiazol-2-yl)-1-hydroxyethyl]cyclohexanecarboxylic acid

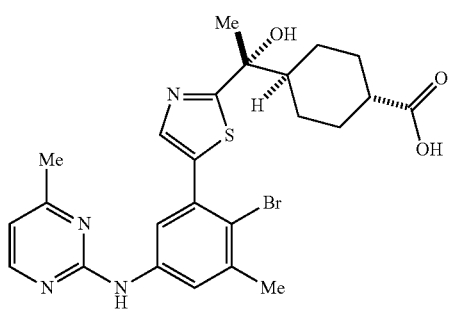 [SMILES: Cc1ccnc(Nc2cc(C)c(Br)c(-c3cnc([C@](C)(O)[C@H]4CC[C@H](C(=O)O)CC4)s3)c2)n1]

N-bromosuccinimide (21.9 mg, 0.123 mmol) was added to a solution of trans-4-[(1R or 1S)-1-hydroxy-1-(5-{3-methyl-5-[(4-methylpyrimidin-2-yl)amino]phenyl}-1,3-thiazol-2-yl)ethyl]cyclohexanecarboxylic acid (50 mg, 0.110 mmol) and DMF (1.2 ml). The mixture was stirred at room temperature for 20 min. Then, saturated sodium thiosulfate solution and 10% IPA in $CHCl_3$ were added. The organic phase was washed with water, dried with sodium sulfate and concentrated in vacuo. The residue was purified on reversed phase HPLC. The product fractions were collected and basified to pH=8, then extracted with EtOAc. The organic phase was washed with water, brine, dried with sodium sulfate and concentrated to afford trans-4-[(1R or 1S)-1-(5-{2-bromo-3-methyl-5-[(4-methylpyrimidin-2-yl)amino]phenyl}-1,3-thiazol-2-yl)-1-hydroxyethyl]cyclohexanecarboxylic acid. MS ESI calc'd. for $C_{24}H_{27}BrN_4O_3S$ [M+H]$^+$ 531. found 531. $^1$H NMR (600 MHz, DMSO-$d_6$). δ 11.94 (s, 1H), 9.68 (s, 1H), 8.33 (d, J=5.0, 1H), 7.84 (s, 1H), 7.80 (s, 1H), 7.73 (s, 1H), 6.75 (d, J=5.0, 1H), 2.35 (s, 3H), 2.34 (s, 3H), 1.95-2.05 (m, 1H), 1.80-1.95 (m, 3H), 1.60-1.68 (m, 1H), 1.50-1.52 (m, 1H), 1.47 (s, 3H), 1.11-1.28 (m, 3H), 0.95-1.08 (m, 1H). rhSyk activity=+++.

The following example was prepared using the route shown in Example 8 using the appropriate intermediates:

Step 1: Methyl(triphenyl)phosphonium bromide (774 mg, 2.166 mmol) was suspended in diethyl ether (5 ml) and potassium tert-butoxide (1.78 M in THF, 1.3 ml, 2.314 mmol) was added at 0° C. dropwise, the suspension was stirred 30 min at same temperature. A solution of ethyl trans-4-[(5-bromo-1,3-thiazol-2-yl)carbonyl]cyclohexanecarboxylate (500 mg, 1.444 mmol) in diethyl ether (1 ml) was added dropwise at 0° C. and the mixture was stirred from 0° C. to 5° C. for 1 h 20 min. The mixture was diluted with saturated ammonium chloride and extracted with EtOAc. The organic phase was washed with water, brine, dried with sodium sulfate and concentrated in vacuo. The residue was purified by chromatography on silica gel (0% to 8% EtOAc in Hexane) to afford ethyl trans-4-[1-(5-bromo-1,3-thiazol-2-yl)ethenyl]cyclohexanecarboxylate as a light yellow oil. MS ESI calc'd. for $C_{14}H_8BrNO_2S$ [M+H]$^+$ 344, 346. found 344, 346.

Step 2: mCPBA (130 mg, 0.582 mmol) was added was added to a solution of ethyl trans-4-[1-(5-bromo-1,3-thiazol-2-yl)ethenyl]cyclohexanecarboxylate (182 mg, 0.529 mmol) in DCM (3 ml) at 0° C. The mixture was then allowed to stir at room temperature for 17 h, diluted with dichlormethane and washed with sodium hydroxide (2M in $H_2O$). The aqueous layer was extracted with DCM and the combined organic layers were washed with brine, dried, concentrated in vacuo.

| Ex. | Structure | rhSyk Activity | [M + H]+ Observed | Form(s) |
|---|---|---|---|---|
| 8-1 | 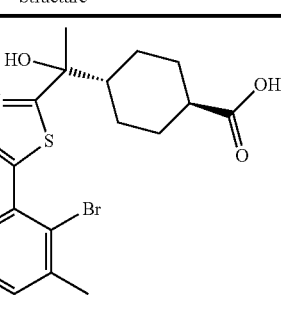<br>enantiomer 1 | +++ | 567.1 | Free Base |

EXAMPLE 9 trans-4-{2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid

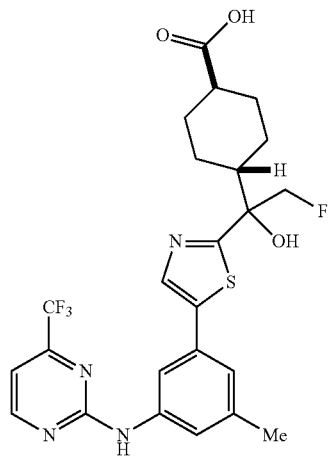 [SMILES: Cc1cc(Nc2nccc(C(F)(F)F)n2)cc(-c2cnc(C(O)(CF)[C@H]3CC[C@H](C(=O)O)CC3)s2)c1]

The residue was purified on silica gel (0-15% EtOAc in hexane) to afford ethyl trans-4-[2-(5-bromo-1,3-thiazol-2-yl)oxiran-2-yl]cyclohexanecarboxylate. MS ESI calc'd. for $C_{14}H_{18}BrNO_3S$ [M+H]$^+$ 360. found 360.

Step 3: To a vial were added ethyl trans-4-[2-(5-bromo-1,3-thiazol-2-yl)oxiran-2-yl]-cyclohexanecarboxylate (101 mg, 0.28 mmol) and tetra-N-butylammonium dihydrogentrifluoride (422 mg, 1.34 mmol). The mixture was heated at 120° C. for 3 h 45 min. The mixture was diluted with water, and extracted with EtOAc. The organic phase was washed with water, brine, dried over sodium sulfate and concentrated to afford racemic ethyl trans-4-[1-(5-bromo-1,3-thiazol-2-yl)-2-fluoro-1-hydroxyethyl]cyclohexane-carboxylate which was used without further purification. MS ESI calc'd. for $C_{14}H_{19}BrFNO_3S$ [M+H]$^+$ 380, 382. found 380, 382.

Step 4: Racemic ethyl trans-4-[1-(5-bromo-1,3-thiazol-2-yl)-2-fluoro-1-hydroxyethyl]cyclohexane-carboxylate (107 mg, 0.281 mmol), N-[3-methyl-5-(4,4,5,5-tetramethyl-1,3,2-dioxaborolan-2-yl)phenyl]-4-(trifluoromethyl)pyrimidin-2-amine (231 mg, 0.610 mmol), X-Phos (56 mg, 0.120 mmol), $Pd_2(dba)_3$ (52 mg, 0.056 mmol), cesium carbonate (429 mg, 1.32 mmol), 1,4-dioxane (3.0 ml) and water (0.3 ml) were combined and the vial was evacuated and purged with nitrogen 3 times then heated to 100° C. for 2 h. The mixture was then filtered and diluted with EtOAc. The organic phase was washed with water, brine, dried over sodium sulfate and concentrated in vacuo. The residue was purified on silica gel (0-10% MeOH in DCM) to afford racemic ethyl trans-4-{2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylate which was used without further purification. MS ESI calc'd. for $C_{26}H_{28}F_4N_4O_3S$ [M+H]+ 553. found 553.

Step 5: Ethyl trans-4-{2-fluoro-1-hydroxy-1-[5-(3-methyl-5-{[4-(trifluoromethyl)-pyrimidin-2-yl]amino}phenyl)-1,3-thiazol-2-yl]ethyl}cyclohexanecarboxylate (72 mg, 0.130 mmol) was dissolved in HCl (10 M in water, 2 ml, 20.0 mmol) and heated to reflux for 20 min. The reaction was diluted with DMSO and purified on reverse phase HPLC (acetonitrile/water with a 0.1% TFA modifier) to afford racemic trans-4-{2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid. MS ESI calc'd. for $C_{24}H_{24}F_4N_4O_3S$ [M+H]+ 525. found 525.

$^1$H NMR (500 MHz, $CD_3OD$) δ 8.71 (d, J=4.8, 1H), 8.01 (s, 1H), 7.96 (s, 1H), 7.46 (s, 1H), 7.12 (d, J=4.9, 2H), 4.78-4.90 (m, 1H), 4.62-4.78 (m, 1H), 2.37 (s, 3H), 2.10-2.20 (m, 1H), 1.90-2.10 (m, 4H), 1.60-1.68 (m, 1H), 1.30-1.50 (m, 3H), 1.10-1.22 (m, 1H). rhSyk activity=+++.

EXAMPLE 10 trans-4-{(1S)-2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid trans-4-{(1R)-2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid

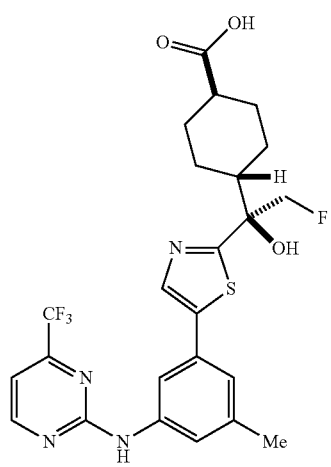

-continued

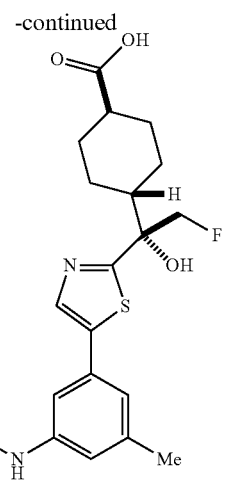

trans-4-{2-Fluoro-1-hydroxy-1-[5-(3-methyl-5-{[4-(trifluoromethyl)pyrimidin-2-yl]amino}-phenyl)-1,3-thiazol-2-yl]ethyl}cyclohexanecarboxylic acid (34.3 mg) was resolved on chiral technology AD-H 2.1×25 cm, 5 uM (mobile phase: 45%/55% Ethanol/$CO_2$, flow rate: 65 mL/Min, wave length: 275 nm, 19.5 min run time) to afford first eluting enantiomer ($R_t$=6.96 mim) and second eluting eantiomer ($R_t$=16.40 min), which are trans-4-{(1S)-2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid and trans-4-{(1R)-2-fluoro-1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid. MS ESI calc'd. for $C_{24}H_{24}F_4N_4O_3S$ [M+H]+ 525. found 525. $^1$H NMR (500 MHz, $CD_3OD$) δ 8.71 (d, J=4.8, 1H), 8.01 (s, 1H), 7.96 (s, 1H), 7.46 (s, 1H), 7.12 (d, J=4.9, 2H), 4.78-4.90 (m, 1H), 4.62-4.78 (m, 1H), 2.37 (s, 3H), 2.10-2.20 (m, 1H), 1.90-2.10 (m, 4H), 1.60-1.68 (m, 1H), 1.30-1.50 (m, 3H), 1.10-1.22 (m, 1H). rhSyk activity=+++.

EXAMPLE 11

N-(3-{2-[(2,2-dimethyl-4-oxocyclohexyl)carbonyl]-1,3-thiazol-5-yl}-5-methylphenyl)-4-(trifluoromethyl)pyrimidin-2-aminium trifluoroacetate

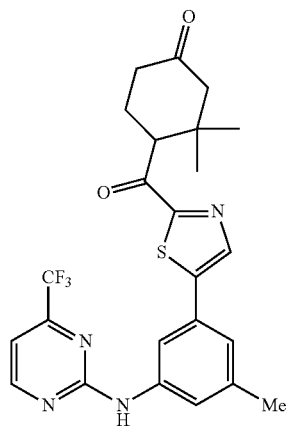 [SMILES: Cc1cc(Nc2nccc(C(F)(F)F)n2)cc(-c2cnc(C(=O)C3CCC(=O)CC3(C)C)s2)c1]

A solution of N,N-diisopropylamine (13.98 mL, 98 mmol) in THF (55 mL) was cooled to −78° C. While at −78° C., n-butyllithium (61.3 mL, 1.6 M in hexanes, 98 mmol) was added to the solution portionwise via syringe, maintaining an internal temperature lower than −65° C. The reaction mixture was warmed to −60° C. and aged for 45 minutes, then cooled back to −78° C. A solution of N-[3-methyl-5-(1,3-thiazol-5-yl)phenyl]-4-(trifluoromethyl)pyrimidin-2-amine (2.113 g, 6.28 mmol) in 55 mL of THF was transferred via cannula (using positive pressure) to the previously described freshly made solution of LDA over the course of 30 minutes, maintaining the internal temperature below −70° C. The reaction was aged at −78° C. for 35 minutes, warmed to −50° C., and aged for another 15 minutes. The mixture was cooled to −70° C. and a solution of methyl 2,2-dimethyl-4-oxocyclohexanecarboxylate (9.04 g, 49.1 mmol) in THF (50 mL) was transferred via cannula (using positive pressure) to the flask containing the lithium salt over the course of 45 minutes, maintaining the internal temperature below −65° C. then aged at −65° C. for 20 minutes. The cold bath was removed and the reaction was allowed to warm to room temperature. The mixture was cooled to 0° C., and the reaction was diluted with ethanol (1 mL) and water (1 mL). The mixture was diluted with EtOAc (1 L) and washed three times with saturated ammonium chloride (total volume of wash 1.5 L). The organic layer was dried over sodium sulfate, filtered, concentrated in vacuo and purified by silica gel column chromatography (0-30% EtOAc:Hexanes), followed by reverse phase high pressure liquid chromatography (acetonitrile/water with 0.1% TFA modifier) to afford racemic N-(3-{2-[(2,2-dimethyl-4-oxocyclohexyl)carbonyl]-1,3-thiazol-5-yl}-5-methylphenyl)-4-(trifluoromethyl)pyrimidin-2-aminium trifluoroacetate. MS ESI calc'd. for $C_{24}H_{24}F_3N_4O_2S$ [M+H]$^+$ 489. found 489. $^1$H NMR (500 MHz, CDCl$_3$) δ 8.65 (d, J=5.0, 1H), 8.19 (s, 1H), 8.12 (s, 1H), 7.32 (s, 1H), 7.20 (s, 1H), 7.11 (d, J=5.0, 1H), 4.22 (t, J=6.5, 1H), 2.65-2.55 (m, 2H), 2.44 (s, 3H), 2.43-2.30 (m, 2H), 2.19 (dd, J=13.8, 6.6, 2H), 1.09 (s, 3H), 1.07 (s, 3H). rhSyk activity=++.

EXAMPLE 12

4-{hydroxy[5-(3-methyl-5-{[4-(trifluoromethyl)pyrimidin-2-yl]amino}phenyl)-1,3-thiazol-2-yl]methyl}-3,3-dimethylcyclohexanol

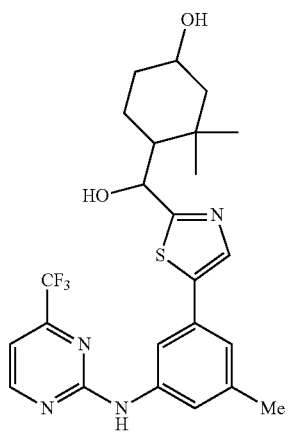 [SMILES: Cc1cc(Nc2nccc(C(F)(F)F)n2)cc(-c2cnc(C(O)C3CCC(O)CC3(C)C)s2)c1]

N-(3-{2-[(2,2-Dimethyl-4-oxocyclohexyl)carbonyl]-1,3-thiazol-5-yl}-5-methylphenyl)-4-(trifluoromethyl)pyrimidin-2-aminium trifluoroacetate (100 mg, 0.166 mmol) was dissolved in methanol (1.66 mL) and cooled to 0° C. Sodium borohydride (18.8 mg, 0.498 mmol) was added to the reaction, and the resultant mixture was aged at 0° C. for 30 minutes. The reaction was quenched with water and extracted with EtOAc (3×). The combined organic layers were concentrated in vacuo and purified via silica gel column chromatography to provide 4-{hydroxy[5-(3-methyl-5-{[4-(trifluoromethyl)pyrimidin-2-yl]amino}phenyl)-1,3-thiazol-2-yl]methyl}-3,3-dimethylcyclohexanol. MS ESI calc'd. for $C_{24}H_{28}F_3N_4O_2S$ [M+H]$^+$ 493. found 493. Mixture present as a ~4:1 mixture of diastereomers. $^1$H NMR data reported as the observed integrals for each peak. $^1$H NMR (500 MHz, CDCl$_3$) δ 8.62 (d, J=4.9, 1H), 7.77 (m, 2H), 7.62 (m, 1H), 7.28 (m, 1H), 7.04-7.00 (m, 2H), 5.07 (d, J=7.2, 0.8H), 4.94 (d, J=7.2, 0.2H), 3.98-3.91 (m, 0.8H), 3.72-3.64 (m, 0.2H), 2.34 (m, 3H), 1.77-1.20 (m, 6H), 1.21 (s, 0.6H), 1.16 (s, 2.4H), 1.12 (s, 2.4H), 0.95 (s, 0.6H). rhSyk activity=+++.

EXAMPLE 13 trans- and cis-4-[(5-{3-methyl-5-[(4-methylpyrimidin-2-yl)amino]phenyl}-1,3-thiazol-2-yl)methyl]cyclohexanecarboxylic acid

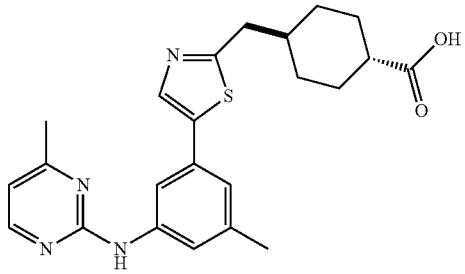

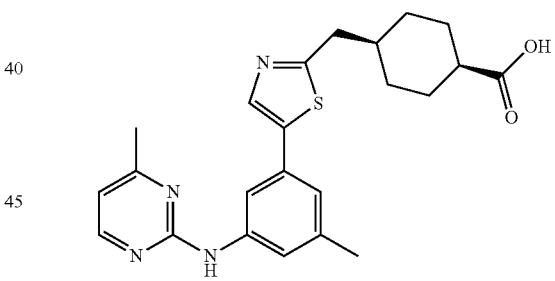

Step 1: Ethyl 4-[(5-bromo-1,3-thiazol-2-yl)methylidene]cyclohexanecarboxylate (223 mg, 0.676 mmol), 4-methyl-N-[3-methyl-5-(4,4,5,5-tetramethyl-1,3,2-dioxaborolan-2-yl)phenyl]pyrimidin-2-amine (220 mg, 0.676 mmol) and 1,1'-bis(diphenylphosphino)-ferrocenedichloro palladium(II) dichloromethane complex (49.5 mg, 0.068 mmol) were combined in a flask that was then sealed and flushed with nitrogen (2×). Dioxane (4 mL) and sodium carbonate (2 M in water, 1.015 mL, 2.029 mmol) were added, and the reaction was flushed again with nitrogen (2×). The mixture was heated to 80° C. for 1 hour and then cooled to room temperature, diluted with water and extracted with EtOAc (2×). The combined organic layers were washed with brine, dried over magnesium sulfate and concentrated under reduced pressure. Purification of the residue by chromatography on silica gel (5-60% EtOAc in hexanes) afforded ethyl 4-[(5-{3-methyl-5-[(4-methylpyrimidin-2-yl)amino]phenyl}-1,3-thiazol-2-yl)methylidene]cyclohexanecarboxylate as a yellow foam. MS ESI calc'd. for C$_{25}$H$_{29}$N$_4$O$_2$S [M+H]$^+$ 449. found 449. $^1$H NMR (500 MHz, DMSO-d$_6$) δ 9.59 (s, 1H), 8.34 (d, J=5.0, 1H), 8.05 (s, 1H), 8.02 (s, 1H), 7.51 (s, 1H), 7.07 (s, 1H), 6.74 (d, J=5.0 Hz, 1H), 6.46 (s, 1H), 4.06 (q, J=7.1 Hz, 2H), 3.55-3.47 (m, 1H), 3.31 (s, 2H), 2.66-2.57 (m, 1H), 2.44-2.24 (m, 7H), 2.04-1.97 (m, 2H), 1.61-1.46 (m, 2H), 1.17 (t, J=7.1 Hz, 3H).

Step 2: Ethyl 4-[(5-{3-methyl-5-[(4-methylpyrimidin-2-yl)amino]phenyl}-1,3-thiazol-2-yl)methylidene]cyclohexanecarboxylate (175 mg, 0.390 mmol) was taken up in ethanol (5 mL), and palladium on carbon (10% loading, 104 mg, 0.098 mmol) was added. The reaction was purged with hydrogen gas (3×) and stirred under a hydrogen atmosphere (via balloon) overnight at room temperature. The mixture was then filtered through CELITE, concentrated under reduced pressure, and the residue purified by flash chromatography on silica gel (0-50% ethyl acetate in hexanes) to provide ethyl 4-[(5-{3-methyl-5-[(4-methylpyrimidin-2-yl)amino]phenyl}-1,3-thiazol-2-yl)methyl]cyclohexanecarboxylate (yellow gum) as a 3:1 mixture of diastereomers. MS ESI calc'd. for C$_{25}$H$_{31}$N$_4$O$_2$S [M+H]$^+$ 451. found 451. $^1$H NMR (500 MHz, DMSO-d$_6$) δ 9.58 (s, 1H), 8.34 (d, J=5.0, 1H), 7.96 (s, 1H), 7.92 (s, 1H), 7.51 (s, 1H), 7.03 (s, 1H), 6.74 (d, J=5.0 Hz, 1H), 4.06 (q, J=7.1 Hz, 2H), 2.88 (d, J=7.3 Hz, 2H), 2.36 (s, 3H), 2.29 (s, 3H), 1.93-1.83 (m, 4H), 1.62-1.45 (m, 4H), 1.24 (d, J=9.5 Hz, 2H), 1.18-1.14 (m, 3H). rhSyk activity=++

Step 3: Ethyl 4-[(5-{3-methyl-5-[(4-methylpyrimidin-2-yl)amino]phenyl}-1,3-thiazol-2-yl)methyl]cyclohexanecarboxylate (147 mg, 0.326 mmol) was suspended in methanol (2.0 mL) in a microwave vial, and sodium hydroxide (1M in water, 0.652 mL, 0.652 mmol) was added. The reaction was heated to 110° C. for 30 min via microwave irradiation. The reaction was acidified to pH=3-4 with aqueous 1M HCl and extracted with 15% isopropyl alcohol in chloroform (2×). The combined organic layers were dried over magnesium sulfate and concentrated under reduced pressure to afford 4-[(5-{3-methyl-5-[(4-methylpyrimidin-2-yl)amino]phenyl}-1,3-thiazol-2-yl)methyl]cyclohexanecarboxylic acid as an off-white solid in a 2.5:1 mixture of diastereomers.

Diastereomers were separated by chiral SFC (Chiral Technology AS, 2.1×25 cm, 10 uM, 25/75 MeOH/CO$_2$, Flow Rate: 70 mL/min, 10.5 min run time, WL: 220 nm) Elution was observed at 7.26 min and 8.55 min. Pooled fractions of each peak were separately concentrated under reduced pressure.

Faster eluting isomer: cis-4-[(5-{3-methyl-5-[(4-methylpyrimidin-2-yl)amino]phenyl}-1,3-thiazol-2-yl)methyl]cyclohexanecarboxylic acid. MS ESI calc'd. for C$_{23}$H$_{27}$N$_4$O$_2$S [M+H]$^+$ 423. found 423. $^1$H NMR (500 MHz, DMSO-d$_6$) δ 12.07 (s, 1H), 9.58 (s, 1H), 8.34 (d, J=5.0 Hz, 1H), 7.96 (s, 1H), 7.92 (s, 1H), 7.51 (s, 1H), 7.03 (s, 1H), 6.74 (d, J=5.0 Hz, 1H), 2.88 (d, J=7.2 Hz, 2H), 2.44 (s, 1H), 2.36 (s, 3H), 2.29 (s, 3H), 1.86 (s, 3H), 1.60-1.53 (m, 2H), 1.49 (s, 2H), 1.25 (d, J=10.0, 2H). rhSyk activity=+++

Slower eluting isomer: trans-4-[(5-{3-methyl-5-[(4-methylpyrimidin-2-yl)amino]-phenyl}-1,3-thiazol-2-yl)methyl]cyclohexanecarboxylic acid. MS ESI calc'd. for C$_{23}$H$_{27}$N$_4$O$_2$S [M+H]$^+$ 423. found 423. $^1$H NMR (500 MHz, DMSO-d$_6$) δ 12.07 (s, 1H), 9.58 (s, 1H), 8.34 (d, J=5.0, 1H), 7.96 (s, 1H), 7.92 (s, 1H), 7.51 (s, 1H), 7.03 (s, 1H), 6.74 (d, J=5.0 Hz, 1H), 2.85 (d, J=6.9 Hz, 2H), 2.36 (s, 3H), 2.29 (s, 3H), 2.16-2.05 (m, J=12.1 Hz, 1H), 1.87 (br s, 2H), 1.77 (m, 2H), 1.28 (m, 2H), 1.04 (d, J=13.7 Hz, 2H). rhSyk activity=+++

EXAMPLE 14 methyl (1,3-cis, 1,4-trans)-3-hydroxy-2,2-dimethyl-4-{[5-(3-methyl-5-{[4-(trifluoromethyl)-pyrimidin-2-yl]amino}phenyl)-1,3-thiazol-2-yl]carbonyl}cyclopentanecarboxylate

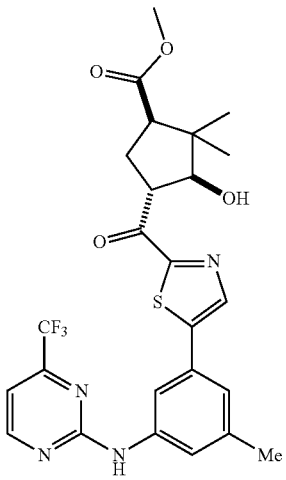

Step 1: Methyl cis-4-hydroxy-2,2-dimethyl-4-[5-(3-methyl-5-{[4-(trifluoromethyl)pyrimidin-2-yl]amino}phenyl)-1,3-thiazol-2-yl]cyclohexanecarboxylate (570 mg, 1.095 mmol) was suspended in Eaton's Reagent (4.14 mL, 21.9 mmol) and heated to 60° C. for 1.5 hours. Then, the reaction was allowed to cool to room temperature and diluted via the slow addition of aqueous saturated sodium bicarbonate and extracted with EtOAc (3×). The combined organic extracts were dried over Na$_2$SO$_4$ and concentrated in vacuo. Purification via silica gel column chromatography (10%-35% EtOAc:hexanes) and separation of the diastereomers via reverse phase high pressure liquid chromatography (acetonitrile/water with 0.1% TFA modifier) gave the desired product as the TFA salt. The residue was diluted with saturated aqueous sodium bicarbonate and extracted with EtOAc (3×). The combined organic layers were dried over Na$_2$SO$_4$ and concentrated in vacuo to give methyl 2,2-dimethyl-4-[5-(3-methyl-5-{[4-(trifluoromethyl)pyrimidin-2-yl]amino}phenyl)-1,3-thiazol-2-yl]cyclohex-3-ene-1-carboxylate. MS ESI calc'd. for C$_{25}$H$_{25}$F$_3$N$_4$O$_2$S [M+H]$^+$ 503. found 503.

Step 2: 2,2-Dimethyl-4-[5-(3-methyl-5-{[4-(trifluoromethyl)pyrimidin-2-yl]amino}phenyl)-1,3-thiazol-2-yl]cyclohex-3-ene-1-carboxylate (34 mg, 0.068 mmol) from step 1 was dissolved in acetone (800 μL) and water (100 μl). Osmium tetroxide (165 μL, 0.027 mmol, 4% in water) and 4-methylmorpholine N-oxide (32 mg, 0.271 mmol) were added sequentially to the reaction, and the suspension was stirred for 40 hours at room temperature. The reaction was diluted with 5% aqueous Na$_2$S$_2$O$_5$ and stirred for 15 minutes. The mixture was extracted with EtOAc (3×), dried over Na$_2$SO$_4$ and concentrated in vacuo. Purification via silica gel column chromatography (20%-75% EtOAc:Hexanes) gave methyl (1,3-cis, 1,4-trans)-3-hydroxy-2,2-dimethyl-4-{[5-(3-methyl-5-[4-(trifluoromethyl)pyrimidin-2-yl]amino phenyl)-1,3-thiazol-2-yl]carbonyl}cyclopentanecarboxylate.

MS ESI calc'd. for C$_{25}$H$_{26}$F$_3$N$_4$O$_4$S [M+H]$^+$ 535. found 535. $^1$H NMR (600 MHz, CDCl$_3$) δ 8.61 (d, J=5.0, 1H), 8.16-8.10 (m, 2H), 7.30 (s, 1H), 7.17 (s, 1H), 7.11 (d, J=5.1, 1H), 3.84-3.74 (m, 2H), 3.72 (s, 3H), 2.62-2.51 (m, 2H), 2.45-2.36 (m, 4H), 1.21 (s, 3H), 0.97 (s, 3H). rhSyk activity=++.

EXAMPLE 15 trans-4-[(1R or 1S)-1-hydroxy-1-{5-[3-(hydroxymethyl)-5-{[4-(trifluoromethyl)pyrimidin-2-yl]amino}phenyl]-1,3-thiazol-2-yl}ethyl]cyclohexanecarboxylic acid

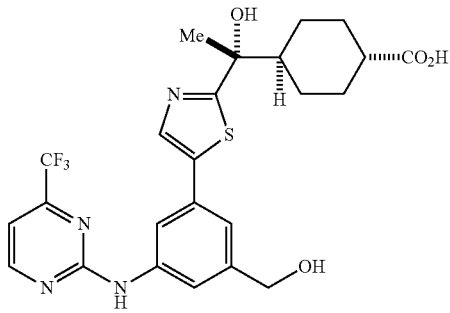 [SMILES: C[C@](O)(c1ncc(-c2cc(CO)cc(Nc3nccc(C(F)(F)F)n3)c2)s1)[C@H]1CC[C@H](C(=O)O)CC1]

Step 1: To a flask containing methyl 3-amino-5-iodobenzoate (250 mg, 0.90 mmol) was added THF (9.0 mL). The solution was cooled to 0° C. and lithium aluminum hydride (1.0M in THF, 1.8 mL, 1.8 mmol) was added slowly and the reaction was allowed to warm to room temperature. Once complete by TLC, the reaction was diluted carefully with water and then ethyl acetate. The organic layer was extracted, dried over magnesium sulfate, filtered and concentrated in vacuo.

Flash chromatography on silica gel afforded [3-(aminomethyl)-5-iodophenyl]methanol. MS ESI calc'd. for $C_7H_{91}NO$: $[M+H]^+$ 250. found 250.

Step 2: To a flask containing the product of Step 1 (109 mg, 0.44 mmol) was added a solution of 2-chloro-4-(trifluoromethyl)pyrimidine (92 mg, 0.50 mmol) in dioxane (1.4 mL). Methanesulfonic acid was added (0.02 mL, 0.37 mmol) and the reaction was heated at 100° C. overnight. The reaction was then cooled to room temperature, diluted with ethyl acetate, washed with brine, dried over magnesium sulfate, filtered and concentrated in vacuo. Flash chromatography on silica gel afforded (3-iodo-5-{[4-(trifluoromethyl)pyrimidin-2-yl]amino}phenyl)methanol. MS ESI calc'd. for $C_{12}H_{10}F_3IN_3O$: $[M+H]^+$ 396. found 396.

Step 3: To a flask containing the product of Step 2 (2.79 g, 7.06 mmol) in DMF (71 mL) were added tert-butyldimethylsilyl chloride (1.60 g, 10.59 mmol), imidazole (0.96 g, 14.12 mmol) and DMAP (86 mg, 0.71 mmol). After two hours, the reaction was diluted with water and ethyl acetate. The organic layer was separated, dried over magnesium sulfate, filtered and concentrated in vacuo. Column chromatography on silica gel afforded N-[3-({[tert-butyl(dimethyl)silyl]oxy}methyl)-5-iodophenyl]-4-(trifluoromethyl)pyrimidin-2-amine. MS ESI calc'd. for $C_{18}H_{24}F_3IN_3OSi$: $[M+H]^+$ 510. found 510.

Step 4: Degassed dioxane (68 mL) was added to a flask containing the product of Step 3 (3.46 g, 6.79 mmol), (bispinacolato)diboron (2.59 g, 10.19 mmol), dicyclohexyl[2',4',6'-tri(propan-2-yl)biphenyl-2-yl]phosphane (324 mg, 0.68 mmol), Pd(OAc)$_2$ (76 mg, 0.34 mmol) and potassium acetate (1.33 g, 13.59 mmol). The solution was evacuated and then purged with argon 5 times and then heated to 85° C. overnight. The solution was cooled, diluted with ethyl acetate, washed with water, dried over magnesium sulfate, filtered and concentrated in vacuo. Flash chromatography on silica gel was used for purification to yield N-[3-({[tert-butyl(dimethyl)silyl]oxy}methyl)-5-(4,4,5,5-tetramethyl-1,3,2-dioxaborolan-2-yl)phenyl]-4-(trifluoromethyl)pyrimidin-2-amine. MS ESI calc'd. for $C_{24}H_{36}BF_3N_3O_3Si$: $[M+H]^+$ 510. found 510.

Step 5: N-(3-((Tert-butyldimethylsilyloxy)methyl)-5-(4,4,5,5-tetramethyl-1,3,2-dioxaborolan-2-yl)phenyl)-4-(trifluoromethyl)pyrimidin-2-amine (30.0 mg, 0.059 mmol), trans-4-[(1R or 1S)-1-(5-bromo-1,3-thiazol-2-yl)-1-hydroxyethyl]cyclohexanecarboxylic acid-(1S,2S)-2-(methylamino)-1-phenylpropan-1-ol (1:1) (35.3 mg, 0.071 mmol), potassium carbonate (24.4 mg, 0.177 mmol) and PdCl$_2$(dppf) (8.62 mg, 0.012 mmol) were placed in a 4-mL vial. The vial was evacuated and back-filled with nitrogen. 1,4-Dioxane (1 mL) and water (0.2 mL) were added and the reaction mixture was heated to 80° C. for 2 hours. TFA (0.5 mL) was added and after gas evolution had ceased, the reaction mixture was passed through a microfilter and the filtrate was directly purified by preparative reverse phase HPLC [(C-18), eluting with acetonitrile/water+0.1% TFA (eluting with 0 to 100% MeCN)], to give trans-4-((R or S)-1-hydroxy-1-(5-(3-(hydroxymethyl)-5-(4-(trifluoromethyl)pyrimidin-2-ylamino)phenyl)thiazol-2-yl)ethyl)-cyclohexanecarboxylic acid TFA salt as a yellow solid. MS ESI calc'd. for $C_{24}H_{25}F_3N_4O_4S$ $[M+H]^+$ 523. found 523. $^1H$ NMR (500 MHz, DMSO-d$_6$) δ 8.83 (d, J=4.9 Hz, 1H), 8.03 (s, 1H), 7.93 (s, 1H), 7.59 (s, 1H), 7.28 (d, J=4.9 Hz, 1H), 7.23 (s, 1H), 4.49 (s, 2H), 2.04-1.84 (m, 4H), 1.66-1.52 (m, 2H), 1.47 (s, 3H), 1.26-1.01 (m, 4H). rhSyk=+++

EXAMPLE 16 trans-4-{(1R or 1S)-[5-(3-cyclopropyl-5-{[4-(trifluoromethyl)pyrimidin-2-yl]amino}phenyl)-1,3-thiazol-2-yl]-1-hydroxyethyl}cyclohexanecarboxylic acid

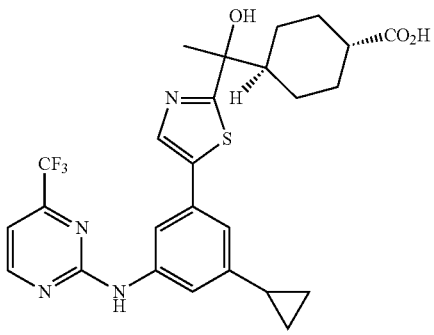 [SMILES: CC(O)(c1ncc(-c2cc(Nc3nccc(C(F)(F)F)n3)cc(C3CC3)c2)s1)[C@H]1CC[C@H](C(=O)O)CC1]

Step 1: To a solution of 3,5-dibromoaniline (4.47 g, 17.8 mmol) and 2-chloro-4-(trifluoromethyl)pyrimidine (2.36 mL, 19.6 mmol) was added p-toluenesulfonic acid (4.06 g, 21.4 mmol), which resulted in the formation of a thick suspension. This mixture was heated to 100° C. overnight, during which point it became a deep red solution. The mixture was diluted with EtOAc (200 mL) and washed with saturated aqueous NaHCO$_3$ (200 mL) and brine (200 mL). The organic layer was dried (Na$_2$SO$_4$), filtered and concentrated in vacuo. The residue was then purified by chromatography on silica gel (100:0 to 85:15 hexanes:EtOAc) to provide N-(3,5-dibromophenyl)-4-(trifluoromethyl)pyrimidin-2-amine as a light yellow solid. MS ESI calc'd. For $C_{11}H_7Br_2F_3N_3$ $[M+H]^+$ 395, 397, 399. found 395, 397, 399.

Step 2: To a solution of the product from Step 1 (2.0 g, 5.0 mmol) in DMSO (10.1 mL) were added 4,4,5,5-tetramethyl-2-(4,4,5,5-tetramethyl-1,3,2-dioxaborolan-2-yl)-1, 3,2-dioxaborolane (1.4 g, 5.5 mmol), potassium acetate (1.48 g, 15.1 mmol) and 1,1'-bis(diphenylphosphino)-ferrocene]dichloropalladium(II) (123 mg, 0.151 mmol), and the mixture was heated to 125° C. for 30 minutes in a microwave apparatus. The mixture was diluted with EtOAc (100 mL) and washed with 1:1 H$_2$O:brine (2×100 mL). The organic layer was dried over Na$_2$SO$_4$, filtered and concentrated in vacuo. The residue was then purified by chromatography on silica gel (100:0 to 70:30 hexanes:EtOAc) to provide N-[3-bromo-5-(4,4,5,5-tetramethyl-1,3,2-dioxaborolan-2-yl)phenyl]-4-(trifluoromethyl)pyrimidin-2-amine as an off-white solid. MS ESI calc'd. For C$_{17}$H$_{19}$BBr$_2$F$_3$N$_3$O$_2$ [M+H]$^+$ 444, 446. found 444, 446.

Step 3: A solution of palladium acetate (19 mg, 0.085 mmol) and butyl di-1-adamantyl phosphine (61 mg, 0.18 mmol) in THF (12.8 mL) was stirred for 15 min. The product from Step 2 (755 mg, 1.70 mmol), 5-bromo-1,3-thiazole (0.760 ml, 8.50 mmol), potassium fluoride (296 mg, 5.10 mmol), and water (4.25 mL) were then added, and the mixture was heated to 75° C. overnight. After cooling to room temperature, the mixture was diluted with EtOAc (100 mL) and washed with brine (100 mL). A bright yellow solid remained undissolved on the walls of the separatory funnel, which was thus rinsed with THF (100 ml). The combined organic extracts were dried over Na$_2$SO$_4$, filtered and concentrated in vacuo. The residue was then purified by chromatography on silica gel (100:0 to 50:50 hexanes:EtOAc) to provide N-[3-bromo-5-(1,3-thiazol-5-yl)phenyl]-4-(trifluoromethyl)pyrimidin-2-amine as an off-white solid. MS ESI calc'd. For C$_{14}$H$_9$Br$_2$F$_3$N$_4$S [M+H]$^+$ 395, 397, 399. found 395, 397, 399.

Step 4: To a flask were added the product from Step 3 (523 mg, 1.30 mmol), cyclopropyl boronic acid (336 mg, 3.91 mmol), potassium phosphate (968 mg, 4.56 mmol), palladium acetate (15 mg, 0.07 mmol) and tricyclohexylphosphine (37 mg, 0.13 mmol). Degassed toluene (10 mL) and water (0.5 mL) were added and the solution was evacuated and then purged with argon 5 times. The mixture was then heated in a microwave apparatus to a temperature of 130° C. for 30 minutes. The reaction was diluted with EtOAc, washed with water, dried over magnesium sulfate, filtered and concentrated in vacuo. The residue was then purified by chromatography on silica gel to afford N-[3-cyclopropyl-5-(1,3-thiazol-5-yl)phenyl]-4-(trifluoromethyl)pyrimidin-2-amine. MS ESI calc'd. For C$_{17}$H$_{14}$F$_3$N$_4$S [M+H]$^+$ 363. found 363. Step 5: A solution of the product from Step 4 (100 mg, 0.276 mmol) in THF (2.8 ml) was cooled to a temperature of −78° C. LDA (2.0 M in THF/heptane/ethylbenzene, 550 µl, 1.100 mmol) was added and the solution was stirred for thirty minutes at that temperature. A solution of trans-butyl 4-acetylcyclohexanecarboxylate (94 mg, 0.414 mmol) in THF (1 mL) was then added to the reaction mixture, and the combined solution was allowed to stir for 1.5 hours at −78° C., at which point the reaction was diluted with MeOH (1 mL). The mixture was concentrated to afford crude trans-butyl 4-((1R or 1S)-(5-(3-cyclopropyl-5-(4-(trifluoromethyl)pyrimidin-2-ylamino)phenyl)thiazol-2-yl)-1-hydroxyethyl)-cyclohexanecarboxylate, which was used in Step 6 without purification. MS ESI calc'd. For C$_{30}$H$_{36}$F$_3$N$_4$O$_3$S [M+H]$^+$ 589. found 589.

Step 6: To a solution of the product from Step 5 (120 mg, 0.204 mmol) in methanol (2 ml) was added sodium hydroxide (1.0 M in water, 1.0 ml, 1.0 mmol). The mixture was heated to a temperature of 80° C. for 45 minutes. The mixture was then cooled to 23° C. and TFA (0.1 ml) was added. The solution was then concentrated and re-suspended in DMSO (2 ml). The resulting residue was purified by reverse phase HPLC (acetonitrile/water with 0.1% TFA modifier) to afford trans-4-((1R or 1S)-(5-(3-cyclopropyl-5-(4-(trifluoromethyl)pyrimidin-2-ylamino)phenyl)-thiazol-2-yl)-1-hydroxyethyl)cyclohexanecarboxylic acid as a TFA salt. MS ESI calc'd. for C$_{26}$H$_{27}$F$_3$N$_4$O$_3$S [M+H]$^+$ 533. found 533. $^1$H NMR (500 MHz, DMSO-d$_6$) δ 10.20 (s, 1H), 8.82 (d, J=4.9 Hz, 1H), 7.96 (s, 1H), 7.83 (s, 1H), 7.40 (s, 1H), 7.27 (d, J=4.9 Hz, 1H), 7.04 (s, 1H), 2.08-1.83 (m, 5H), 1.67-1.50 (m, 2H), 1.47 (s, 3H), 1.28-1.15 (m, 3H), 1.09-0.96 (m, 3H), 0.72-0.69 (m, 2H). rhSyk=+++

EXAMPLE 17 trans-4-{(1R or 1S)-1-[5-(3-fluoro-5-{[4-(trifluoromethyl)pyrimidin-2-yl]amino}phenyl)-1,3-thiazol-2-yl]-1-hydroxyethyl}cyclohexanecarboxylic acid

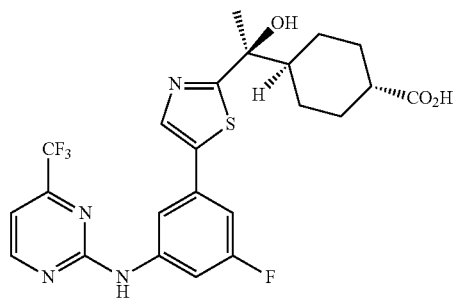 [SMILES: C[C@@](O)(c1ncc(-c2cc(F)cc(Nc3nccc(C(F)(F)F)n3)c2)s1)[C@H]1CC[C@H](C(=O)O)CC1]

Step 1: To a flask containing 3-fluoro-5-(4,4,5,5-tetramethyl-1,3,2-dioxaborolan-2-yl)aniline (3.3 g, 14.00 mmol) and 2-chloro-4-(trifluoromethyl)pyrimidine (2.94 g, 16.10 mmol) were added dioxane (44 mL) and methanesulfonic acid (1.55 g, 16.10 mmol). The reaction mixture was heated at 100° C. overnight. Then, the reaction mixture was cooled to room temperature, diluted with ethyl acetate, washed with water, dried over magnesium sulfate, filtered and concentrated under reduced pressure. The residue was purified by chromatography on silica gel to afford N-[3-fluoro-5-(4,4,5,5-tetramethyl-1,3,2-dioxaborolan-2-yl)phenyl]-4-(trifluoromethyl)pyrimidin-2-amine. MS ESI calc'd. for C$_{17}$H$_{18}$BF$_4$N$_3$O$_2$ [M+H]$^+$ 384. found 384. $^1$H NMR (500 MHz, DMSO-d$_6$) δ 10.41 (s, 1H), 8.85 (d, J=4.9 Hz, 1H), 7.92 (dt, J=2.3 Hz, 12.1, 1H), 7.77 (d, J=1.5 Hz, 1H), 7.32 (d, J=4.9 Hz, 1H), 6.98 (dd, J=2.2 Hz, 8.4, 1H), 1.28 (s, 12H).

Step 2: To a 2-5 mL microwave vial were added N-[3-fluoro-5-(4,4,5,5-tetramethyl-1,3,2-dioxaborolan-2-yl)phenyl]-4-(trifluoromethyl)pyrimidin-2-amine (20 mg, 0.052 mmol), trans-4-[(1R or 1S)-1-(5-bromo-1,3-thiazol-2-yl)-1-hydroxyethyl]cyclohexanecarboxylic acid-(1S,2S)-2-(methylamino)-1-phenylpropan-1-ol (1:1) (26.1 mg, 0.052 mmol), PdCl$_2$(dppf) (7.64 mg, 10.44 µmol), potassium carbonate (21.64 mg, 0.157 mmol), dioxane (870 µl) and water (174 µl). The vial was sealed and placed argon through 3 cycles of evacuation and argon flushing then heated to 80° C. for 2 hours. The resulting mixture was filtered through a CELITE plug and then the solid was washed with EtOAc. The filtrate was concentrated to afford a brown solid. The residue was purified by high pressure liquid chromatography (water/acetonitrile with a 0.1% TFA modifer) and then lyophilized to afford the TFA salt of trans-4-{(1R or 1S)-1-[5-(3-fluoro-5-{[4-(trifluoromethyl)pyrimidin-2-yl]amino}phenyl)-1,3-thiazol-2-yl]-1- hydroxyethyl}cyclohexanecarboxylic acid as a light brown powder. MS ESI calc'd. for $C_{22}H_{23}F_4N_4O_3S$ [M+H]$^+$ 511. found 511. $^1$H NMR (500 MHz, DMSO-d$_6$) δ 11.96 (s, 1H), 10.52 (s, 1H), 8.89 (d, J=4.6 Hz, 1H), 8.07 (s, 1H), 7.85 (s, 1H), 7.65 (d, J=11.3 Hz, 1H), 7.36 (d, J=5.3 Hz, 1H), 7.22 (d, J=8.6 Hz, 1H), 5.88 (s, 1H), 2.09-1.76 (m, 4H), 1.69-1.35 (m, 5H), 1.34-0.91 (m, 4H). rhSyk=+++

EXAMPLE 18 trans-4-((1R or 1S)-{5-[3-(difluoromethyl)-5-{[4-(trifluoromethyl)pyrimidin-2-yl]amino}phenyl]-1,3-thiazol-2-yl}-1-hydroxyethyl)cyclohexanecarboxylic acid

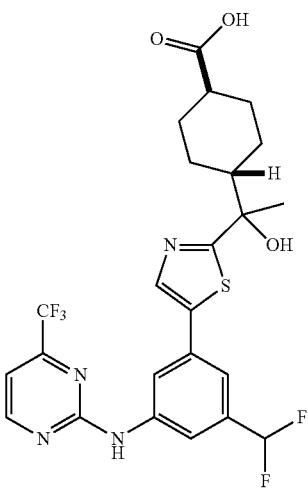 [SMILES: CC(O)(c1ncc(-c2cc(Nc3nccc(C(F)(F)F)n3)cc(C(F)F)c2)s1)[C@H]1CC[C@H](C(=O)O)CC1]

Step 1: 3-Bromo-5-nitrobenzaldehyde (501 mg, 2.178 mmol) was dissolved in DCM (1.7 ml) and cooled to 0° C. Deoxofluor (2 ml, 10.85 mmol) was added dropwise and the reaction was allowed to warm to room temperature and stirred at room temperature for 18 h. The resulting solution was poured into saturated sodium bicarbonate and extracted with dichlormethane. The organic phase was concentrated and purified on silica gel to afford 1-bromo-3-(difluoromethyl)-5-nitrobenzene. $^1$H NMR (500 MHz, CDCl$_3$) δ 8.44 (s, 1H), 8.29 (s, 1H), 7.97 (s, 1H), 6.72 (t, J=55.6, 1H).

Step 2: To a solution of 1-Bromo-3-(difluoromethyl)-5-nitrobenzene (418.4 mg, 1.660 mmol) in EtOH (7 ml) was added water (3.5 ml), iron (500 mg, 8.95 mmol) and ammonium chloride (46 mg, 0.860 mmol). The mixture was then heated to 95° C. for 6 h, diluted with water and extracted with EtOAc. The organic phase was concentrated to afford a residue which was purified on silica gel (hexane/EtOAc=8/2) to afford 3-bromo-5-(difluoromethyl)aniline. MS ESI calc'd. for $C_7H_6BrF_2N$ [M+H]$^+$ 222, 224. found 222, 224. $^1$H NMR (500 MHz, CDCl$_3$) δ 7.02 (s, 1H), 6.87 (s, 1H), 6.68 (s, 1H), 6.49 (t, J=55.6, 1H), 3.86 (s, 2H).

Step 3: A solution of 2-chloro-4-(trifluoromethyl)pyrimidine (0.297 g, 1.626 mmol) in dioxane (4 ml) was added to 3-Bromo-5-(difluoromethyl)aniline (0.314 g, 1.414 mmol) followed by methanesulfonic acid (0.11 ml, 1.694 mmol) and the resulting solution was heated overnight to 100° C. The reaction was diluted with water and extracted with EtOAc. The organic phase was washed with saturated sodium bicarbonate, water, dried over sodium sulfate, filtered and concentrated in vacuo. The residue was purified on silica gel (EtOAc/hexane=2/8) to afford N-[3-bromo-5-(difluoromethyl)phenyl]-4-(trifluoromethyl)pyrimidin-2-amine. MS ESI calc'd. for $C_{12}H_7BrF_5N_3$ [M+H]$^+$ 368, 370. found 368, 370. $^1$H NMR (500 MHz, CDCl$_3$) δ 8.65 (d, J=4.9, 1H), 8.09 (s, 1H), 7.97 (s, 1H), 7.73 (s, 1H), 7.27 (s, 1H), 7.07 (d, J=4.9, 1H), 6.56 (t, J=56.2, 1H).

Step 4: N-[3-bromo-5-(difluoromethyl)phenyl]-4-(trifluoromethyl)pyrimidin-2-amine (443 mg, 1.203 mmol), 4,4,4',4',5,5,5',5'-octamethyl-2,2'-bi-1,3,2-dioxaborolane (458 mg, 1.805 mmol), potassium acetate (354 mg, 3.61 mmol) and PdCl$_2$(dppf)-CH$_2$Cl$_2$ adduct (197 mg, 0.241 mmol) were dissolved in dioxane (5 ml). The mixture was evacuated and purged with nitrogen 5 times and then heated to 100° C. overnight. The mixture was filtered, washed with EtOAc and water. The organic phase was washed with brine, dried over sodium sulfate and concentrated in vacuo. The residue was purified on silica gel (hexane/EtOAc=7/3) to afford N-[3-(difluoromethyl)-5-(4,4,5,5-tetramethyl-1,3,2-dioxaborolan-2-yl)phenyl]-4-(trifluoromethyl)pyrimidin-2-amine. MS ESI calc'd. for $C_{18}H_{20}BF_5N_3O_2$ [M+H]$^+$ 416. found 416.

$^1$H NMR (500 MHz, DMSO-d$_6$) δ 10.39 (s, 1H), 8.84 (d, J=4.9, 1H), 8.20 (s, 1H), 8.12 (s, 1H), 7.47 (s, 1H), 7.30 (d, J=4.9, 1H), 7.04 (t, J=55.9, 1H), 1.28 (s, 12H).

Step 5: To a vial were added trans-4-[(1R or 1S)-1-(5-bromo-1,3-thiazol-2-yl)-1-hydroxyethyl]-cyclohexanecarboxylic acid-(1S,2S)-2-(methylamino)-1-phenylpropan-1-ol (1:1) (115 mg, 0.231 mmol), N-[3-(difluoromethyl)-5-(4,4,5,5-tetramethyl-1,3,2-dioxaborolan-2-yl)phenyl]-4-(trifluoromethyl)pyrimidin-2-amine (80 mg, 0.193 mmol), PdCl$_2$(dppf) (24.4 mg, 0.033 mmol), 1,4-dioxane (2 ml) and sodium carbonate (2 M in water, 0.3 ml, 0.600 mmol). The mixture was evacuated and purged with nitrogen 5 times and then heated to 80° C. for 2 h. The mixture was filtered and purified on reversed phase HPLC (acetonitrile/water with 0.1% TFA modifier) to afford the TFA salt of trans-4-((1R or 1S-{5-[3-(difluoromethyl)-5-{[4-(trifluoromethyl)pyrimidin-2-yl]amino}phenyl]-1,3-thiazol-2-yl}-1-hydroxyethyl)cyclohexanecarboxylic acid. MS ESI calc'd. for $C_{24}H_{24}F_5N_4O_3S$ [M+H]$^+$ 543. found 543. $^1$H NMR (500 MHz, DMSO-d$_6$) δ 10.53 (s, 1H), 8.88 (d, J=4.9, 1H), 8.23 (s, 1H), 8.05 (s, 1H), 7.93 (s, 1H), 7.48 (s, 1H), 7.34 (d, J=4.9, 1H), 7.03 (t, J=55.8, 1H), 1.98-2.08 (m, 1H), 1.80-1.96 (m, 3H), 1.60-1.68 (m, 1H), 1.42-1.58 (m, 1H), 1.48 (s, 3H), 1.15-1.30 (m, 3H), 0.98-1.10 (m, 1H). rhSyk activity=+++.

EXAMPLE 19 trans-4-{(1R or S)-hydroxy-1-[5-(3-methyl-5-{[4-(trifluoromethyl)pyrimidin-2-yl]amino}phenyl)-1,3-thiazol-2-yl]ethyl}cyclohexanecarboxylic acid (Example 1, Faster Eluting Isomer)

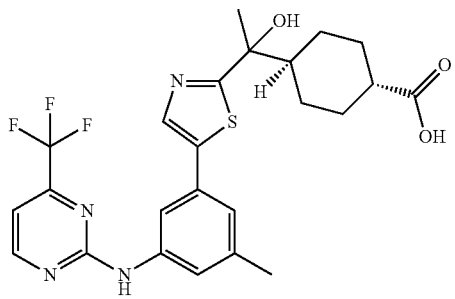 [SMILES: Cc1cc(Nc2nccc(C(F)(F)F)n2)cc(-c2cnc(C(C)(O)[C@H]3CC[C@H](C(=O)O)CC3)s2)c1]

Step 1: To a vented and cooled solution (0° C.) under nitrogen of trans-4-(butoxycarbonyl)cyclohexanecarboxylic acid (*J. Chem. Soc., Perkin Trans.* 1, 1999, 20, 3023) (18.9 g, 83 mmol) in $CH_2Cl_2$ (150 mL) was added a catalytic amount of DMF (30 μL) followed by oxalyl chloride (7.97 mL, 91 mmol). The reaction mixture was then allowed to slowly warm to room temperature where it was stirred for 14 h at which point it was concentrated to a yellow oil and dried under vacuum for 3 h. The residue consisting primarily of butyl trans-4-(chlorocarbonyl)cyclohexanecarboxylate was diluted with THF (200 mL) and cooled in an ice bath. To this solution was added $PdCl_2$(dppf)-$CH_2Cl_2$ (3.38 g, 4.14 mmol, 5 mol %) followed by dimethyl zinc (2 M in $PhCH_3$, 29 mL, 58 mmol, 0.7 equiv) at such a rate that the internal temperature did not exceed 15° C. The cooling bath was then removed and after 2 h of stirring at room temperature the reaction mixture was re-cooled to 0° C. where it was diluted carefully with $H_2O$. After the initial exotherm had subsided, sufficient 1N HCl and EtOAc were introduced such that a homogenous biphasic mixture formed. The layers were separated, the organic washed a second time with $H_2O$ then dried with $MgSO_4$, filtered and concentrated in vacuo. The crude residue was absorbed on silica and purified by flash chromatography to afford butyl trans-4-acetylcyclohexanecarboxylate as a non-viscous orange oil. MS ESI calc'd. for $C_{13}H_{23}O_3$ $[M+H]^+$ 227. found 227. $^1$H NMR (500 MHz, $CDCl_3$) δ 4.06 (t, J=6.6, 2H), 2.37-2.29 (m, 1H), 2.28-2.20 (m, 1H), 2.14 (s, 3H), 2.11-2.02 (m, 2H), 1.99 (d, J=13.8, 2H), 1.66-1.55 (m, 2H), 1.51-1.40 (m, 2H), 1.39-1.29 (m, 4H), 0.93 (t, J=7.4, 3H).

Step 2: To a cooled (0° C.) flask under nitrogen containing iPrMgCl-LiCl (1.3 M in THF, 55.2 mL, 71.8 mmol) was added thiazole (5.10 mL, 71.8 mmol) keeping the internal temperature <10° C. The resulting heterogenous mixture was warmed to RT where it was stirred for 10 min then re-cooled to −20° C. Then, a solution of butyl trans-4-acetylcyclohexanecarboxylate (12.5 g, 55.2 mmol) in THF (20+5 mL) was added via syringe. The cooling bath was then removed and the reaction mixture warmed slowly to 10° C. during which time it was observed to nearly completely homogenize. After 40 min, saturated aqueous $NH_4Cl$ followed by EtOAc were added and the layers separated, the organics dried over $MgSO_4$, filtered and concentrated in vacuo. The crude residue was absorbed on silica and purified by flash chromatograpy to afford Butyl trans-4-[1-hydroxy-1-(1,3-thiazol-2-yl)ethyl]cyclohexanecarboxylate as a light yellow oil. MS ESI calc'd. for $C_{16}H_{26}NO_3S$ $[M+H]^+$ 312. found 312. $^1$H NMR (500 MHz, DMSO-$d_6$) δ 7.67 (d, J=3.3, 1H), 7.51 (d, J=3.3, 1H), 5.73 (s, 1H), 3.95 (t, J=6.5, 2H), 2.16-2.02 (m, 1H), 1.93-1.78 (m, 3H), 1.69-1.56 (m, 1H), 1.54-1.46 (m, 2H), 1.44 (s, 3H), 1.34-1.14 (m, 6H), 0.99 (d, J=15.7, 1H), 0.85 (t, J=7.4, 3H).

Step 3: To a solution of butyl trans-4-[1-hydroxy-1-(1,3-thiazol-2-yl)ethyl]-cyclohexanecarboxylate (10.5 g, 33.7 mmol) in DMF (84 mL) was added NBS (6.90 g, 38.8 mmol) and the resulting mixture heated to 55° C. for 60 min. Then, heating was discontinued and water (30 mL) containing sodium sulfite (2 g) was added to decolorize the reaction mixture which was subsequently further diluted with water and EtOAc. The layers were separated, the organics washed a second time with water, then dried over $MgSO_4$, filtered, and concentrated in vacuo. The crude residue was absorbed on silica and purified by flash chromatography to afford racemic butyl trans-4-[1-(5-bromo-1,3-thiazol-2-yl)-1-hydroxyethyl]cyclohexanecarboxylate as a colorless oil. Butyl trans-4-[1-(5-bromo-1,3-thiazol-2-yl)-1-hydroxyethyl]cyclohexane-carboxylate was then separated by chiral supercritical fluid chromatography (chiral AD-H column, 40:60% methanol:$CO_2$, 12 minute run time) to afford both butyl trans-4-[(1R)-1-(5-bromo-1,3-thiazol-2-yl)-1-hydroxyethyl]cyclohexanecarboxylate and butyl trans-4-[(1S)-1-(5-bromo-1,3-thiazol-2-yl)-1-hydroxyethyl]cyclohexanecarboxylate ($R_t$=5.57 and 7.86 min) in greater then 99% ee. The slower eluting enantiomer ($R_t$=7.86 min) isolated was then used for the rest of the synthesis (absolute stereochemistry unknown). MS ESI calc'd. for $C_{16}H_{25}BrNO_3S$ $[M+H]^+$ 390, 392. found 390, 392. $^1$H NMR (500 MHz, DMSO-$d_6$) δ 7.73 (s, 1H), 5.96 (s, 1H), 3.96 (t, J=6.5, 2H), 2.16-2.04 (m, 1H), 1.93-1.86 (m, 1H), 1.87-1.80 (m, 1H), 1.64-1.54 (m, 1H), 1.54-1.46 (m, 2H), 1.42 (s, 3H), 1.34-1.13 (m, 7H), 1.06-0.92 (m, 1H), 0.85 (t, J=7.4, 3H).

Step 4: 2-Methyl-THF (70 mL) and aqueous $Na_2CO_3$ (2 M, 17.9 mL, 35.9 mmol) were added to a flask and degassed with $N_2$. To that mixture was added N-[3-methyl-5-(4,4,5,5-tetramethyl-1,3,2-dioxaborolan-2-yl)phenyl]-4-(trifluoromethyl)pyrimidin-2-amine (7.48 g, 19.7 mmol), butyl trans-4-[(1R or 1S)-1-(5-bromo-1,3-thiazol-2-yl)-1-hydroxyethyl]cyclohexanecarboxylate ($R_t$=7.86 min, 7 g, 17.9 mmol) and $PdCl_2$(dppf)-$CH_2Cl_2$ (0.73 g, 0.90 mmol, 5 mol %). The resulting mixture was heated to 75° C. where it was stirred for 18 h, then cooled to room temperature, diluted with $H_2O$ and EtOAc and filtered through a pad of CELITE washing with both $H_2O$ and EtOAc. The layers were separated, the aqueous layer back extracted with EtOAc, then the combined organics were dried with $MgSO_4$, filtered, and concentrated in vacuo. The crude residue was absorbed on silica and purified by flash chromatography to afford butyl trans-4-{(1R or S)-hydroxy-1-[5-(3-methyl-5-{[4-(trifluoromethyl)pyrimidin-2-yl]amino}phenyl)-1,3-thiazol-2-yl]ethyl}cyclohexanecarboxylate as a viscous yellow oil. MS ESI calc'd. for $C_{28}H_{34}FN_4O_3S$ $[M+H]^+$ 563. found 563. $^1$H NMR (500 MHz, DMSO-$d_6$) δ 10.24 (s, 1H), 8.83 (d, J=4.9, 1H), 7.98-7.91 (m, 2H), 7.45 (s, 1H), 7.27 (d, J=4.9, 1H), 7.14 (s, 1H), 5.84 (s, 1H), 3.96 (t, J=6.5, 2H), 2.31 (s, 3H), 2.18-2.04 (m, 1H), 1.99-1.79 (m, 2H), 1.64 (s, 1H), 1.60-1.50 (m, 6H), 1.34-1.15 (m, 6H), 1.12-0.95 (m, 1H), 0.85 (t, J=7.4, 3H).

Step 5: Butyl trans-4-{(1R or S)-hydroxy-1-[5-(3-methyl-5-{[4-(trifluoromethyl)pyrimidin-2-yl]amino}phenyl)-1,3-thiazol-2-yl]ethyl}cyclohexanecarboxylate (8.8 g, 15.6 mmol) in MeOH (88 mL) was added NaOH (1.0M in $H_2O$, 54.7 mL, 54.7 mmol) and the resulting heterogenous mixture heated to 70° C. After 1.5 h the reaction mixture was removed from heat and cooled. Upon reaching 55° C. the dropwise addition of HCl (1.0M in $H_2O$, 55 mL, 55 mmol) resulted in crystallization. The heterogeneous mixture was stirred for 3 h at room temperature, then filtered and washed twice with water. The desired product was dried under a nitrogen bag for 14 h to afford trans-4-{(1R or S)-hydroxy-1-[5-(3-methyl-5-{[4-(trifluoromethyl)pyrimidin-2-yl]amino}-phenyl)-1,3-thiazol-2-yl]ethyl}cyclohexanecarboxylic acid as a light yellow solid. MS ESI calc'd. for $C_{24}H_{26}F_3N_4O_3S$ $[M+H]^+$ 507. found 507. $^1$H NMR (500 MHz, DMSO-$d_6$) δ 11.81 (br s, 1H), 10.24 (s, 1H), 8.83 (d, J=4.9, 1H), 7.99-7.92 (m, 2H), 7.45 (s, 1H), 7.27 (d, J=4.9, 1H), 7.14 (s, 1H), 5.82 (s, 1H), 2.31 (s, 3H), 2.10-1.95 (m, 1H), 1.95-1.73 (m, 2H), 1.72-1.58 (m, 1H), 1.58-1.50 (m, 1H), 1.47 (s, 3H), 1.32-1.11 (m, 4H), 1.10-0.94 (m, 1H). rhSyk=+++

EXAMPLE 20 trans-4-[(1R or S)-hydroxy-1-(5-{3-methyl-5-[(4-methylpyrimidin-2-yl)amino]phenyl}-1,3-thiazol-2-yl)ethyl]cyclohexanecarboxylic acid (Compound 2-52)

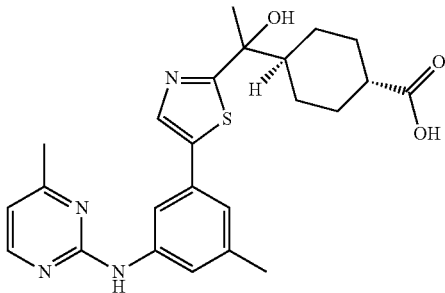 [SMILES: Cc1cc(Nc2nccc(C)n2)cc(-c2cnc(C(C)(O)[C@H]3CC[C@H](C(=O)O)CC3)s2)c1]

Step 1: 2-Methyl-THF (150 mL) and aqueous Na$_2$CO$_3$ (2 M, 38.4 mL, 77 mmol) were added to a flask and degassed with N$_2$. To that mixture was added 4-methyl-N-[3-methyl-5-(4,4,5,5-tetramethyl-1,3,2-dioxaborolan-2-yl)phenyl]pyrimidin-2-amine (13.75 g, 42.3 mmol), butyl trans-4-[(1R or S)-(5-bromo-1,3-thiazol-2-yl)-1-hydroxyethyl]cyclohexanecarboxylate (Ex 19, Step 3, R$_f$=7.86 min) (15 g, 38.4 mmol) and PdCl$_2$(dppf)-CH$_2$Cl$_2$ (1.57 g, 1.92 mmol, 5 mol %). The resulting mixture was heated to 75° C. and stirred for 5 h, then cooled to RT, diluted with H$_2$O and EtOAc then filtered through a pad of CELITE washing with both H$_2$O and EtOAc. The layers were separated, the aqueous layer back extracted with EtOAc, then the combined organics were dried over MgSO$_4$, filtered, and concentrated in vacuo. The crude residue was absorbed on silica and purified by flash chromatography to afford butyl trans-4-[(1R or S)-hydroxy-1-(5-{3-methyl-5-[(4-methylpyrimidin-2-yl)amino]phenyl}-1,3-thiazol-2-yl)ethyl]cyclohexanecarboxylate (84 wt %) as a viscous yellow oil. C$_{28}$H$_{37}$N$_4$O$_3$S [M+H]$^+$ 509. found 509. $^1$H NMR (500 MHz, DMSO-d$_6$) δ 9.57 (s, 1H), 8.34 (d, J=5.0, 1H), 7.95 (s, 1H), 7.92 (s, 1H), 7.51 (s, 1H), 7.04 (s, 1H), 6.74 (d, J=5.0, 1H), 5.83 (s, 1H), 3.96 (t, J=6.5, 2H), 2.36 (s, 3H), 2.29 (s, 3H), 2.18-2.08 (m, 1H), 1.96-1.82 (m, 4H), 1.71-1.59 (m, 1H), 1.58-1.43 (m, 5H), 1.35-1.17 (m, 6H), 0.85 (t, J=7.4, 3H).

Step 2: To a solution of butyl trans-4-[(1R or S)-hydroxy-1-(5-{3-methyl-5-[(4-methyl-pyrimidin-2-yl)amino]phenyl}-1,3-thiazol-2-yl)ethyl]cyclohexanecarboxylate (21.8 g, 84 wt %, 35 mmol) in MeOH (212 mL) was added 1N NaOH (122 mL, 122 mmol) and the resulting heterogenous mixture heated to 70° C. After 1.5 h, the reaction mixture was removed from heat and cooled to 55° C. Then, dropwise addition of 1N HCl (122 mL, 122 mmol) was initiated resulting in crystallization. The heterogeneous mixture was stirred for 2 h at room temperature, then filtered and washed twice with water. The desired product was dried under a nitrogen bag for 14 h to afford trans-4-[(1R or S)-hydroxy-1-(5-{3-methyl-5-[(4-methylpyrimidin-2-yl)amino]-phenyl}-1,3-thiazol-2-yl)ethyl]cyclohexanecarboxylic acid as a white solid. This material was then taken up in EtOAc (300 mL) and the resulting slurry heated to 55° C. and stirred for 1 h. After cooling to room temperature the mixture was filtered and the cake washed with hexanes, then dried under a nitrogen bag for 18 h to afford trans-4-[(1R or S)-hydroxy-1-(5-{3-methyl-5-[(4-methylpyrimidin-2-yl)amino]phenyl}-1,3-thiazol-2-yl)ethyl]cyclohexanecarboxylic acid as a white solid. MS ESI calc'd. for C$_{24}$H$_{29}$N$_4$O$_3$S [M+H]$^+$ 453. found 453. $^1$H NMR (500 MHz, DMSO-d$_6$) δ 11.96 (s, 1H), 9.57 (s, 1H), 8.34 (d, J=5.0, 1H), 7.95 (s, 1H), 7.92 (s, 1H), 7.51 (s, 1H), 7.04 (s, 1H), 6.74 (d, J=5.0, 1H), 5.82 (s, 1H), 2.36 (s, 3H), 2.29 (s, 3H), 2.08-1.98 (m, 1H), 1.95-1.79 (m, 4H), 1.63 (s, 1H), 1.52 (s, 1H), 1.47 (s, 3H), 1.28-1.12 (m, J=11.2, 2H), 1.09-0.96 (m, 1H). rhSyk=+++

EXAMPLE 21 trans-4-{(1R or S)-[5-(3-{[4-(difluoromethyl)pyrimidin-2-yl]amino}-5-methylphenyl)-1,3-thiazol-2-yl]-1-hydroxyethyl}cyclohexanecarboxylic acid (Compound 2-77)

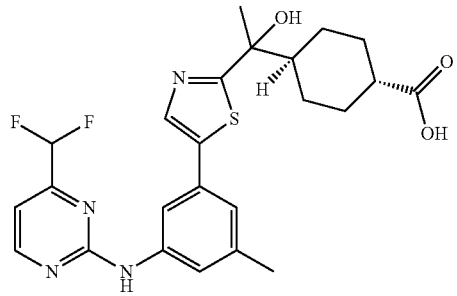 [SMILES: Cc1cc(Nc2nccc(C(F)F)n2)cc(-c2cnc(C(C)(O)[C@H]3CC[C@H](C(=O)O)CC3)s2)c1]

Step 1: A three neck flask containing difluoroacetic anhydride (72.9 mL, 586 mmol) and dichloromethane (488 mL) was cooled to −30° C. A mixture of pyridine (52.1 ml, 645 mmol) and ethyl vinyl ether (64.8 ml, 674 mmol) were added dropwise through an addition funnel to maintain the internal temperature no greater than −20° C. After the addition was complete, the mixture was slowly warmed to ambient temperature overnight. The reaction was then dilted with dichloromethane (500 mL) along with water (500 mL). The dichloromethane layer was dried, filtered and concentrated under reduced pressre (300 mbar at 30° C.) to volume of about 150 mL and then used directly in step 3.

Step 2: To 3-bromo-5-methylaniline (170 g, 914 mmol) in EtOH (760 mL) was added cyanamide (50 wt % in water, 82 mL, 1050 mmol) and nitric acid (70%, 64.2 mL, 1005 mmol). The mixture was refluxed at 90° C. overnight, then cooled to ambient temperature. The reaction was concentrated in vacuo to about 600 mL, then cold ether (1500 mL) was added with vigorous stirring. The resulting precipitate was filtered and washed with 150 mL ether to afford 1-(3-bromo-5-methylphenyl)guanidine nitrate. MS ESI calc'd. for C$_8$H$_{11}$BrN$_3$ [M+H]$^+$ 228, 230. found 228, 230. $^1$H NMR (600 MHz, DMSO-d$_6$) δ 9.56 (s, 1H), 7.41 (s, 4H), 7.30 (s, 1H), 7.21 (s, 1H), 7.03 (s, 1H), 2.27 (s, 3H).

Step 3: A mixture of (3E)-4-ethoxy-1,1-difluorobut-3-en-2-one from Step 1 (79 g, 527 mmol, containing DCM), 1-(3-bromo-5-methylphenyl)guanidine nitrate (123 g, 423 mmol) and potassium carbonate (117 g, 845 mmol) in EtOH (604 ml) was heated at 85° C. for 1 h and then slowly cooled to ambient temperature. Ice water (2 L) was added to the mixture and stirred for 15 min. The resulting precipitate was filtered and dried overnight to afford N-(3-bromo-5-methylphenyl)-4-(difluoromethyl)pyrimidin-2-amine.

MS ESI calc'd. for $C_{12}H_{11}BrF_2N_3$ [M+H]$^+$ 314, 316. found 314, 316. $^1$H NMR (600 MHz, CDCl$_3$) δ 8.58 (d, J=4.9, 1H), 7.75 (s, 1H), 7.32 (s, 1H), 7.21 (s, 1H), 7.01 (s, 1H), 7.00 (d, J=4.9, 1H), 6.40 (t, J=60.0, 1H), 2.30 (s, 3H).

Step 4: The mixture of N-(3-bromo-5-methylphenyl)-4-(difluoromethyl)pyrimidin-2-amine (98 g, 312 mmol), bis(pinacoloato)diboron (91 g, 359 mmol), Pd(dppf)Cl$_2$·CH$_2$Cl$_2$ (12.74 g, 15.6 mmol) and potassium acetate (77 g, 780 mmol) in dioxane (520 mL) was degassed with N$_2$ for 10 min and then heated to 85° C. for 22 h. After cooling to room temperature, water and EtOAc were added. The organic layer was washed with water and brine, dried over magnesium sulfate, filtered and concentrated in vacuo. The residue was purified by column chromatography on silica gel (750 g, 0-50% EtOAc in hex) to afford 4-(difluoromethyl)-N-[3-methyl-5-(4,4,5,5-tetramethyl-1,3,2-dioxaborolan-2-yl)phenyl]pyrimidin-2-amine. MS ESI calc'd. for $C_{18}H_{23}BF_2N_3O_2$ [M+H]$^+$ 362. found 362. $^1$H NMR (600 MHz, CDCl$_3$) δ 8.56 (s, 1H), 7.74 (s, 1H), 7.59 (s, 1H), 7.45 (s, 1H), 7.35 (s, 1H), 6.94 (s, 1H), 6.38 (t, J=55.0, 1H), 2.36 (s, 3H), 1.33 (s, 12H).

Step 5: 2-Methyl-THF (964 mL) and aqueous sodium carbonate (2 M, 247 mL, 494 mmol) were added to a flask and degassed with N$_2$. To that mixture was added 4-(difluoromethyl)-N-[3-methyl-5-(4,4,5,5-tetramethyl-1,3,2-dioxaborolan-2-yl)phenyl]pyrimidin-2-amine (94 g, 259 mmol), butyl trans-4-[(1R or S)-(5-bromo-1,3-thiazol-2-yl)-1-hydroxyethyl]cyclohexanecarboxylate (Ex 19, Step 3, R$_t$=7.86 min) (96.3 g, 247 mmol) and PdCl$_2$(dppf)-CH$_2$Cl$_2$ (10.1 g, 12.3 mmol, 5 mol %). The resulting mixture was heated to 75° C. and stirred for 3 h, then cooled to room temperature, diluted with H$_2$O and EtOAc, then filtered through a pad of CELITE washing with both H$_2$O and EtOAc. The layers were separated, the aqueous layer back extracted with EtOAc, then the combined organics were dried over MgSO$_4$, filtered, and concentrated in vacuo. The crude residue was absorbed on silica and purified by flash chromatography to afford butyl trans-4-{(1R or S)-[5-(3-{[4-(difluoromethyl)pyrimidin-2-yl]amino}-5-methylphenyl)-1,3-thiazol-2-yl]-1-hydroxyethyl}cyclohexanecarboxylate as a viscous yellow oil. MS ESI calc'd. for $C_{28}H_{35}F_2N_4O_3S$ [M+H]$^+$ 545. found 545. $^1$H NMR (500 MHz, DMSO-d$_6$) δ 10.02 (s, 1H), 8.71 (d, J=4.9, 1H), 7.94 (s, 2H), 7.49 (s, 1H), 7.09 (s, 1H), 7.07 (d, J=4.9, 1H), 6.87 (t, J=54.6, 1H), 5.84 (s, 1H), 3.96 (t, J=6.5, 2H), 2.30 (s, 3H), 2.17-2.05 (m, 1H), 1.97-1.81 (m, 4H), 1.70-1.60 (m, 1H), 1.58-1.44 (m, 5H), 1.32-1.19 (m, 6H), 0.85 (t, J=7.4, 3H). rhSyk=++

Step 6: To a solution of butyl trans-4-{(1R or S)-[5-(3-{[4-(difluoromethyl)pyrimidin-2-yl]-amino}-5-methylphenyl)-1,3-thiazol-2-yl]-1-hydroxyethyl}cyclohexanecarboxylate (113 g, 208 mmol) in MeOH (1493 mL) was added NaOH (1 M in H$_2$O, 726 mL, 726 mmol) and the resulting heterogenous mixture heated to 70° C. After 1 h, the reaction mixture was removed from heat and cooled. Upon reaching 55° C. the dropwise addition of HCl (1 M in H$_2$O, 726 mL, 726 mmol) was initiated resulting in crystallization. The heterogeneous mixture was stirred for 1 h at room temperature, then filtered and washed twice with water. The filter cake was dried under a nitrogen bag for 14 h and then taken up in EtOAc (1.8 L) and the resulting slurry heated to reflux and stirred for 2 h. After cooling to 60° C., hexanes (1.8 L) was added over 20 min, the reaction mixture was then cooled to room temperature, filtered and the cake washed with hexanes (2×400 mL), then dried under a nitrogen bag for 18 h to afford trans-4-{(1R or S)-[5-(3-{[4-(difluoromethyl)pyrimidin-2-yl]amino}-5-methylphenyl)-1,3-thiazol-2-yl]-1-hydroxyethyl}cyclohexanecarboxylic acid as a light yellow solid. MS ESI calc'd. for $C_{24}H_{27}F_2N_4O_3S$ [M+H]$^+$ 489. found 489. $^1$H NMR (500 MHz, DMSO-d$_6$) δ 11.90 (s, 1H), 10.02 (s, 1H), 8.71 (d, J=4.9, 1H), 7.96-7.90 (m, 2H), 7.49 (s, 1H), 7.09 (s, 1H), 7.07 (d, J=4.9, 1H), 6.87 (t, J=54.5, 1H), 5.82 (s, 1H), 2.30 (s, 3H), 2.01 (s, 1H), 1.95-1.81 (m, 4H), 1.70-1.58 (m, 1H), 1.58-1.51 (m, 1H), 1.47 (s, 3H), 1.29-1.13 (m, 2H), 1.10-0.96 (m, 1H). rhSyk=+++.

EXAMPLE 22

1,4-dioxaspiro[4.5]dec-8-yl[5-(3-methyl-5-{[4-(trifluoromethyl)pyrimidin-2-yl]amino}phenyl)-1,3-thiazol-2-yl]methanol

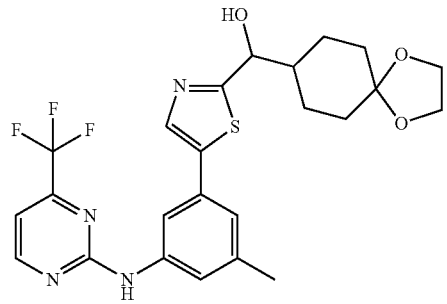 [SMILES: Cc1cc(Nc2nccc(C(F)(F)F)n2)cc(-c2cnc(C(O)C3CCC4(CC3)OCCO4)s2)c1]

To a solution of 1,4-dioxaspiro[4.5]dec-8-yl[5-(3-methyl-5-{[4-(trifluoromethyl)pyrimidin-2-yl]amino}phenyl)-1,3-thiazol-2-yl]methanone (Ex 1-20) (100 mg, 0.20 mmol) in methanol (5 mL) was added sodium borohydride (22.5 mg, 0.60 mmol). After one hour, water was carefully added and then diluted with ethyl acetate and water. The organic layer was separated, dried over sodium sulfate, filtered and concentrated in vacuo. Flash chromatography on silica gel (0-100% ethyl acetate gradient with hexanes) afforded 1,4-dioxaspiro[4.5]dec-8-yl[5-(3-methyl-5-{[4-(trifluoromethyl)pyrimidin-2-yl]amino}phenyl)-1,3-thiazol-2-yl]methanol. MS ESI calc'd. for $C_{24}H_{26}F_3N_4O_3S$ [M+H]$^+$ 507. found 507. $^1$H NMR (500 MHz, DMSO-d$_6$) δ 10.24 (s, 1H), 8.83 (d, J=4.9, 1H), 7.97-7.94 (m, 2H), 7.45 (s, 1H), 7.27 (d, J=4.9, 1H), 7.15 (s, 1H), 6.18 (d, J=5.1, 1H), 4.61 (t, J=5.1, 1H), 3.80 (s, 4H), 2.30 (s, 3H), 1.84-1.72 (m, 1H), 1.71-1.61 (m, 2H), 1.61-1.51 (m, 2H), 1.52-1.28 (m, 4H). rhSyk=++.

EXAMPLE 23

4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanol

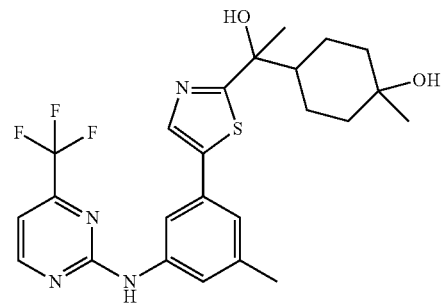 [SMILES: Cc1cc(Nc2nccc(C(F)(F)F)n2)cc(-c2cnc(C(C)(O)C3CCC(C)(O)CC3)s2)c1]

Step 1: Lithium diisopropyl amide (1.8 M in tetrahydrofuran/ heptane/ethylbenzene, 3.96 mL, 7.14 mmol) was added to a solution of N-[3-methyl-5-(1,3-thiazol-5-yl)phenyl]-4-(trifluoromethyl)pyrimidin-2-amine (800 mg, 2.38 mmol) in THF (5 mL) at −78° C. After 30 minutes at −78° C., a solution of N-methoxy-N-methyl-1,4-dioxaspiro[4.5]decane-8-carboxamide (1.09 g, 4.76 mmol) in THF (8 mL) was added slowly and the reaction was allowed to warm to room temperature then stirred for 16 hours. The reaction was diluted carefully with water and then ethyl acetate and brine. The organic layer was separated, dried over sodium sulfate, filtered and concentrated in vacuo. Purification by HPLC (acetonitrile/water with a 0.1% TFA modifier) afforded a mixture of 1,4-dioxaspiro[4.5]dec-8-yl[5-(3-methyl-5-{[4-(trifluoromethyl)pyrimidin-2-yl]amino}phenyl)-1,3-thiazol-2-yl]methanone and 4-{[5-(3-methyl-5-{[4-(trifluoromethyl)pyrimidin-2-yl]amino}phenyl)-1,3-thiazol-2-yl]carbonyl}cyclohexanone that was taken on to the next step with no further purification.

Step 2: Methylmagnesium bromide (3.0 M in diethyl ether, 0.2 mL, 0.60 mmol) was added to a solution of the product from Step 1 (190 mg, 0.42 mmol) in dichloromethane (5 mL) at 0° C. The reaction was then warmed to room temperature and stirred for 3 days. The reaction was then cooled to 0° C. and more methylmagnesium bromide (3.0 M in diethyl ether, 0.2 mL, 0.60 mmol) was added. The reaction was then diluted carefully with water thendichloromethane and saturated aqueous ammonim chloride. The organic layer was separated, dried over sodium sulfate, filtered and concentrated in vacuo. Purification by HPLC (acetonitrile/water with 0.1% TFA as a modifier) afforded desired fractions that were combined and then diluted with ethyl acetate and saturated aqueous sodium bicarbonate. The organic layer was separated, dried over sodium sulfate, filtered and concentrated in vacuo to afford 4-{1-hydroxy-1-[5-(3-methyl-5-{[4-(trifluoromethyl)pyrimidin-2-yl]amino}phenyl)-1,3-thiazol-2-yl]ethyl}-1-methylcyclohexanol as a mixture of isomers. MS ESI calc'd. for $C_{24}H_{28}F_3N_4O_3S$ [M+H]$^+$ 493, found 493. NMR data for the major isomer: $^1$H NMR (500 MHz, CD$_3$OD) δ 8.71 (d, J=4.9, 1H), 8.02 (d, J=9.3, 1H), 7.93 (s, 1H), 7.44 (s, 1H), 7.12 (d, J=4.7, 2H), 2.37 (s, 3H), 2.03 (s, 3H), 2.01 (s, 3H), 1.79-1.25 (m, 9H). rhSyk=+++.

What is claimed is:
1. A compound of formula I:

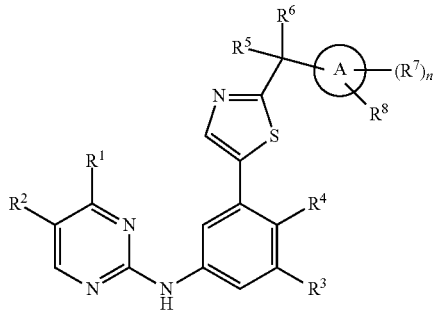

or a pharmaceutically acceptable salt thereof,
wherein
A is a carbocycle;
n is 0, 1, 2 or 3;

$R^1$ is $C_{1-4}$alkyl, $C_{1-4}$fluoroalkyl, $C_{3-6}$cycloalkyl or $C_{1-4}$alkoxy;

$R^2$ is H or halogen;

$R^3$ is H, halogen, $C_{1-4}$alkyl, $C_{1-4}$haloalkyl, $C_{3-6}$cycloalkyl or $C_{1-4}$hydroxyalkyl;

$R^4$ is H or halogen;

$R^5$ is OH;

$R^6$ is H, $C_{1-4}$alkyl, $C_{1-4}$haloalkyl, $C_{3-6}$cycloalkyl or $C_{1-4}$hydroxyalkyl;

$R^7$ is selected from OH and $C_{1-4}$alkyl;

$R^8$ is selected from $(CR^aR^b)_nCO_2R^c$, $CONR^dR^e$, tetrazolyl, OH, CH$_2$OH, oxo, CN, NHCO$_2R^f$ and NHSO$_2R^f$ with the proviso that $R^8$ and —C($R^5$)($R^6$)— are not attached to the same ring carbon atom;

$R^a$ and $R^b$ are each independently selected from H and methyl;

$R^c$ is H or $C_{1-4}$alkyl, $R^d$ and $R^e$ are each independently selected from H and $C_{1-4}$alkyl;

$R^f$ is $C_{1-4}$alkyl or benzyl;

wherein said carbocycle is a non-aromatic saturated or partially unsaturated monocyclic ring in which all ring atoms are carbon, the ring being isolated or fused, including ortho-fused, spiro-fused and bridged, to one or two such rings or to a benzene ring.

2. A compound of claim 1 or a pharmaceutically acceptable salt thereof, wherein $R^1$ is $C_{1-4}$alkyl or $C_{1-4}$fluoroalkyl.

3. A compound of claim 1 or a pharmaceutically acceptable salt thereof, wherein A is a carbocycle, and $R^8$ is selected from $(CR^aR^b)_nCO_2R^c$ and C(O)NR$^d$R$^e$.

4. The compound of claim 1 having the formula Ia:

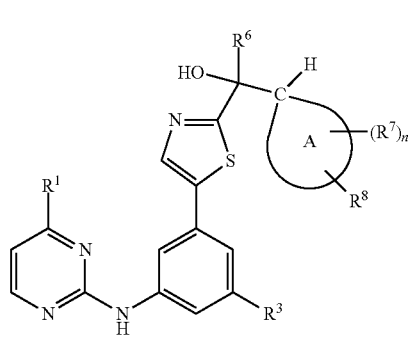

or a pharmaceutically acceptable salt thereof,
wherein
A is a carbocycle;
n is 0, 1 or 2;
$R^1$ is $C_{1-4}$alkyl or $C_{1-4}$fluoroalkyl;
$R^3$ is $C_{1-4}$alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$alkyl;
$R^8$ is CO$_2$R$^c$ or CONR$^d$R$^e$;
$R^c$ is H or $C_{1-4}$alkyl,
$R^d$ and $R^e$ are each independently selected from H and $C_{1-4}$alkyl.

5. A compound of claim 1 having the formula Ib:

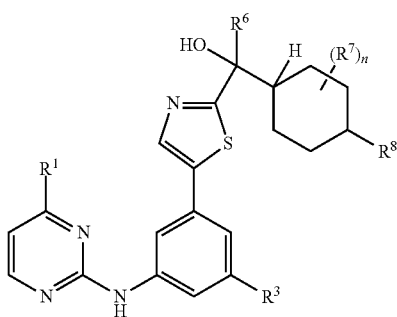

Ib or a pharmaceutically acceptable salt thereof,
wherein
n is 0, 1 or 2;
$R^1$ is $C_{1-4}$alkyl or $C_{1-4}$fluoroalkyl;
$R^3$ is $C_{1-4}$alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$alkyl;
$R^8$ is $CO_2R^c$ or $CONR^dR^e$;
$R^c$ is H or $C_{1-4}$alkyl,
$R^d$ and $R^e$ are each independently selected from H and $C_{1-4}$alkyl.

6. A compound of claim 5 or a pharmaceutically acceptable salt thereof, wherein $R^8$ is $CO_2R^c$.

7. A compound of claim 5 having the formula Ic:

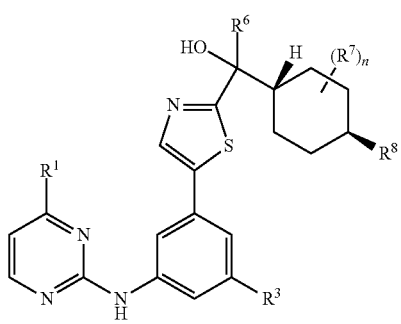

Ic or a pharmaceutically acceptable salt thereof,
wherein n, $R^1$, $R^3$, $R^6$, $R^7$, $R^8$, $R^c$, $R^d$, and $R^e$ are as set forth in claim 5.

8. The compound of claim 7 or a pharmaceutically acceptable salt thereof, wherein $R^8$ is $CO_2R^c$.

9. The compound of claim 1, 4-{hydroxy[5-(3-methyl-5-{[4-(trifluoromethyl)pyrimidin-2-yl]amino}phenyl)-1,3thiazol-2-yl]methyl}cyclohexanecarboxylic acid, or a pharmaceutically acceptable salt thereof.

10. The compound of claim 1, 4-hydroxy-1-(5-}3-methyl-5-[(4methylpyrimidin-2-yl)amino]phenyl}-1,3-thiazol-2yl)ethyl]-2-methylcyclohexanecarboxylic acid, or a pharmaceutically acceptable salt thereof.

11. The compound of claim 1, 4-{1-hydroxy-1-[5-(3-methyl-5-{[4-(trifluormethyl)pyrimidin-2-yl]amino}phenyl)-1,3-thiazol 2-yl]theyl}-2-methylcyclohexanecarboxylic acid, or a pharmaceutically acceptable salt thereof.

12. The compound of claim 1, 4-{1-[5-(3-{[4-(difluoromethyl)pyrimidin-2-yl]amino}-5-methylphenyl)-1,3-thiazol-2-yl]-1hydroxyethyl}-2-methylcyclohexanecarboxylic acid, or a pharmaceutically acceptable salt thereof.

13. The compound of claim 1, 4-[hydroxy-1(5-{3-methyl-5-[(4-methylpyrimidin-2yl)amino]phenyl}-1,3thiazol-2yl) ethyl]cyclohexanecarboxylic acid, or a pharmaceutically acceptable salt thereof.

14. The compound of claim 1, 4-{1-[5-(3-{[4-(difluoromethyl)pyrimidin-2-yl]amino}-5-methylphenyl)-1,3thiazol-2-yl]-1-hydroxyethyl}cyclohexanecarboxylic acid, or a pharmaceutically acceptable salt thereof.

15. The compound of claim 1, 4-{1-hydroxy-1-[5-(3-methyl-5-{[4-(trifluoromethyl)pyrimidin-2-yl]amino}phenyl)-1,3-thiazol-2-yl]ethyl}cyclohexanecarboxylic acid, or a pharmaceutically acceptable salt thereof.

16. The compound of claim 1, trans-4-{(1R)-1-hydroxy-1-[5-(3-methyl-5-{[4-(trifluoromethyl)pyrimidin-2-yl]amino}phenyl)-1,3 -thiazol-2-yl] ethyl}cyclohexanecarboxylic acid, or a pharmaceutically acceptable salt thereof.

17. The compound of claim 1, trans-4-{(1S)-1-hydroxy-1-[5-(3-methyl-5-{[4-(trifluoromethyl)pyrimidin-2-yl]amino}phenyl)-1,3-thiazol-2-yl] ethyl}cyclohexanecarboxylic acid, or a pharmaceutically acceptable salt thereof.

18. The compound of claim 1, (1S,2R,4S)-4-[1(R)-hydroxy-1-(5-{3-methyl-5-[(4-methylpyrimidin-2-yl)amino]phenyl}-1,3 -thiazol-2-yl)ethyl]-2-methylcyclohexanecarboxylic acid, or a pharmaceutically acceptable salt thereof.

19. The compound of claim 1, (1S,2R,4S)-4-[1(S)-hydroxy-1-(5-{3-methyl-5-[(4-methylpyrimidin-2-yl)amino]phenyl}-1,3-thiazol-2-yl)ethyl]-2-methylcyclohexanecarboxylic acid, or a pharmaceutically acceptable salt thereof.

20. The compound of claim 1, (1R,2S,4R) 4-[1(R)-hydroxy-1-(5-{3-methyl-5-[(4-methylpyrimidin-2-yl)amino]phenyl}-1,3-thiazol-2-yl)ethyl]-2-methylcyclohexanecarboxylic acid, or a pharmaceutically acceptable salt thereof.

21. The compound of claim 1, (1R,2S,4R)-4-[1(S)-hydroxy-1-(5-{3-methyl-5-[(4-methylpyrimidin-2-yl)amino]phenyl}-1,3-thiazol-2-yl)ethyl]-2-methylcyclohexanecarboxylic acid, or a pharmaceutically acceptable salt thereof.

22. A pharmaceutical composition comprising a therapeutically effective amount of a compound of claim 1 or a pharmaceutically acceptable salt thereof, and a pharmaceutically acceptable carrier.

23. A method for the treatment of asthma, comprising administering a therapeutically effective amount of the compound of claim 1 or a pharmaceutically acceptable salt thereof to a patient in need of such treatment.

24. A method for the treatment of non-Hodgkin B cell lymphoma, comprising administering a therapeutically effective amount of the compound of claim 1 or a pharmaceutically acceptable salt thereof to a patient in need of such treatment.

25. A method for the treatment of systemic lupus erythematosis, comprising administering a therapeutically effective amount of the compound of claim 1 or a pharmaceutically acceptable salt thereof to a patient in need of such treatment.

* * * * *